US011579141B2

(12) United States Patent
Wolff-Winiski et al.

(10) Patent No.: US 11,579,141 B2
(45) Date of Patent: Feb. 14, 2023

(54) METHODS FOR IDENTIFYING A NON-HEALING SKIN WOUND AND FOR MONITORING THE HEALING OF A SKIN WOUND

(71) Applicant: AKRIBES BIOMEDICAL GMBH, Vienna (AT)

(72) Inventors: Barbara Wolff-Winiski, Vienna (AT); Anton Stütz, Altmünster (AT); Petra Dörfler, Brunn am Gebirge (AT)

(73) Assignee: AKRIBES BIOMEDICAL GMBH, Vienna (AT)

(*) Notice: Subject to any disclaimer, the term of this patent is extended or adjusted under 35 U.S.C. 154(b) by 651 days.

(21) Appl. No.: 16/344,356

(22) PCT Filed: Oct. 23, 2017

(86) PCT No.: PCT/EP2017/076983
§ 371 (c)(1),
(2) Date: Apr. 23, 2019

(87) PCT Pub. No.: WO2018/077792
PCT Pub. Date: May 3, 2018

(65) Prior Publication Data
US 2020/0025746 A1    Jan. 23, 2020

(30) Foreign Application Priority Data
Oct. 24, 2016  (EP) .................................... 16002266

(51) Int. Cl.
G01N 33/50    (2006.01)
G16H 50/50    (2018.01)
G16H 50/30    (2018.01)
C12Q 1/6886   (2018.01)

(52) U.S. Cl.
CPC ..... *G01N 33/5091* (2013.01); *G01N 33/5023* (2013.01); *G01N 33/5055* (2013.01); *G16H 50/30* (2018.01); *G16H 50/50* (2018.01); *C12Q 1/6886* (2013.01); *C12Q 2600/118* (2013.01); *G01N 2800/20* (2013.01); *G01N 2800/52* (2013.01); *G01N 2800/60* (2013.01)

(58) Field of Classification Search
CPC .......... G01N 33/5023; G01N 33/5055; G01N 2800/20; G01N 2800/52; G01N 2800/60; G16H 50/30; G16H 50/50; C12Q 2600/118
See application file for complete search history.

(56) References Cited

U.S. PATENT DOCUMENTS

| | | | |
|---|---|---|---|
| 5,283,173 A | 2/1994 | Fields et al. | |
| 5,468,614 A | 11/1995 | Fields et al. | |
| 2003/0165482 A1* | 9/2003 | Rolland | A61K 38/4833 |
| | | | 424/93.21 |
| 2012/0237500 A1 | 9/2012 | Milstein et al. | |
| 2014/0010838 A1* | 1/2014 | Zanella | A61K 8/9794 |
| | | | 424/195.17 |
| 2015/0353605 A1* | 12/2015 | Zhang | A61Q 19/08 |
| | | | 514/21.8 |

FOREIGN PATENT DOCUMENTS

| | | |
|---|---|---|
| AU | 2007203472 A1 | 8/2007 |
| JP | 2004-121819 A | 4/2004 |
| JP | 2004-517078 A | 6/2004 |
| WO | 98/54575 A2 | 12/1998 |
| WO | 02/43758 A2 | 6/2002 |
| WO | 2004/022077 A1 | 3/2004 |
| WO | 2013/060321 A2 | 5/2013 |
| WO | 2016092542 A1 | 6/2016 |
| WO | 2016/113400 A1 | 7/2016 |
| WO | 2017/089005 A1 | 6/2017 |

OTHER PUBLICATIONS

Song (Zhongguo xiufu chongjian waike zazhi (English translated Chinese journal of reparative and reconstructive surgery) (Jan. 1999) vol. 13, No. 1, pp. 47-50. Chinese but summarized in English (Abs, Methods, Results and Conclusion) (Year: 1999).*
Bromberek (Experimental Cell Res 2002 275:230) "Macrophages influence a competition of contact guidance and chemotaxis for fibroblast alignment in a fibrin gel coculture asay". (Year: 2002).*
Mann J. Inves. Dermatol. 2001 117: 1382) "Keratinocyte-derived granulocyte-macrophage colony stimulating factor accelerates wound healing: stimulation of keratinocyte proliferation, granulation tissue formation, and vascularization". (Year: 2001).*
Falanga, V. (1992) "Growth Factors and Chronic Wounds: The Need to Understand the Microenvironment". The Journal of Dermatology, 19:667-672.
Harris, I.R. et al. (Dec. 1995) "Cytokine and protease levels in healing and non-healing chronic venous leg ulcers". Exp Dermatol. 4(6):342-349. doi: 10.1111/j.1600-0625.1995.tb00058.x. PMID: 8608341.
Keith Moore et al: "Venous leg ulcers ? the search for a prognostic indicator", International Wound Journal, vol. 4, No. 2, Jun. 1, 2007 (Jun. 1, 2007), pp. 163-172, XP055021820, ISSN: 1742-4801, DOI: 10.1111/.1742-481X.2007.00335.x, the whole document.
Melanie Martini et al: "The candidate tumor suppressorinteracts with the actin cytoskeleton and stimulates cellmatrix adhesion",International Journal of Biochemistry and Cell Biology, Pergamon, GB, vol. 43, No. 11, Jul. 21, 2011 (Jul. 21, 2011), pp. 1630-1640, XP028300284, ISSN: 1357-2725, DOI: 10.1016/3. BIOCEL.2011.07.012 [retrieved on Jul. 28, 2011], p. 1632, left-hand column, paragraph 2—right-hand column, last paragraph.
Mendez M V et al: "The proliferative capacity of neonatal skin fibroblasts is reduced after exposure to venous ulcer wound fluid: A potential mechanism for senescence in venous ulcers", Journal of Vascular Surgery, C.V. Mosby Co., St.Louis,Mo, US, vol. 30, No. 4, Oct. 1, 1999 (Oct. 1, 1999), pp. 734-743, XP027585008, ISSN: 0741-5214 [retrieved on Oct. 1, 1999] abstract p. 735, left-hand column, last paragraph—right-hand column, last paragraph figure 1.

(Continued)

Primary Examiner — Changhwa J Cheu
(74) Attorney, Agent, or Firm — Melissa Hunter-Ensor; Evelyn Kwon; Greenberg Traurig, LLP

(57) ABSTRACT

The present invention relates to an in vitro method for identifying a skin wound in an individual as being a non-healing skin wound or healing skin wound, in vitro methods for monitoring the healing of a skin wound in an individual, methods for screening for compounds suitable for modulating skin wound healing, as well as kits related thereto.

8 Claims, 50 Drawing Sheets

(56) References Cited

OTHER PUBLICATIONS

Figure 1:
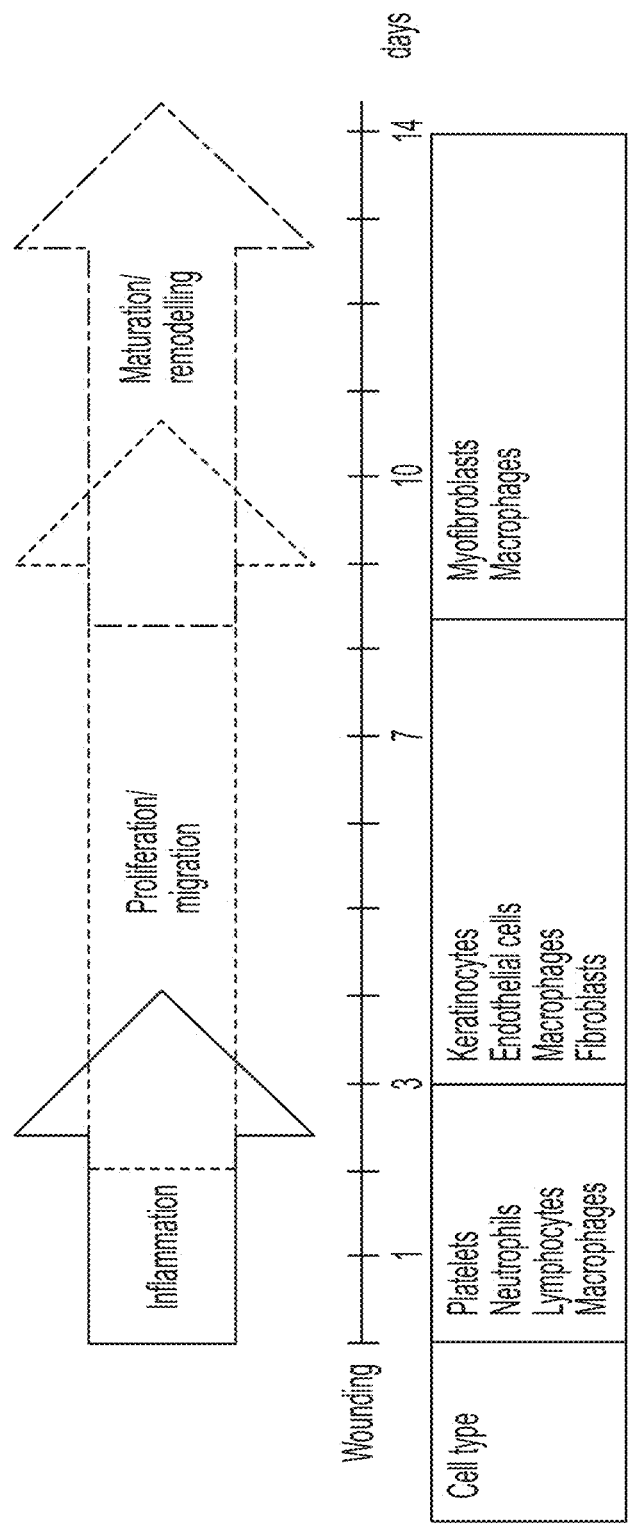

Pricolo V E et al: "Modulatory activities of wound fluid on fibroblast proliferation and collagen synthesis", Journal of Surgical Research, Academic Pressinc., San Diego, CA, US, vol. 48, No. 6, Jun. 1, 1990 (Jun. 1, 1990), pp. 534-538, XP023024115, ISSN: 0022-4804, DOI: 10.1016/0022-4804(90)90226-R [retrieved on Jun. 1, 1990], abstract p. 535, left-hand column, paragraph 3—right-hand column, paragraph 1.
Oliver C Thamm et al: "Acute and chronic wound fluids influence keratinocyte function differently", International Wound Journal, vol. 12, No. 2, Mar. 21, 2013 (Mar. 21, 2013), pp. 143-149, XP055364447, UK ISSN: 1742-4801, DOI: 10.1111/iwj.12069, abstract p. 144, left-hand column, paragraph 2—right-hand column, last paragraph.
Arrowsmith et al., "Phase II and Phase III attrition rates 2011-2012", Nature Reviews Drug Discovery, Aug. 2013, vol. 12, p. 569.
Atac et al., "Skin and Hair On-a-Chip: In Vitro Skin Models Versus Ex Vivo Tissue Maintenance with Dynamic Perfusion", Lab on a Chip, The Royal Society of Chemistry, 2013, vol. 13, pp. 3555-3561.
Clark et al., "Tissue Engineering for Cutaneous Wounds", Journal of Investigative Dermatology, 2007, vol. 127, p. 1018-1029.
Clotworthy et al., "Advances in the Development and Use of Human Tissue-Based Techniques for Drug Toxicity Testing", Expert Opinion on Drug Metabolism & Toxicology, 2013, vol. 9, No. 9, p. 1155-1169.
Clotworthy "The Application of Human Tissue for Drug Discovery and Development", Expert Opinion on Drug Discovery, 2012, vol. 7, No. 7, p. 543-547.
Coleman "Human Tissue in the Evaluation of Safety and Efficacy of New Medicines: A Viable Alternative to AnimalModels?", ISRN Pharmaceutics, Article ID 806789, 2011, vol. 2011, 8 pages.
Dimasi et al., "Trends in Risks Associated With New Drug Development: Success Rates for Investigational Drugs", Clinical Pharmacology & Therapeutics, Mar. 2010, vol. 87, No. 3, pp. 272-277.
Dissemond et al., "Modern Wound Care—Practical Aspects of Non-Interventional Topical Treatment of Patients with Chronic Wounds", Journal of the German Society of Dematology, May 12, 2014, vol. 12, No. 7, pp. 541-554.
Eming et al., "Wound Repair and Regeneration: Mechanisms, Signaling, and Translation", Science Translational Medicine, Dec. 3, 2014, vol. 6, No. 265, 36 pages.
Gottrup et al., "A Specialized Wound-Healing Center Concept: Importance of a Multidisciplinary Department Structure and Surgical Treatment Facilities in the Treatment of Chronic Wounds", The American Journal of Surgery, May 2004, vol. 187, pp. 38S-43S.
Gurtner et al., "Wound Repair and Regeneration", Nature, May 15, 2008, vol. 453, pp. 314-321.
Hay et al., "Clinical Development Success Rates for Investigational Drugs", Nature Biotechnology, Jan. 2014, vol. 32, No. 1, pp. 40-51.
Hengge et al., "Adverse Effects of Topical Glucocorticosteroids", Journal of the American Academy of Dermatology, Jan. 2006, vol. 54, No. 1, pp. 1-15.
Nieva et al., "Fluid Biopsy for Solid Tumors: A Patient's Companion for Lifelong Characterization of Their Disease", Future Oncology, Aug. 2012, vol. 8, No. 8, pp. 989-998.
Sindrilaru et al., "Disclosure of the Culprits: Macrophages—Versatile Regulators of Wound Healing", Advances in Wound Care, 2013, vol. 2, No. 7, pp. 357-368.
Song et al., "Influence of Irradiation on the Modulatory Effect of Wound Fluid on Fibroblasts Characteristics and the Application of Phenytoin Sodium," Chinese Journal of Reparative and Reconstructive Surgery, 1999, vol. 13, No. 1, pp. 47-50.
Song et al., "Influence of Irradiation on the Modulatory Effect of Wound Fluid on Fibroblasts Characteristics and the Application of Phenytoin Sodium," Chinese Journal of Reparative and Reconstructive Surgery, 1999, vol. 13, No. 1, pp. 47-50. [English Translation, pp. 1-6].

\* cited by examiner

A

Figure 6:
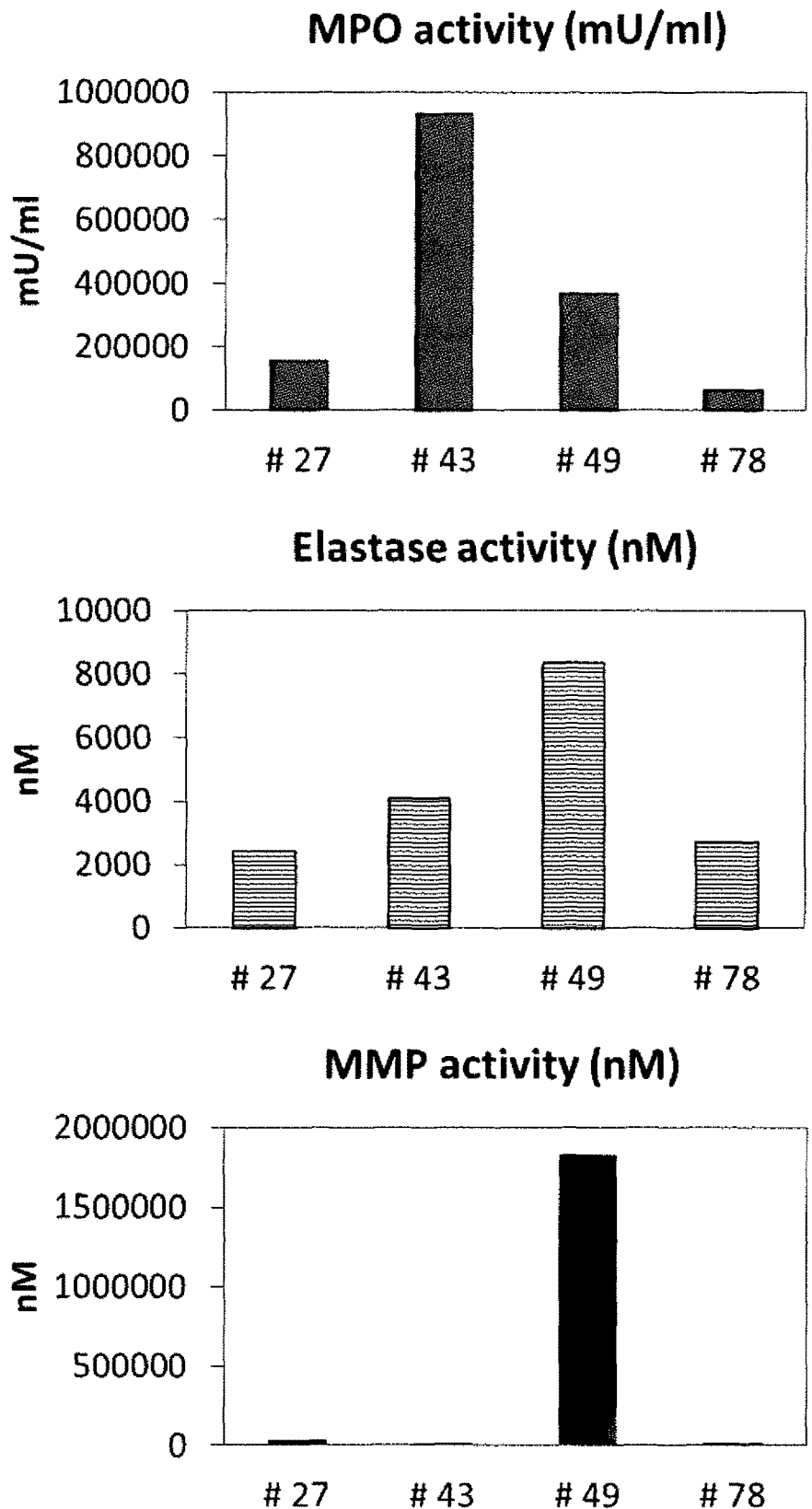

Figure 6 (ctd.)
B
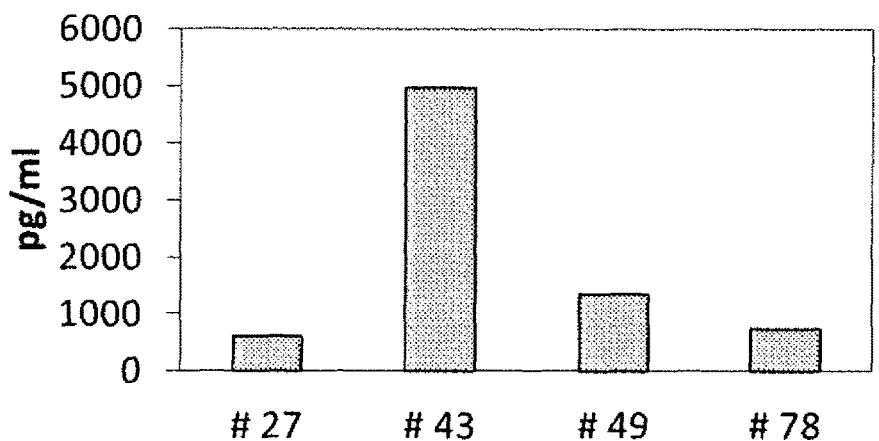
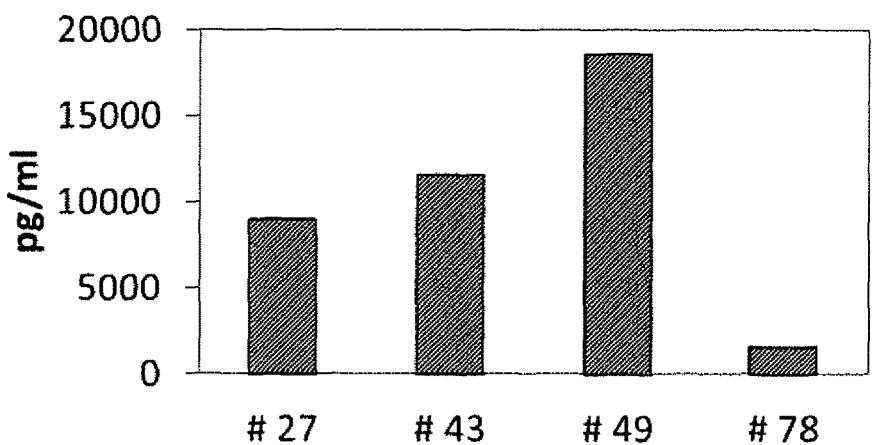
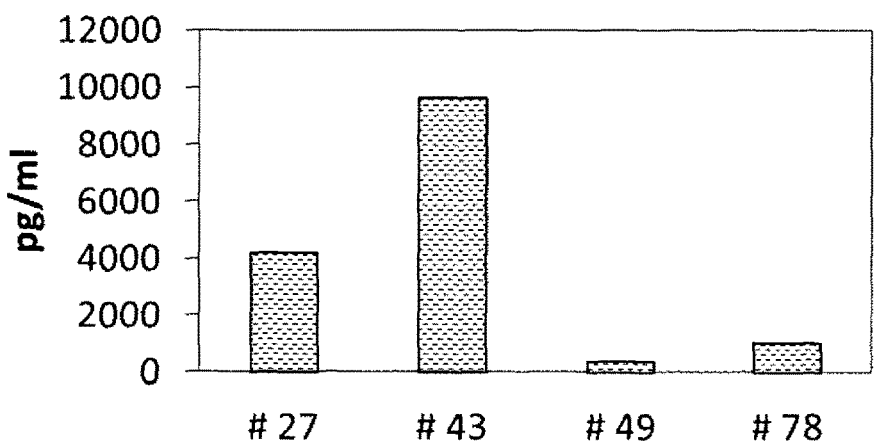

Figure 6 (ctd.)
C
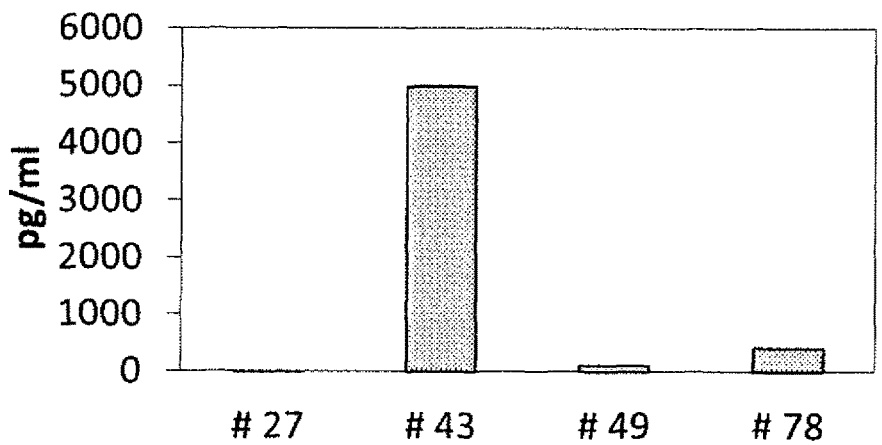
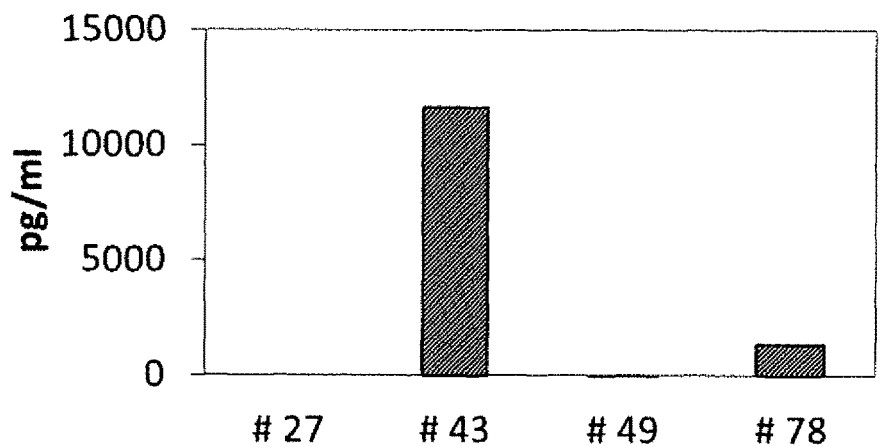
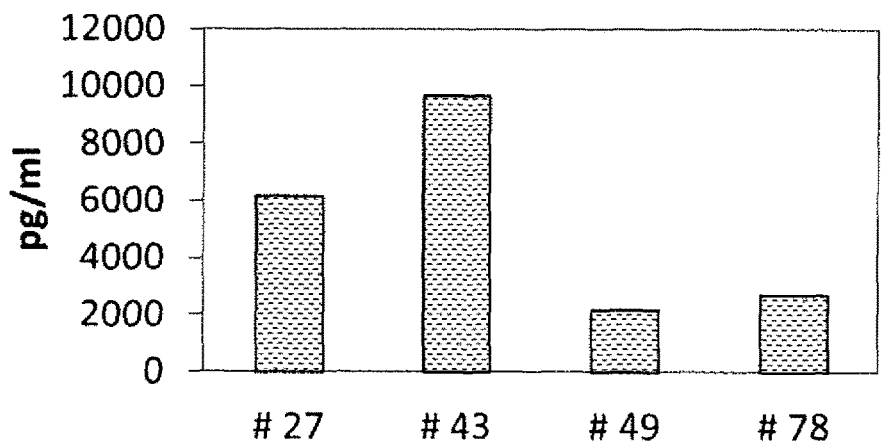

| Wound phenotype | # of patients (# of exudates) | Patient age | Diagnosis |
|---|---|---|---|
| non-healing | 12 (50) | 56 - 94 | Ulcus cruris arteriosum, ulcus cruris venosum, "Gamaschenulcus", diabetic ulcer, diabetic ulcer, venous ulcer, surgical wound |
| non-healing → healing | 2 (10) | 76 - 84 | Ulcus cruris arteriosum, foot ulcer |
| healing | 9 (13) | 31 - 74 | Ulcus cruris arteriosum, surgical wound, pressure ulcer |

Figure 7

Exudate levels

Figure 26:
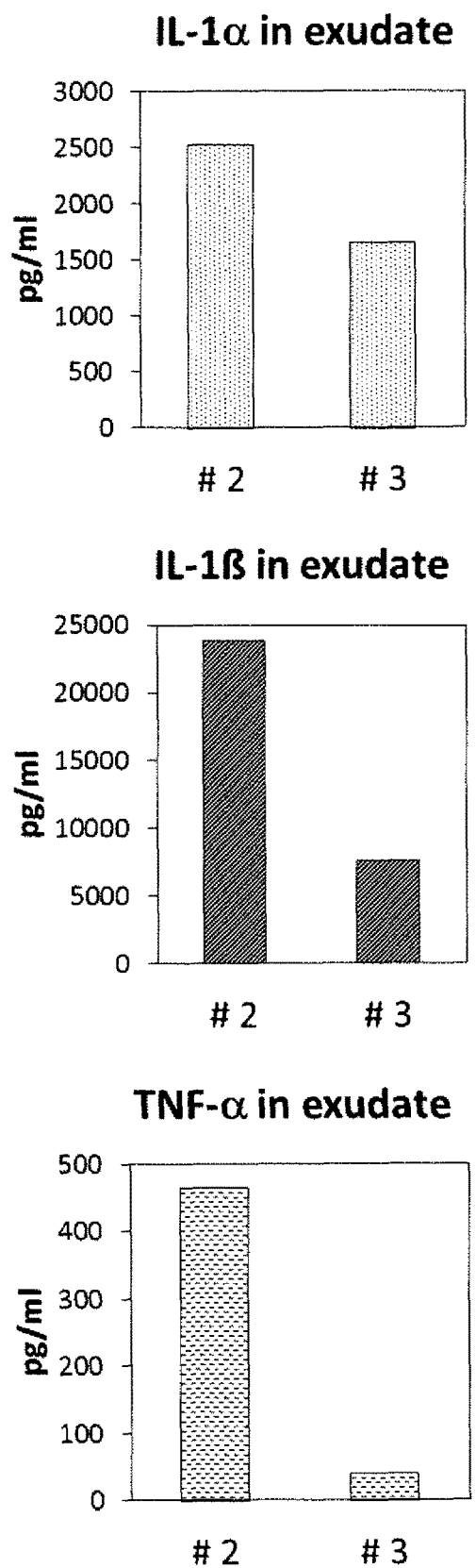

Figure 26 (ctd.)
Levels in macrophage supernatants
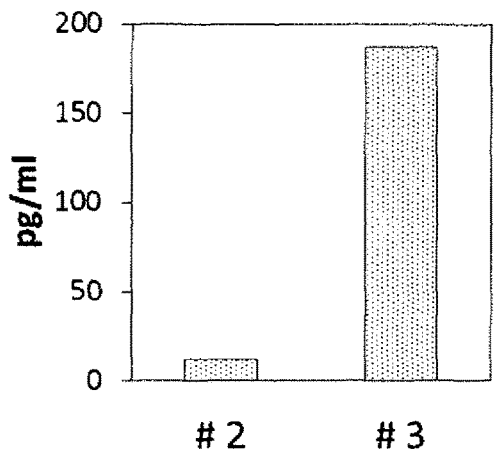
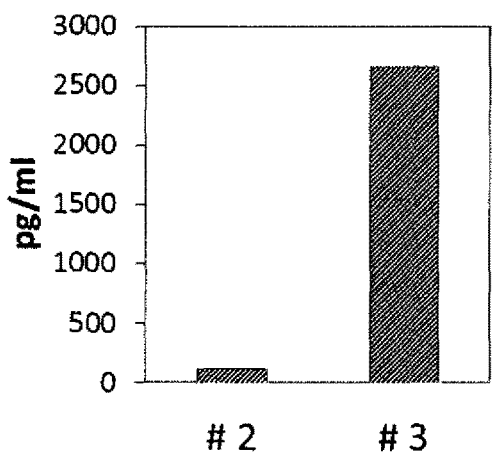
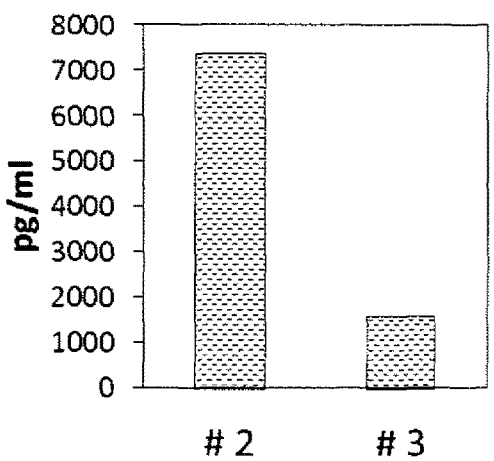

Figure 29:
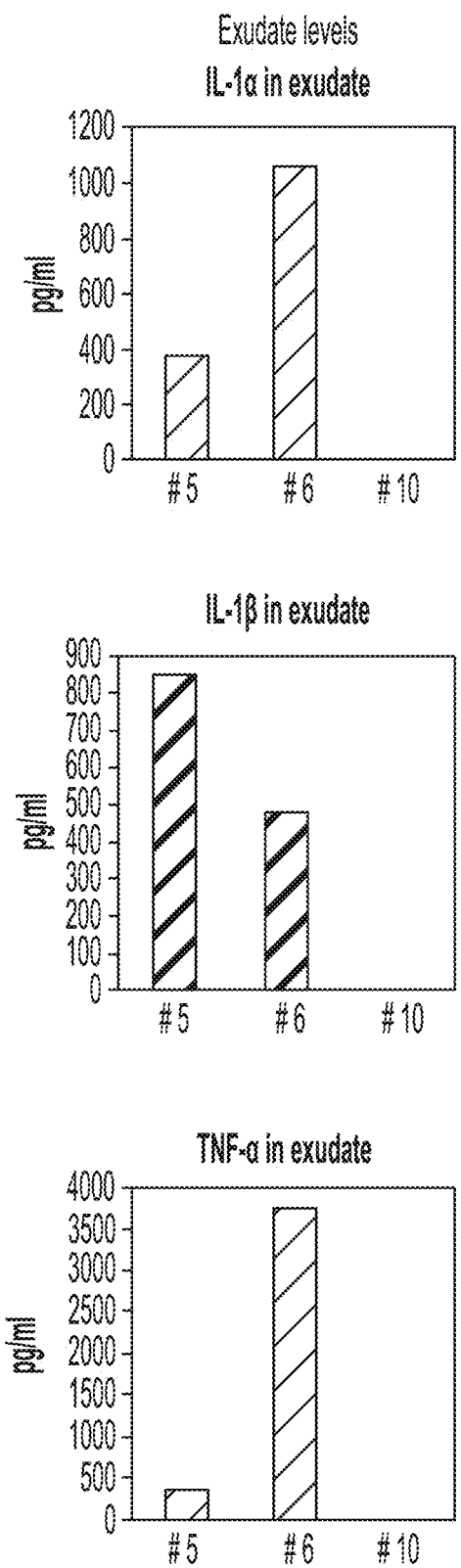

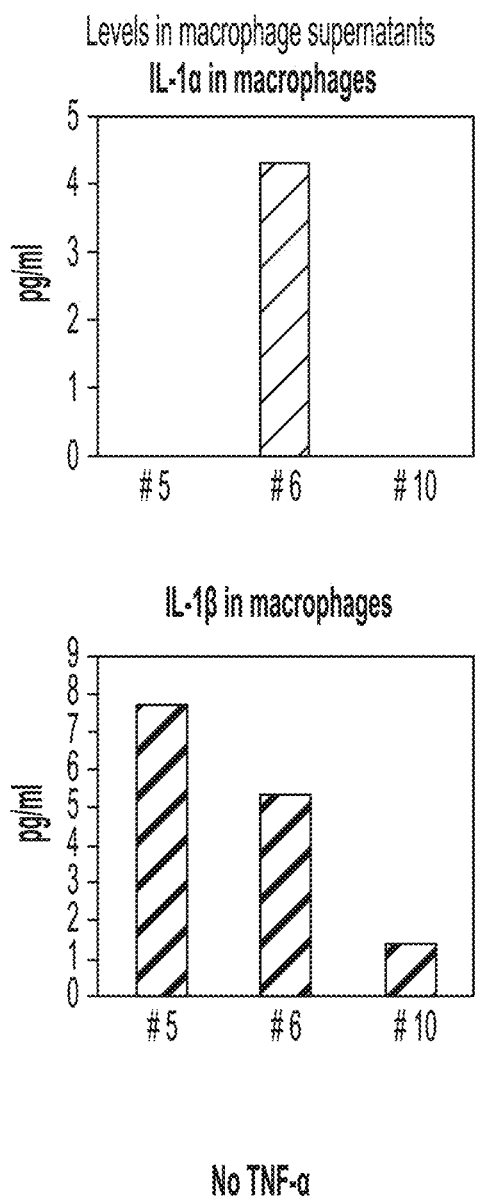
Figure 29 (ctd.)

Exudate levels

Figure 32:
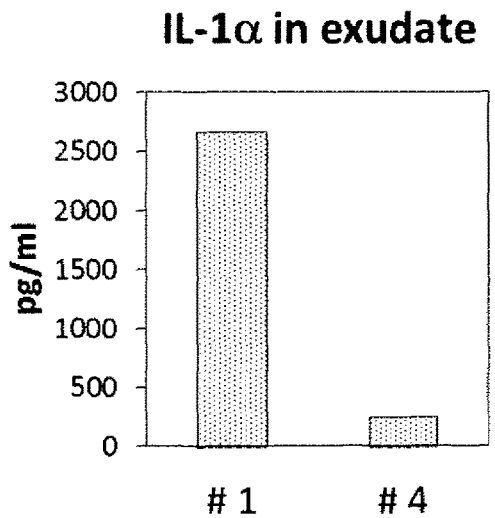
Figure 32:
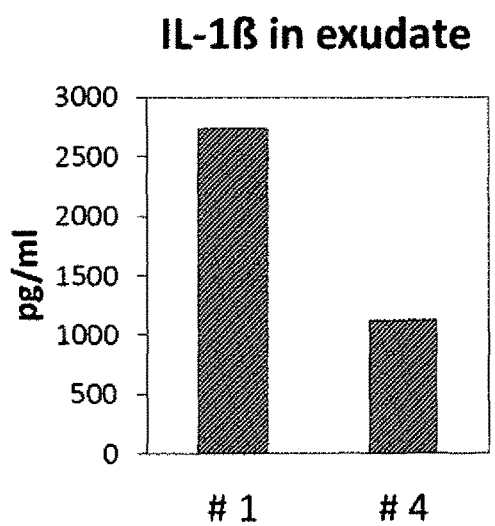
Figure 32:
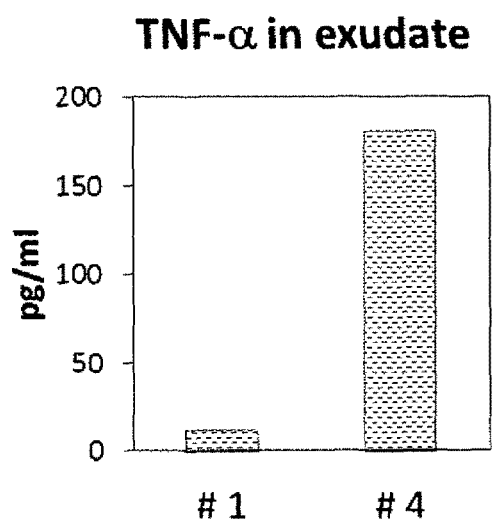

Figure 32 (ctd.)
Levels in macrophage supernatants
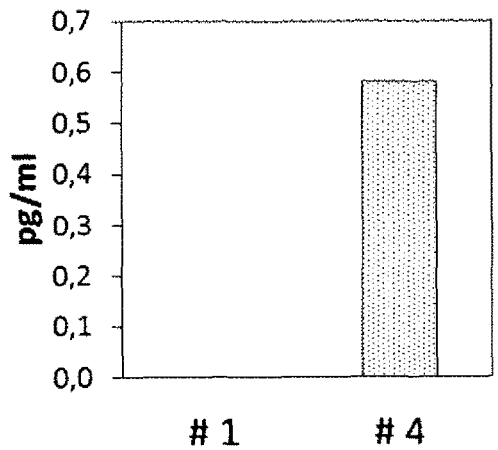
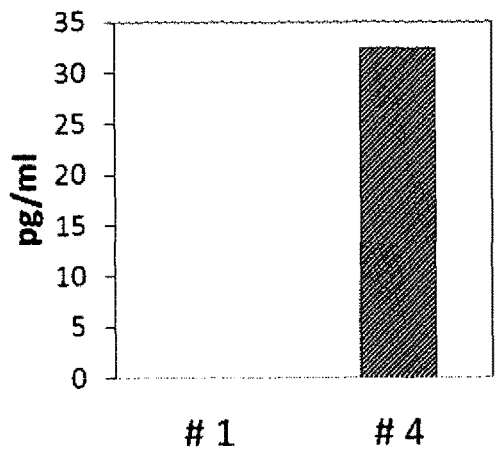
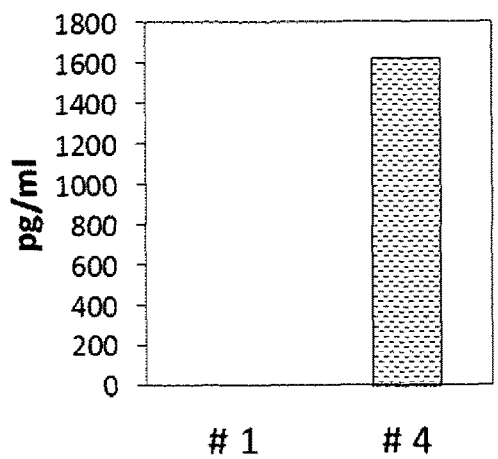

METHODS FOR IDENTIFYING A NON-HEALING SKIN WOUND AND FOR MONITORING THE HEALING OF A SKIN WOUND

CROSS-REFERENCE TO RELATED APPLICATIONS

This application is a national stage application filed under 35 U.S.C. § 371, of International Patent Application No. PCT/EP2017/076983, filed Oct. 23, 2017, which claims the benefit of and priority to European Patent Application Number 16002266.1, filed Oct. 24, 2016, the entire contents of which is hereby expressly incorporated by reference herein.

The present invention relates to an in vitro method for identifying a skin wound in an individual as being a non-healing skin wound or healing skin wound, in vitro methods for monitoring the healing of a skin wound in an individual, methods for screening for compounds suitable for modulating skin wound healing, as well as kits related thereto.

Chronic wounds are a major health issue worldwide with 5.7 million affected patients in the US alone and an expected increase due to the aging population and growing incidence of metabolic diseases.

Chronic wounds have a multifactorial etiology and are dependent on different variables:
a) underlying disease, e.g. diabetes, arterial or venous insufficiency, b) pressure, c) age and nutritional status and d) microbial environment.

Chronic wounds are generally understood as those wounds that have not healed within 2 months. They are a major health issue worldwide. In developed countries, including the US and the EU, it has been estimated that 1 to 2% of the total population will experience a chronic wound during their lifetime [Gottrup F (2004) Am J Surg 187:38S-43S]. In the US alone, approximately 5.7 million patients are affected. This number is expected to increase due to the aging population and growing incidence of metabolic diseases.

The major chronic wound indications are venous ulcers, pressure ulcers and diabetic foot ulcers. Venous ulcers are defects in pathologically altered tissue on the lower leg based on chronic venous insufficiency, often accompanied by deep venous thrombosis. Pressure ulcers are the results of severe tissue hypoxemia in immobilized patients. Diabetic foot ulceration can affect up to 25% of patients with diabetes throughout their lifetime and often results in lower limb amputation. The standard of care for all of these wounds, as recommended by the German Society for Dermatology [Dissemond J et al (2014) JDDG 1610-0379/2014/1207: 541-554] includes wound dressings, surgical and biological (maggot) debridement, infection control and negative pressure therapy. Regranex® (PDGF: platelet-derived growth factor) is the only registered pharmacological treatment, but its therapeutic efficacy is minor, as is the success of cell-based therapies. Recurrence is a problem in one third of all chronic wounds, regardless of their treatment.

Even though they are anti-inflammatory in other settings, topical corticosteroids cannot be used because one of their side effects is actually delayed wound healing [Hengge U R (2006) J Am Acad Dermatol 54:1-15]. Non-steroidal anti-inflammatory drugs, e.g. ibuprofen, are only effective in ameliorating wound pain [Dissemond j et al (2014)].

However, it is very often difficult to assess whether a skin wound in an individual is or develops into a non-healing, chronic wound and/or whether the healing of a skin wound improves or worsens in future.

Figure 8:
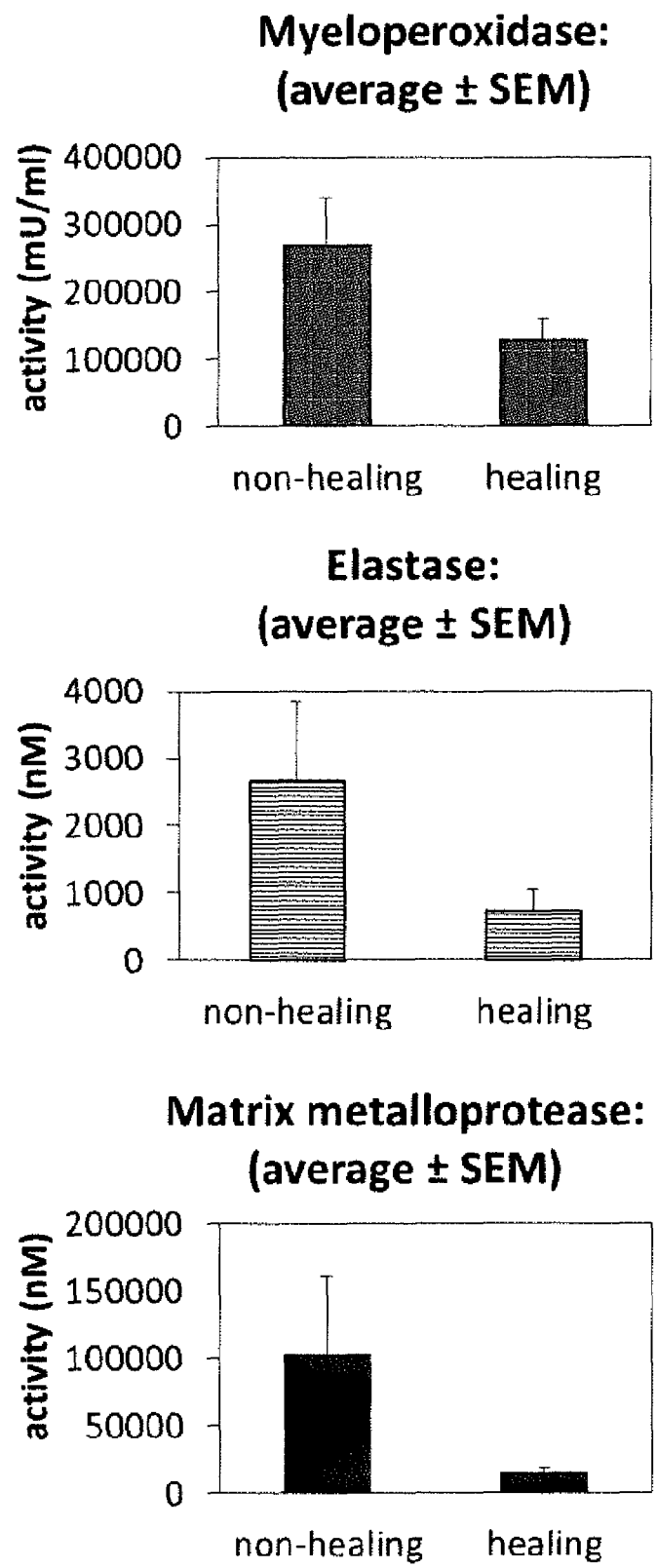
Figure 9:
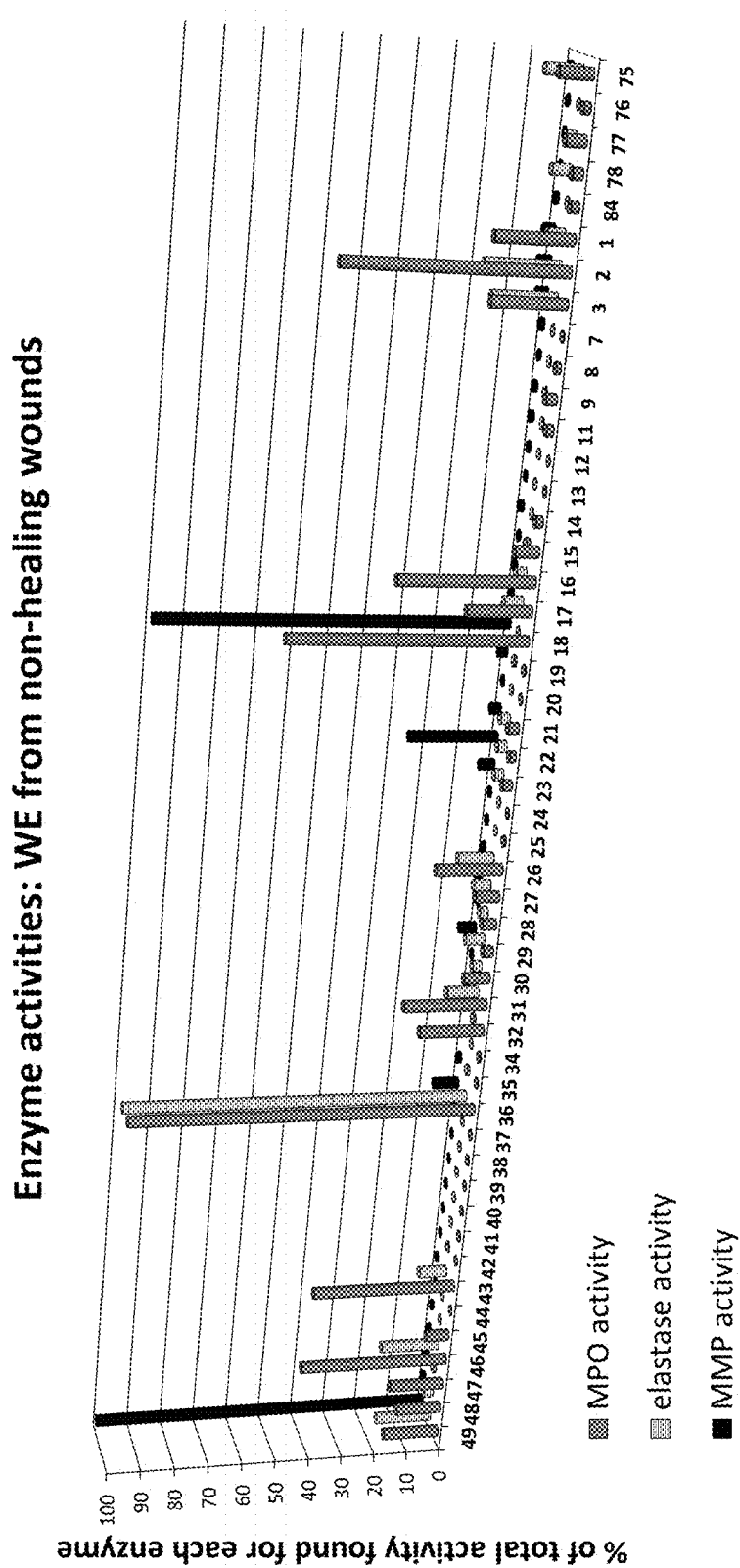
Figure 10:
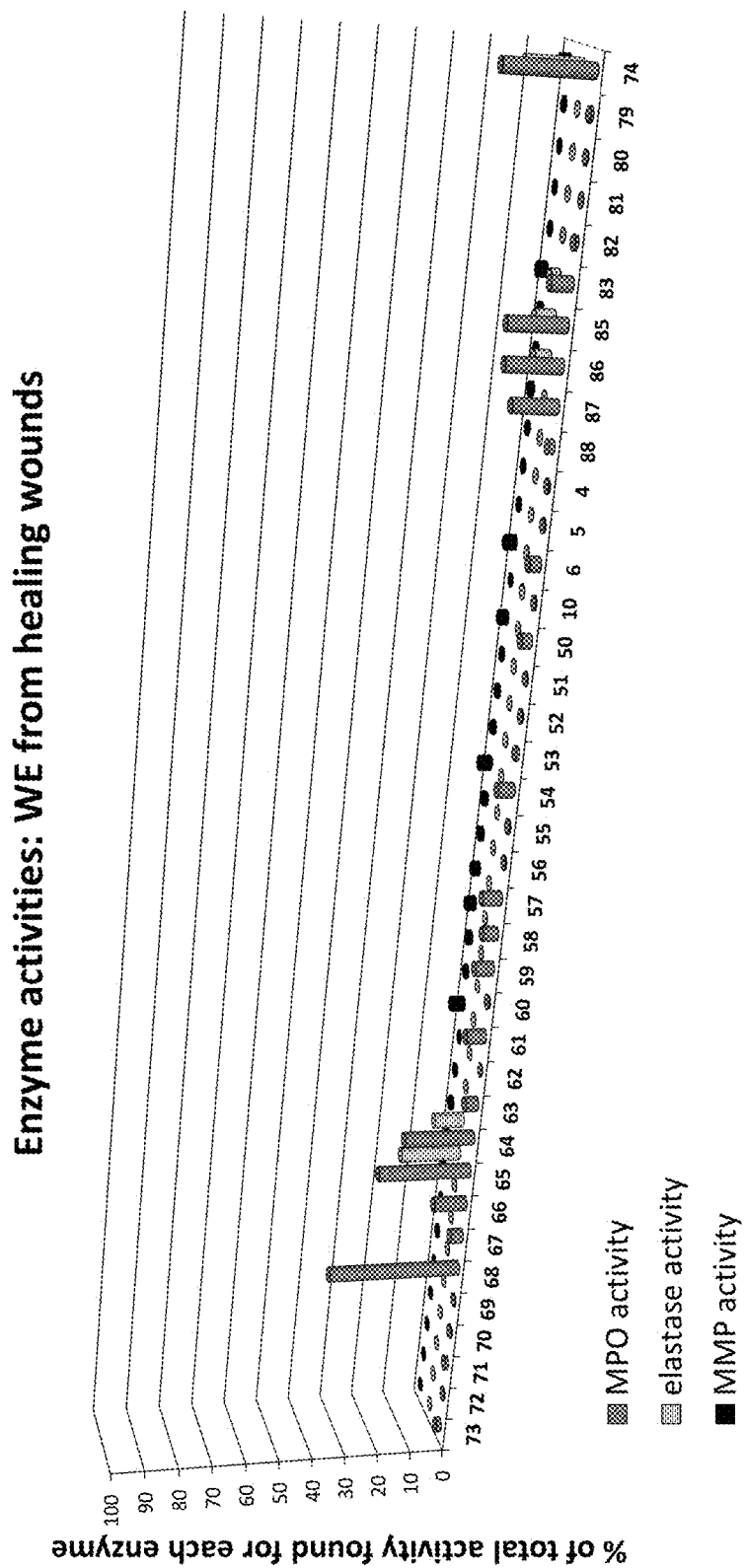
Figure 11:
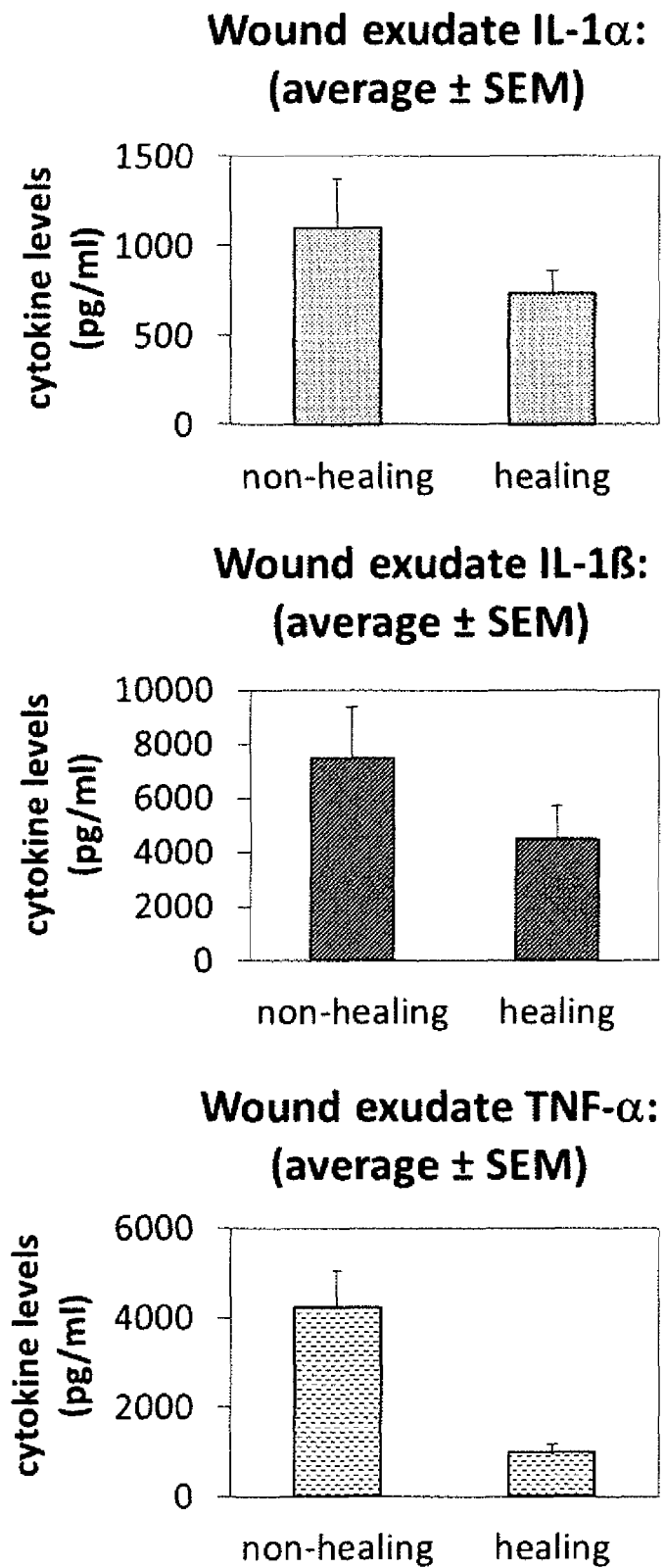
Figure 15:

A plurality of markers is known in the context of wound healing. Furthermore, it has been described in the past for certain markers, that some markers are elevated or decreased in groups of non-healing wounds in general (either pooled or separately, determining average values) as compared to healing wounds in general (again either pooled or separately, determining average values). However, when analyzing individual wound samples, the absolute values of such markers in single individuals often vary tremendously and do not allow for monitoring or diagnosing a single skin wound in a single individual reliably. As an example, Myeloperoxidase, Matrix-Metalloproteinase and Elastase enzyme activities are found to be generally lower in healing skin wound exudates as compared to the non-healing wounds. However, the variability of the enzyme levels determined in the individual wound exudate sample is very high and therefore do not allow as such for a reliable identification of non-healing skin wounds (FIGS. 8 to 10). Furthermore, IL-1α, IL-1β and TNF-α cytokine levels are elevated in general in non-healing skin as compared to healing skin wounds (FIG. 11). However, the individual values again vary strongly. For example, cytokine levels are in the same range as in non-healing wound exudates for some of the healing wound exudates (FIG. 13), and only about 50% of the wound exudate samples from non-healing wounds induce cytokine secretion by macrophages (FIG. 15).

Methods for reliably identifying non-healing skin wounds and/or for identifying that the healing of a skin wound worsens would provide an opportunity to further treat such skin wounds in time for the individual affected, thereby avoiding or attenuating recurrence and/or worsening of the healing status.

Therefore, there is a need for methods, kits and devices allowing for accurate diagnosis and monitoring of non-healing skin wounds in an individual, as well as methods which allow for predicting the wound healing of skin wounds in an individual, in order to prevent recurrence.

After skin injury, a complex biological process is initiated, leading to the activation and synchronization of multiple biological pathways. The classical stages of wound healing include inflammation, new tissue formation and tissue remodeling [reviewed in Gurtner G G et al (2008) Nature 453:314-321] and involve the contribution of a variety of cell types, as shown in FIG. 1.

When underlying pathology, e.g. diabetes, venous insufficiency or arterial occlusion, or microbial infection interrupts the physiological wound healing process, a failure to heal occurs, often leading to a chronic wound (ulcer). In chronic wounds, the inflammatory phase of the wound healing process is perpetuated, and the wounds do not progress to the stages of tissue regeneration and remodeling. In this case, pathogenic phagocytes release a variety of factors, including cytokines, proteases and toxic oxygen radicals into the wound tissue to destroy tissue cells, extracellular matrix and growth factors [Clark R A F et al (2007) J Invest Dermatol 127:1018-1029]. These pathogenic factors are contained in the wound itself, e.g. in the fibrin clot or in the wound exudate (wound fluid).

The wound fluid, called wound exudate (WE), is the extracellular fluid containing a molecular fingerprint of wound cells and can be referred to as a "liquid biopsy". Alternatively, a wound biofilm may be used.

Our unique entry point takes advantage of the fact that the pathogenic drivers of wound chronicity are contained in patient material. Using this patient material, we established and developed in vitro cellular methods using different cell types involved in the wound healing process. Wound exudates of poorly healing wounds have negative effects in these methods.

Surprisingly, the methods developed and established are particularly suitable for the identifying a skin wound in an individual as healing or non-healing skin wound, and/or for monitoring the healing of a skin wound in an individual and/or for evaluating the efficacy of known and unknown compounds, and/or for compound screening, in the context of skin would healing.

In one embodiment, the present invention relates to an in vitro method for identifying a skin wound in an individual as being a non-healing skin wound or healing skin wound, the method comprising:
a) measuring
  i) the proliferation of primary fibroblast cells in the presence of a wound exudate sample obtained from said skin wound, and/or
  ii) the fibroblast-derived matrix formation by primary fibroblast cells in the presence of a wound exudate sample or wound biofilm sample obtained from said skin wound, and
b) identifying the skin wound as being a non-healing skin wound in case the value(s) obtained in i) and/or ii) is/are below a control value established in the absence of wound exudate or wound biofilm, or
  identifying the skin wound as being a healing skin wound in case the value(s) obtained in i) and/or ii) is/are equal to or above a control value established in the absence of wound exudate or wound biofilm,
  preferably wherein the value(s) in a) is/are measured at least in triplicate and/or a statistical significance is established.

In one preferred embodiment of the present invention, the sample is a wound exudate sample. In another preferred embodiment, the sample is a wound biofilm sample. In a more preferred embodiment, the sample is a wound exudate sample.

It is known that different skin wounds of the same individual may exhibit a different healing. For example, one skin wound may be a healing skin wound, whereas another skin wound of the same individual at the same or a different time point may be a non-healing skin wound, e.g. due to infections or an underlying disease affecting a specific skin wound.

As shown in the examples, the present invention relates to an in vitro method which allows for identifying a skin wound in an individual as being a non-healing skin wound or healing skin wound. Therefore, the present invention allows, for example, for assessing specifically different skin wounds of the same individual.

Identifying a skin wound of an individual as a non-healing skin wound allows for patient surveillance, monitoring of the wound healing and specific therapeutic interventions to stabilize, ameliorate and/or improve the healing of the skin wound. For example, the skin wound identified as non-healing skin wound using a method of the invention may be treated with one or more of the following: compression, wound dressings, surgical debridement, biological debridement, infection control, antibiotic therapy, negative pressure therapy, proteins, in particular growth factors, antibodies, peptides, sugars, cells or cell constituents, artificial skin, human blood-derived products, gene therapy or genetically engineered wound bed modifications, drugs, herbal medicines, plant extracts.

A "wound" is understood as damage to a tissue of a living individual, such as cuts, tears, burns, or breaks, preferably a wound is understood as open injury of a tissue of a living individual.

The present invention relates to methods and related subject-matter suitable for skin wounds. Accordingly, a "skin wound" is understood as a damage to a skin of a living individual, such as cuts, tears, burns, or breaks. Preferably, a skin wound is understood as open injury of the skin of a living individual. The skin may be located at any area of an individual, such as for example the head, the arms, the legs, the chest, or the back. Further, the individual may have one, two, three, four or more skin wounds. Further, the area of a skin wound may differ. In a preferred embodiment, the skin wound forms wound exudate. In another preferred embodiment, the skin wound forms a wound biofilm. The skin wound may for example be selected from a wound of a diabetic patient, a wound which is infected by at least one microorganism, an ischemic wound, a wound in a patient suffering from deficient blood supply or venous stasis, an ulcer, such a diabetic ulcer, venous ulcer, arterial ulcer (e.g. ulcus cruris arteriosum), mixed ulcer, or pressure ulcer, a neuropathic wound, ulcus cruris, surgical wound, burn, dehiscence, neoplastic ulcer and rare ulcer. In order to increase reliability of the present methods, an individual's skin wound is not affected by a further disease mechanically preventing wound closure, such as calcinosis, where calcium crystals in the wound mechanically prevent wound closure, or exudative dermatitis.

An ulcer is understood as a sore on the skin, accompanied by the disintegration of tissue. Ulcers can result in complete loss of the epidermis and often portions of the dermis and even subcutaneous fat.

As used herein, a "non-healing skin wound" refers to a skin wound which does not heal at an expected rate, in particular, as a skin wound which does not close within 2 months under standard therapy, preferably within 3 or more months under standard therapy. Preferably, a non-healing skin wound is characterized by a lack of wound closure, an increase of the area and/or depth of the wound, necrosis and/or infections of the skin wound, and/or lack of granulation.

As used herein, a "healing skin wound" is understood as a skin wound which heals at an expected rate, in particular, as a skin wound which closes within 2 months under standard therapy. Preferably, a healing skin wound is characterized by ongoing wound closure, granulation, absence of necrosis and/or absence of infections.

"Standard therapy" is understood as a treatment recommended in general by physicians for skin wounds, in particular one or more selected from wound dressings, surgical and biological (maggot) debridement, infection control, negative pressure therapy, and therapy with a biological or cell treatment.

In another preferred embodiment of a method of the invention described herein, the skin wound is untreated or treated with standard therapy or with one or more of the following: compression, wound dressings, surgical debridement, biological debridement, infection control, antibiotic therapy, negative pressure therapy, proteins, in particular growth factors, antibodies, peptides, sugars, cells or cell constituents, artificial skin, human blood-derived products, gene therapy or genetically engineered wound bed modifications, drugs, herbal medicines, plant extracts.

The individual is an animal, preferably the individual is a vertebrate, in particular a mammal, more preferably a human. The individual may be an otherwise healthy individual or may exhibit further diseases and/or co-morbidities, and/or is treated with medication(s) for further diseases and/or co-morbidities. Further, the skin wound of the individual may be untreated or treated with standard therapy or with one or more of the following: compression, wound dressings, surgical debridement, biological debridement, infection control, antibiotic therapy, negative pressure therapy, proteins, in particular growth factors, antibodies, peptides, sugars, cells or cell constituents, artificial skin, human blood-derived products, gene therapy or genetically engineered wound bed modifications, drugs, herbal medicines, plant extracts.

In step a), the method of the invention includes measuring
i) the proliferation of primary fibroblast cells in the presence of a wound exudate sample or wound biofilm sample obtained from said skin wound, and/or
ii) the fibroblast-derived matrix formation by primary fibroblast cells in the presence of a wound exudate sample or wound biofilm sample obtained from said skin wound.

In one preferred embodiment of the present invention, the sample is a wound exudate sample. In another preferred embodiment, the sample is a wound biofilm sample. In a more preferred embodiment, the sample is a wound exudate sample.

Measuring the proliferation of primary fibroblast cells in the presence of a wound exudate sample or wound biofilm sample obtained from said skin wound may be performed as shown in the examples, in particular in Example 3.1.1. For the method, primary fibroblast cells are used, which may be primary mammal dermal fibroblasts, preferably primary human dermal fibroblasts. Methods for obtaining cultured primary human dermal fibroblast cells are known in the art and are for example described in the examples. For example, the cells may be cultured using DMEM medium containing FCS. In a further preferred embodiment, the cells are incubated on a solid support, thereby allowing the cells to adhere to the support, as for example described in the Examples, where multiwell plates were used. Further, the cells are contacted with the wound exudate sample or wound biofilm sample, which is optionally diluted, e.g. diluted with medium or a saline aqueous liquid. The contacting may be performed before or after adherence of the cells occurs. For example, the contacting may be achieved by adding the optionally diluted, liquid wound exudate sample or wound biofilm sample, to the cells either prior to adherence, for example at the seeding of the cells, or after adherence. The contacting may be achieved e.g. by pipetting, and optionally gentle mixing. The cells are incubated for an appropriate time, such as for 6 hours to 300 hours, more preferably 12 hours to 200 hours, even more preferably 24 hours to 120 hours. In the examples, 72 hours were successfully used. For negative control samples without wound exudate or wound biofilm sample, a corresponding liquid without wound exudate or wound biofilm, such as medium or a saline aqueous liquid may be added or no liquid is added. Subsequently, the amount, preferably the cell number, including the formation of extracellular matrix, of the primary fibroblast cells is determined, such as by fixing cells and determining total protein content. The cells may for example be fixed using paraformaldehyde. Further, a suitable dye, such as sulforhodamine B may be used for determining the amount, preferably the cell number, including the formation of extracellular matrix, of the primary fibroblast cells. The stained cells including the extracellular matrix formed may then be quantified e.g. by determining absorbance or fluorescence at a suitable wavelength, depending on the dye. Preferably, the method is performed in 2D cell culture, which allows for culturing the cells adherently on a solid support. In a preferred embodiment, the sample is a wound exudate sample.

Preferably, the method step includes the following steps:
(i) culturing primary human dermal fibroblast cells,
(ii) incubating the cells on a solid support, thereby allowing the cells to adhere to the support,
(iii) contacting the cells with the wound exudate sample or wound biofilm sample, which is optionally diluted, wherein the contacting may be performed before or after adherence of the cells occurs,
(iv) determining the amount, preferably the cell number, including the formation of extracellular matrix, of the primary fibroblast cells, such as by fixing cells and determining total protein content,
preferably wherein the method is performed in 2D cell culture.

In one preferred embodiment of the present invention, the sample is a wound exudate sample. In another preferred embodiment, the sample is a wound biofilm sample. In a more preferred embodiment, the sample is a wound exudate sample.

The culturing of cells in methods of the present invention is preferably performed at about 20° C. to 40° C., more preferably 25° C. to 38° C., even more preferably at about 37° C.

Measuring the fibroblast-derived matrix formation by primary fibroblast cells in the presence of a wound exudate sample or wound biofilm sample obtained from a skin wound may be performed as shown in the examples, in particular in Example 3.1.2. For the method, primary fibroblast cells are used, which may be primary mammal dermal fibroblasts, preferably primary human dermal fibroblasts. In the examples, primary human dermal fibroblast cells are seeded on a support, which is preferably pre-coated with an adhesion enhancing agent, such as gelatin. For example, the coating may be achieved by incubating the support with a solution or suspension containing the adhesion enhancing agent, such as gelatin. In the examples, a 0.2% gelatin solution was successfully used. Preferably, the cells are cultured until confluence is reached. Subsequently, the cells are contacted with (i) a matrix promoting supplement, and (ii) the wound exudate sample or wound biofilm, which is optionally diluted, wherein (i) and (ii) may be contacted simultaneously or sequentially. For example, the matrix promoting supplement, which is preferably selected from a solution comprising Vitamin C or a physiologically acceptable salt thereof, such the sodium salt, or 2-phospho-L-ascorbic acid or a physiologically acceptable salt thereof, and a combination of EGF and insulin, is added to the cells, e.g. by pipetting, and optionally gentle mixing. The wound exudate sample or wound biofilm sample, which is optionally diluted, may be contacted simultaneously or sequentially. For example, the optionally diluted wound exudate sample or wound biofilm sample may be mixed with the matrix promoting supplement, and the mixture may be added to the cells. Alternatively, the optionally diluted wound exudate sample or wound biofilm sample may be added separately, but simultaneously, or separately, but subsequent to or prior to the matrix promoting supplement. In case of subsequent non-simultaneous contacting, the components (i) and (ii) are preferably contacted within 1 hour. The cells are subsequently incubated, preferably for 12 hours to 20 days, wherein the medium is optionally replaced at least one time with fresh medium supplemented with optionally diluted wound exudate or wound biofilm and matrix promoting supplement. In the example, the medium was replaced once after 4 days of incubation, and the total incubation was 8 days. As a 3-dimensional fibroblast-derived matrix is formed, the solid support preferably contains at least one cavity which allows for filling of the space and therefore allows for a 3D cell culture. Subsequently, the amount of the fibroblast-derived matrix is determined, such as by fixing cells and determining total protein content. The cells may for example be fixed using paraformaldehyde. Further, a suitable dye, such as sulforhodamine B may be used for determining the amount, preferably the cell number, including the formation of extracellular matrix, of the primary fibroblast cells. The stained cells including the formation of extracellular matrix may then be quantified e.g. by determining absorbance or fluorescence at a suitable wavelength, depending on the dye.

Accordingly, the method step preferably includes the following steps:
(i) seeding primary human dermal fibroblast cells on a support, which is preferably pre-coated with an adhesion enhancing agent, such as gelatin,
(ii) culturing the cells on the support, preferably until confluence is reached,
(iii) contacting the cells with (i) a matrix promoting supplement, and (ii) the wound exudate sample or wound biofilm sample, which is optionally diluted, wherein (i) and (ii) may be contacted simultaneously or sequentially,
(iv) determining the amount of the fibroblast-derived matrix, such as by fixing cells and determining total protein content,
preferably wherein the method is performed in 3D cell culture.

In one preferred embodiment of the present invention, the sample is a wound exudate sample. In another preferred embodiment, the sample is a wound biofilm sample. In a more preferred embodiment, the sample is a wound exudate sample.

The "fibroblast-derived matrix" or "FDM" is understood as the extracellular matrix (ECM) formed by living fibroblast cells in an environment conducive for matrix formation, e.g. in the presence of a matrix promoting supplement. FDM is obtainable as described in the examples. In particular, FDM is obtainable by (i) seeding primary human dermal fibroblast cells on a support, which is pre-coated with an adhesion enhancing agent, such as gelatin, (ii) culturing the cells on the support, preferably until confluence is reached and (iii) contacting the cells with a matrix promoting supplement, such as Vitamin C or a physiologically acceptable salt thereof, or 2-phospho-L-ascorbic acid or a physiologically acceptable salt thereof, or a combination of EGF and insulin.

A "matrix promoting supplement" is understood as a compound or composition which promotes the formation of fibroblast-derived matrix by living fibroblast cells in an in vitro cell culture. Suitable matrix promoting supplements are Vitamin C or a physiologically acceptable salt thereof, such the sodium salt, or 2-phospho-L-ascorbic acid or a physiologically acceptable salt thereof, and a combination of EGF and insulin, as well as compositions comprising the compounds, such as solutions or suspensions. A combination of EGF and insulin may be provided to the cell culture separately, e.g. as separate solutions comprising EGF or insulin respectively, or together, e.g. as solution comprising EGF and insulin.

An "adhesion enhancing agent" is an agent which enhances adhesion of cells to a solid support, such as a plastic support, but which does not substantially interfere with the viability of the cells. In a preferred embodiment, the adhesion enhancing agent is gelatin or fibronectin, more preferably gelatin.

"2D cell culture" is understood as a cell culture wherein the cells are cultured in a planar or substantially planar surface. In a preferred embodiment, the 2D cell culture is culturing of adherent cells.

"3D cell culture" is understood as a cell culture wherein the cells are cultured on a non-planar or substantially non-planar surface. In a preferred embodiment, the 3D cell culture is culturing of adherent cells and/or culturing of cells within a matrix, such as ECM, in particular FDM.

A "support" or "solid support" is preferably selected from a chip, array, such as a microarray or nanoarray, a plate, such as a multiwell plate, or a dish. For cell culture applications, the solid support is preferably suitable for culturing cells, for example the support may be a plastic support.

"Wound exudate" is understood as the extracellular fluid located within and above a skin wound. The wound exudate is also referred to a "liquid biopsy".

"Wound biofilm" is understood as substance, resulting from an infection of a skin wound by micro-organisms that are capable of forming colonies. Typically, the wound biofilm is a gummy substance. A wound biofilm comprises microbial species selected from bacteria, fungi, yeasts, algae and other micro-organisms, and cellular debris. A wound biofilm is formed when certain types of micro-organisms attach themselves to the surface of skin wounds by secreting a gummy substance. For example, a wound biofilm sample may be obtained by surgical sharp debridement of the wound surface or by wiping of the wound surface with a cotton swab or wound dressing material.

A "wound exudate sample" or "WE" is understood as a sample of wound exudate obtained from a skin wound of an individual. Methods for obtaining a wound exudate sample are known in the art. For example, a wound exudate sample may be obtained by a physical or chemical method, in particular by applying negative pressure to the skin wound, such as by using a negative pressure drainage device, a method using capillary forces, collecting wound exudate in a film dressing or membrane, collecting wound exudate in a syringe, applying an absorptive material, such as absorptive beads, or a filter, or by using a swab, such as a cotton swab, in particular wherein the film dressing or membrane is a cellulose layer and/or wherein the absorptive material is a cellulose layer. Preferred suitable cellulose layers are nanocellulose layers, such as nanocellulose layers marketed as biocellic+ and epicite+. Such layers, including their production, are described in WO 2013/060321, WO 2016/113400 and/or WO2017/089005. The volume of wound exudate sample may vary and may be in the range of 1 nl to 1 l, 10 nl to 10 1 l, or 100 nl to 1 l, such as 1 µl to 1 l, 1 ml to 1 l or 10 ml to 1 l. For example, wound exudate samples investigated in the examples had a volume of up to 400 ml and typically had a volume of 10 to 100 ml, in particular 10 to 50 ml. The wound exudate sample may be used the methods of the invention directly after obtaining the sample or may be stored, in particular stored at <4° C., <0° C. or <10° C. before usage in the methods of the invention.

Preferred cellulose layers which can be used for obtaining a wound exudate are nanocellulose layers, in particular those marketed as biocellic+ and epicite+. Such particularly preferred cellulose layers are described in WO 2013/060321, WO 2016/113400 and/or WO2017/089005. It is therefore explicitly referred to the disclosure of nanocellulose layers and their production in WO 2013/060321, WO 2016/113400 and/or WO2017/089005. Nanocellulose is generally understood as a term referring to nano-structured cellulose. Nanocellulose or nano-structured cellulose comprises cellulose nanofibers (CNF), also called microfibrillated cellulose (MFC), nanocrystalline cellulose (NCC or CNC), and bacterial nanocellulose. Bacterial nanocellulose is understood as nano-structured cellulose produced by bacteria.

In particular, WO2017/089005 discloses a nano-structured cellulose (BNC)-containing article, wherein the article comprises BNC in an amount of at least 1 by weight and at most 15% by weight, comprises fluid in an amount of at least 85% by weight and at most 99% by weight, has an average thickness of at least 0.5 mm and at most 8 mm, wherein the BNC is of microbial origin.

Preferably, the article has an average thickness of at most 6 mm, preferably at most 5 mm. Preferably, the weight-average molecular weight Mw of the BNC of the article, is at most 1,500,000 g/mol, preferably at most 1,200,000 g/mol, at most 1,000,000 g/mol, at most 900,000 g/mol, at most 850,000 g/mol, at most 800,000 g/mol, most preferably at most 780,000 g/mol. Preferably, the BNC of the article, comprises carbonyl groups in an amount of less than 8.5 µmol/g, preferably of less than 8.0 µmol/g, of less than 7.5 µmol/g, of less than 7.0 µmol/g, of less than 6.0 µmol/g, more preferably of less than 5.75 µmol/g. Preferably, the polydispersity index (Mw/Mn) of the of the article is less than 3.5, preferably less than 3.0, more preferably less than 2.75 and/or more than 2.5. Preferably, the article has a tensile strength of more than 252 MPa, preferably more than 275 MPa, more preferable more than 300 MPa, and most preferably of more than 310 MPa. Further, WO2017/089005 discloses a method for producing such cellulose layers and it is hereby explicitly referred to WO2017/089005 for methods for producing such cellulose layers. In particular, discloses a method of manufacturing a cellulose-containing article, wherein the method comprises at least the steps of: a) providing biotechnologically produced nanostructured cellulose (BNC) in a semi-static continuous process, b) providing the article, and c) optionally, sterilizing the article.

WO 2016/113400 discloses a multi-phase biomaterial, comprising bacterially synthesized nanocellulose (BNC) comprising at least two different bacterial cellulose networks, having a thickness more than 2 mm, wherein said BNC is transparent. Preferably, said BNC is transparent up to a thickness of about 3 mm. Preferably, said BNC is transparent up to a thickness of about 5 mm. Preferably, said BNC has solids content of at least 1 or at least 2%. Preferably, said BNC has a tensile strength of at least 0.1 MPa. Preferably, said BNC has a water absorption capacity (WAC) of at least 80%. Preferably, said BNC has a moist vapor transmission rate in the wet state of at least 100 g/(m$^2$*24 h). Preferably, an average cross sectional pore area of a first BNC network is higher by a factor of at least 1.2 than for a second BNC network Preferably, at least one BNC network has a degree of polymerization of at least 400 Preferably, the degree of polymerization of the BNC network with the highest degree of polymerization is higher by a factor of at least 2 as compared to the degree of polymerization of the BNC network with the lowest degree of polymerization in the multi-phase biomaterial. WO 2016/113400 discloses a method for producing multi-phase biomaterials comprised of bacterially synthesized nanocellulose (BNC), comprising inoculating a culture medium with at least two different cellulose-producing bacterial strains, which have been commonly or separately prepared, thereby to synthesize BNC comprised of a plurality of different bacterial cellulose networks wherein BNC structure and BNC properties of the multi-phase biomaterials are predetermined by selection of the at least two different bacterial strains, by their preparation and inoculation and by selection of conditions of the synthesis. Preferably, the quotient of the initial kinetics of cellulose production of the strain with the faster initial kinetics (dividend) and the initial kinetics of cellulose production of the strain with the slower initial kinetics (divisor) is at most 2. Preferably, the multi-phase biomaterial is grown to a thickness of more than 2 mm. Preferably, the culture medium comprises a carbon source in an amount of at least 10 g/l based on the volume of the culture medium. Preferably, the inoculation ratio of one different cellulose-producing strains is at most 90:10.

WO 2013/060321 discloses a method for generating dried cellulose and cellulose-containing material, in which the cellulose or the cellulose-containing material for the purpose of drying and preserving the swellability with almost complete reconstitution of the cellulose structure and consistency is subjected to the adsorbent effect of a moisture binder and after this adsorbent exposure is dried regardless of any structural change to the material. Preferably, as the moisture binder an osmotically and/or hygroscopically effective solution is used containing in particular single saccharides, salts, saccharide-containing or saccharide-like substances, polyethylene oxides, a combination of different representatives of these moisture-binding groups of substances and/or a combination of one and/or more representatives of these moisture-binding groups of substances with one or more surfactants and/or one or more preservatives. Preferably, for further modification of the reswelling behavior in addition to the moisture binder, a surfactant and/or preservative-containing solution is used. Preferably, the moisture-binding solution has a concentration of osmotically active and/or hygroscopic substances of 0.01% up to the saturation limit, preferably of 5-20%. Preferably, the surfactants and/or preservatives which are used in combination with the osmotically and/or hygroscopically effective solution are used in a concentration of 0.01% up to the saturation limit, preferably of 0.01-10%. Preferably, the cellulose or the cellulose-containing material being treated with the moisture binder is air-dried. Preferably, the cellulose or the cellulose-containing material being treated with the moisture binder is vacuum-dried. Preferably, the cellulose or the cellulose-containing material to be subjected to the adsorbent effect of the moisture-binding solution is dipped into the moisture-binding solution. Preferably, onto the cellulose or the cellulose-containing material to be subjected to the adsorbent effect of the moisture-binding solution, the moisture-binding solution is sprayed, dropped, brushed or cast. Preferably, the moisture binder is already added in addition to the cellulose cultivation process for the purpose of its adsorbent exposure. Further disclosed is a suitable dried cellulose and dried cellulose-containing material, characterized in that the structure of the cellulose or the cellulose-containing material comprises adsorbed osmotically and/or hygroscopically active substances of a dried moisture binder for the purpose of its swellability with almost complete reconstitution of the original cellulose structure and consistency.

The nanocellulose layer which can be used according to the invention may be a nanocellulose membrane or dressing, which is optionally covered, and which may have e.g. a disc-like form. Accordingly, the cellulose layer or nanocellulose layer is in one preferred embodiment a cellulose disc or nanocellulose disc. Typically, the nanocellulose surface area brought into contact with wound exudate is in the range of about 1 cm$^2$ to about 100 cm$^2$.

A "wound biofilm sample" or "WB" is understood as a sample of wound biofilm obtained from a skin wound of an individual. Methods for obtaining a wound biofilm sample are known in the art. For example, a wound biofilm sample may be obtained by surgical sharp debridement or by wiping of the wound surface with a cotton swab or wound dressing material. The volume of wound biofilm sample may vary and may be in the range of 1 nl to 1 l, 10 nl to 1 l, or 100 nl to 1 l, such as 1 µl to 1 l, 1 ml to 1 l or 10 ml to 1 l. The wet weight of wound biofilm may vary and may be in the range of 10 µg to 10 g, 100 µg to 10 g, such as 1 mg to 10 g, 10 mg to 10 g, 100 mg to 10 g, or 1 g to 10 g. The wound biofilm sample may be used the methods of the invention directly after obtaining the sample or may be stored, in particular stored at <4° C., <0° C. or <10° C. before usage in the methods of the invention.

It was surprisingly found that the above assays relating to measuring the proliferation of primary fibroblast cells and the fibroblast-derived matrix formation by primary fibroblast cells can reliably identify skin wounds as healing skin wounds, or non-healing skin wounds, respectively. In particular, it is possible to reliably identify skin wounds as non-healing skin wounds. Therefore, one or both of these assays may be used for the method of the invention. In particular, it was surprisingly found that the wound exudate of a healing wound has a dose-dependent positive effect on the proliferation of primary fibroblast cells and the fibroblast-derived matrix formation by primary fibroblast cells, as compared to a control in absence of wound exudate. Therefore, value(s) obtained in the assay(s) which is/are equal to or above a control value established in the absence of wound exudate are indicative of a healing wound. Accordingly, value(s) obtained in the assay(s) which is/are below a control value established in the absence of wound exudate are indicative of a non-healing wound.

The control value(s) may be determined in parallel or may be established independently, preferably in parallel.

Therefore, in step b) of the method of the invention, the skin wound is identified as being a non-healing skin wound in case the value(s) obtained in i) and/or ii) is/are below a control value established in the absence of wound exudate or wound biofilm, preferably at least 10% below the respective control value(s), more preferably at least 15%, even more preferably are at least 20% below the respective control value(s),
or the skin wound is identified as being a healing skin wound in case the value(s) obtained in i) and/or ii) is/are equal to or above a control value established in the absence of wound exudate or wound biofilm, at least 10% above the respective control value(s), more preferably at least 15%, even more preferably are at least 20% above the respective control value(s), more preferably wherein the value obtained in i) is at least 10%, more preferably at least 15%, above the respective control value and/or the value obtained in ii) is at least 50%, more preferably at least 100%, above the respective control value.

Further, it is preferred to perform the measurements at least in triplicate and/or to establish a statistical significance to improve the accuracy of the diagnosis. Statistical methods are known in the art. For example, the standard deviation may be determined. Further, the statistical significance may be $p \leq 0.05$, $p \leq 0.001$ or $p \leq 0.001$ for identifying a skin wound as a healing or non-healing skin wound.

Therefore, in a preferred embodiment, the value(s) in step a) is/are measured at least in triplicate and/or a statistical significance is established.

Moreover, it was found that the accuracy of the method is further improved in case both assays, measuring the proliferation of primary fibroblast cells and the fibroblast-derived matrix formation by primary fibroblast cells in the presence of a wound exudate sample, respectively, are performed. Accordingly, a skin wound can be identified reliably as a non-healing skin wound in case the values obtained in both assays are below a control value established in the absence of wound exudate or wound biofilm. Further, a skin wound can be identified reliably as a healing skin wound in case the values obtained in both assays are equal to or above a control value established in the absence of wound exudate or wound biofilm. In a more preferred embodiment, values in both assays which are each at least 10% above the respective control values, more preferably wherein the values obtained in the assay are each at least 15%, even more preferably are at least 20%, 30%, 40% or 50% above the respective control values are identifying the skin wound as healing skin wound. In a preferred embodiment, the sample is a wound exudate sample.

Accordingly, in another preferred embodiment, values in both assays which are each at least 10% below the respective control values, more preferably wherein the values obtained in the assay are each at least 15%, even more preferably are at least 20%, 30%, 40% or 50% below the respective control values are identifying the skin wound as non-healing skin wound. Thereby, the reliability and accuracy of the method of the invention can be further increased.

Therefore, in a preferred embodiment, the method of the invention comprises
a) measuring
   i) the proliferation of primary fibroblast cells in the presence of a wound exudate sample or wound biofilm sample obtained from said skin wound, and
   ii) the fibroblast-derived matrix formation by primary fibroblast cells in the presence of a wound exudate sample or wound biofilm sample obtained from said skin wound, and
b) identifying the skin wound as being a non-healing skin wound in case the value obtained in a)i) is below a control value established in the absence of wound exudate or wound biofilm, and the value obtained in a)ii) is below a control value established in the absence of wound exudate or wound biofilm, preferably wherein the values obtained in a)i) and a)ii) are at least 10% below the respective control values, more preferably wherein the values obtained in a)i) and a) ii) are at least 15%, even more preferably are at least 20% below the respective control values, or
identifying the skin wound as being a healing skin wound in case the value obtained in a)i) is equal to or above a control value established in the absence of wound exudate or wound biofilm, and the value obtained in a)ii) is equal to or above a control value established in the absence of wound exudate or wound biofilm,
preferably wherein the values obtained in a)i) and a)ii) are at least 10%, more preferably at least 15%, even more preferably are at least 20%, above the respective control value, more preferably wherein the value obtained in a)i) is at least 10%, more preferably at least 15%, above the respective control value and the value obtained in a)ii) is at least 50%, more preferably at least 100%, above the respective control value.
preferably wherein a combined value is established for the values obtained in a)i) and a)ii) and/or the values in a) are measured at least in triplicate and/or a statistical significance is established.

In one preferred embodiment of the present invention, the sample is a wound exudate sample. In another preferred embodiment, the sample is a wound biofilm sample. In a more preferred embodiment, the sample is a wound exudate sample.

Moreover, it was surprisingly found that the accuracy and reliability can be further increased by including a further assay in the method, which measures the proliferation of keratinocyte cells, such as primary keratinocyte cells or HaCaT cells. Further, it was found in the Examples that the use of HaCaT cells is to be preferred as compared to primary keratinocytes and allows for reliable prediction, in combination with the fibroblast-based assays described above. It was surprisingly found that a skin wound can be identified reliably as a healing skin wound in case at least two, preferably all three of the values obtained with the assays measuring the proliferation of primary fibroblast cells, measuring the fibroblast-derived matrix formation by primary fibroblast cells and measuring the proliferation of keratinocyte cells are equal to or above the respective control values established in the absence of wound exudate or wound biofilm, more preferably wherein the values obtained in the assays measuring the proliferation of primary fibroblast cells and/or the fibroblast-derived matrix formation by primary fibroblast cells, and the assay measuring the proliferation of keratinocyte cells are at least 10%, more preferably at least 15%, 20%, 30%, 40% or 50% above the respective control value.

Accordingly, it was found that a skin wound can be identified reliably as a non-healing skin wound in case at least two, preferably all three of the values obtained with the assays measuring the proliferation of primary fibroblast cells, measuring the fibroblast-derived matrix formation by primary fibroblast cells and measuring the proliferation of keratinocyte cells are below the respective control values established in the absence of wound exudate or wound biofilm, more preferably wherein the values obtained in the assays measuring the proliferation of primary fibroblast cells and/or the fibroblast-derived matrix formation by primary fibroblast cells, and the assay measuring the proliferation of keratinocyte cells are at least 10%, more preferably at least 15%, 20%, 30%, 40% or 50% below the respective control value.

Therefore, in another preferred embodiment of a method of the invention, step a) further comprises the following step:

iiia) measuring the proliferation of keratinocyte cells in the presence of a wound exudate sample or wound biofilm sample obtained from said skin wound, and wherein step b) comprises:

b) identifying the skin wound as being a non-healing skin wound in case at least two, preferably three of the values obtained in i) to iiia) are below the respective control values established in the absence of wound exudate or wound biofilm, more preferably wherein the values obtained in i) and/or ii) and iiia) are at least 10%, more preferably at least 15%, below the respective control value, or identifying the skin wound as being a healing skin wound in case at least two, preferably three of the values obtained in i) to iii) are equal to or above the respective control values established in the absence of wound exudate or wound biofilm, more preferably wherein the values obtained in i) and/or ii) and iiia) are at least 10%, more preferably at least 15%, above the respective control value, even more preferably wherein the value obtained in i) is at least 10%, more preferably at least 15%, above the respective control value and/or the value obtained in ii) is at least 50%, more preferably at least 100%, above the respective control value and the value obtained in iiia) is at least 10%, more preferably at least 15%, above the respective control value.

preferably wherein a combined value is established for the values obtained in i) and/or ii) and iiia).

In one preferred embodiment of the present invention, the sample is a wound exudate sample. In another preferred embodiment, the sample is a wound biofilm sample. In a more preferred embodiment, the sample is a wound exudate sample.

In step iiia), the proliferation of keratinocyte cells is measured in the presence of a wound exudate sample or wound biofilm sample obtained from said skin wound. The keratinocyte proliferation assay preferably includes culturing human primary keratinocyte cells, or HaCaT cells, which is a standard keratinocyte cell line, under standard conditions, such as by using DMEM containing FCS as medium, as for example described in the Examples. The cells are subsequently incubated on a solid support, thereby allowing the cells to adhere to the support. Further, the cells are contacted with the wound exudate sample or wound biofilm sample, which is optionally diluted, wherein the contacting may be performed before or after adherence of the cells occurs. For example, the optionally diluted wound exudate sample or wound biofilm sample may be added to the adherent cells, for example by pipetting or otherwise adding the liquid, or the optionally diluted wound exudate sample or wound biofilm sample may be added to the non-adherent cells, for example by pipetting or otherwise adding the liquid to the cells, followed by allowing the keratinocyte cells to adhere. The cells are subsequently incubated, preferably for 6 hours to 200 hours, preferably 24 hours to 100 hours. In the examples, the cells are incubated for 72 hours. Subsequently, the amount, preferably the cell number, of the keratinocyte cells, is determined, such as by fixing cells and determining total protein content. The cells may for example be fixed using paraformaldehyde. Further, a suitable dye, such as sulforhodamine B may be used for determining the amount, preferably the cell number, of the keratinocyte cells. The stained cells may then be quantified e.g. by determining absorbance or fluorescence at a suitable wavelength, depending on the dye. Preferably, the method is performed in 2D cell culture, which allows for culturing the cells adherently on a solid support. Preferably, the sample is a wound exudate sample.

A keratinocyte cell may be a primary keratinocyte cell or a keratinocyte cell line, in particular a human primary keratinocyte cell or a human keratinocyte cell line. In one preferred embodiment, the keratinocyte cells used in the present invention are selected from HaCaT cells and primary keratinocyte cells. HaCaT cells represent an established and widely used human keratinocyte cell line.

In a more preferred embodiment, the keratinocyte cells used in the present invention are HaCaT cells.

Therefore, in a preferred embodiment, measuring the proliferation of keratinocyte cells in the presence of a wound exudate sample or wound biofilm sample obtained from a skin wound includes the following steps:

(i) culturing keratinocyte cells,
(ii) incubating the cells on a solid support, thereby allowing the cells to adhere to the support,
(iii) contacting the cells with the wound exudate sample or wound biofilm sample, which is optionally diluted, wherein the contacting may be performed before or after adherence of the cells occurs, (iv) determining the amount, preferably the cell number, of the keratinocyte cells, such as by fixing cells and determining total protein content, preferably wherein the method is performed in 2D cell culture.

In one preferred embodiment of the present invention, the sample is a wound exudate sample. In another preferred embodiment, the sample is a wound biofilm sample. In a more preferred embodiment, the sample is a wound exudate sample.

Moreover, it was surprisingly found that the accuracy and reliability can be further increased by including one or more further assays in the method which determine macrophage M1 and M2 markers in the context of wound exudate. These markers may be cell surface protein markers, protein markers in the supernatant of macrophages or marker mRNAs in macrophages.

Macrophages are tissue-resident professional phagocytes and antigen-presenting cells (APC), which differentiate from circulating peripheral blood monocytes. Activated macrophages of different phenotypes are classified by skilled persons into M1-macrophages and M2 macrophages. M1-macrophages are activated macrophages which comprise immune effector cells with an acute inflammatory phenotype. These are highly aggressive against bacteria and produce large amounts of lymphokines. The M2-macrophages are alternatively activated and anti-inflammatory.

A "M2 marker" is understood as a protein marker which is specific for M2 macrophages. Preferably, the marker is secreted by the macrophages. Suitable M2 markers are known in the art and are preferably selected from CCL22 and CCL18. The markers may be determined by methods known in the art, e.g. by using an immunological assay, even more preferably by using an ELISA assay.

A "M1 marker" is understood as a protein marker which is specific for M1 macrophages. Preferably, the marker is secreted by the macrophages. Suitable M1 markers are known in the art and are preferably selected from CXCL10 and IL-23p19. The markers may be determined by methods known in the art, e.g. by using an immunological assay, even more preferably by using an ELISA assay.

A "M1 cell surface marker" is understood as a protein marker which is expressed at the surface of macrophages, and which is specific for M1 macrophages. Suitable M1 cell surface markers are known in the art and are preferably selected from CD38, CD64 and CD197. The amount(s) and/or frequency distribution(s) of the cell surface markers may be determined by an immunological assay and/or a fluorescence assay, in particular by FACS analysis, whereby typically a frequency distribution is determined.

A "M2 cell surface marker" is understood as a protein marker which is expressed at the surface of macrophages, and which is specific for M2 macrophages. Suitable M2 cell surface markers are known in the art and are preferably selected from CD200 receptor (CD200R), CD206 and CD209. The amount(s) and/or frequency distribution(s) of the cell surface markers may be determined by an immunological assay and/or a fluorescence assay, in particular by FACS analysis, whereby typically a frequency distribution is determined.

A "M2 marker mRNA" is understood as an mRNA which is expressed by macrophages, and which is specific for M2 macrophages. Suitable M2 marker mRNAs are known in the art and are preferably selected CD200 receptor (CD200R), CD206, CD209, CCL22 and CCL18. The marker mRNAs may be determined by methods known in the art. Preferably, the amount may be determined by contacting a probe which specifically binds to a marker mRNA, wherein the probe is optionally labelled, with the macrophage RNA under conditions which are conducive to hybridization, and detecting the hybridized probe. For example, the mRNA may be reversely transcribed into cDNA prior to detection.

A "M1 marker mRNA" is understood as an mRNA which is expressed by macrophages, and which is specific for M1 macrophages. Suitable M1 marker mRNAs are known in the art and are preferably selected from CD38, CD64, CD197, CXCL10 and IL-23p19. Preferably, the amount may be determined by contacting a probe which specifically binds to a marker mRNA, wherein the probe is optionally labelled, with the macrophage RNA under conditions which are conducive to hybridization, and detecting the hybridized probe. For example, the mRNA may be reversely transcribed into cDNA prior to detection.

It was surprisingly found that the ratio of M1/M2 markers is indicative of a healing or non-healing skin wound, in combination with one or more cellular assays described above relating to measuring the proliferation of primary fibroblast cells, measuring the fibroblast-derived matrix (FDM) formation by primary fibroblast cells and measuring the proliferation of keratinocyte cells. In particular, an elevated ratio of M1/M2 markers, M1/M2 cell surface markers or M1/M2 marker mRNAs is indicative of a non-healing skin wound, whereas a low ratio of M1/M2 markers, M1/M2 cell surface markers or M1/M2 marker mRNAs is indicative of a healing skin wound.

As shown in Example 3.1.6 and FIGS. 38 to 43 and 45, it was surprisingly found that the amounts of the pro-inflammatory cytokines IL1alpha, IL1beta and TNF-alpha secreted by macrophages in a macrophage/fibroblast co-culture were found to be particularly predictive for identifying healing skin wounds or non-healing skin wounds as well as for monitoring wound healing. In particular, higher amounts of these cytokines were found to be secreted in the presence of WE from non-healing wounds as compared to WE from healing wounds. Cytokines IL1alpha, IL1beta and TNF-alpha are proteins, preferably human proteins, which are well-known to a skilled person. IL1alpha (also known as Interleukin-1α or IL-1α), IL1beta (also known as Interleukin-1β or IL-1β) and TNF-alpha (also known as Tumor Necrosis Factor α or TNF-α) may be determined by methods known in the art, e.g. by using an immunological assay, even more preferably by using an ELISA assay, as described in the Examples. IL1alpha, IL1beta and TNF-alpha are known to be pro-inflammatory cytokines.

Therefore, in a further preferred embodiment of the present invention, step a) of the method of the invention further comprises one, two or three of the following steps iiib) to iiid):

iiib) measuring the amount(s) of one or more M1 marker(s) and one or more M2 marker(s) in the supernatant of macrophages incubated with a wound exudate sample or wound biofilm sample obtained from said skin wound, wherein the macrophages are in co-culture with fibroblasts, iiic) measuring the amount(s) and/or frequency distribution (s) of one or more M1 cell surface marker(s) and one or more M2 cell surface marker(s) on macrophages incubated with a wound exudate sample or wound biofilm sample obtained from said skin wound, wherein the macrophages are in co-culture with fibroblasts, iiid) measuring the expression level(s) of one or more M1 marker mRNA(s) and one or more M2 marker mRNA(s)

in macrophages incubated with a wound exudate sample or wound biofilm sample obtained from said skin wound, wherein the macrophages are in co-culture with fibroblasts, and wherein step b) of the method of the invention comprises:

b) identifying the skin wound as being a non-healing skin wound in case at least two, preferably three, four, five or six of (1) to (6) are fulfilled:
  (1) the value obtained in i) is below the respective control value established in the absence of wound exudate or wound biofilm,
  (2) the value obtained in ii) is below the respective control value established in the absence of wound exudate or wound biofilm,
  (3) the value obtained in iiia) is below the respective control value established in the absence of wound exudate or wound biofilm,
  (4) the ratio of amount(s) of one or more M1 marker(s) to the amount(s) of one or more M2 marker(s) obtained in iiib) is/are above a cut-off value,
  (5) the ratio of amount(s) and/or frequency distribution(s) of one or more M1 cell surface marker(s) to the amount(s) and/or frequency distribution(s) of one or more M2 cell surface marker(s) obtained in iiic) is/are above a cut-off value,
  (6) the ratio of expression level(s) of one or more M1 marker mRNA(s) to the expression level(s) of one or more M2 marker mRNA(s) obtained in iiid) is/are above a cut-off value,
  or
  identifying the skin wound as being a healing skin wound in case at least two, preferably three, four, five or six of (1) to (6):
  (1) the value obtained in i) is equal to or above the respective control value established in the absence of wound exudate or wound biofilm,
  (2) the value obtained in ii) is equal to or above the respective control value established in the absence of wound exudate or wound biofilm,
  (3) the value obtained in iiia) is equal to or above the respective control value established in the absence of wound exudate or wound biofilm,
  (4) the ratio of amount(s) of one or more M1 marker(s) to the amount(s) of one or more M2 marker(s) obtained in iiib) is/are below a cut-off value,
  (5) the ratio of amount(s) and/or frequency distribution(s) of one or more M1 cell surface marker(s) to the amount(s) and/or frequency distribution(s) of one or more M2 cell surface marker(s) obtained in iiic) is/are below a cut-off value,
  (6) the ratio of expression level(s) of one or more M1 marker mRNA(s) to the expression level(s) of one or more M2 marker mRNA(s) obtained in iiid) is/are below a cut-off value, preferably wherein a combined value is established for the values obtained in i), ii), iiia), iiib), iiic) and/or iiid).

Therefore, in a yet further preferred embodiment of the present invention, step a) of the method of the invention further comprises one, two or three of the following steps iiib) to iiid), or comprises one, two, three or four of the following steps iiib) to iiie):

iiib) measuring the amount(s) of one or more M1 marker(s) and one or more M2 marker(s) in the supernatant of macrophages incubated with a wound exudate sample or wound biofilm sample obtained from said skin wound, wherein the macrophages are in co-culture with fibroblasts, wherein the one or more M1 markers are selected from CXCL10 and IL-23p19, and the one or more M2 markers are selected from CCL22 and CCL18, iiic) measuring the amount(s) and/or frequency distribution(s) of one or more M1 cell surface marker(s) and one or more M2 cell surface marker(s) on macrophages incubated with a wound exudate sample or wound biofilm sample obtained from said skin wound, wherein the macrophages are in co-culture with fibroblasts, wherein the one or more M1 cell surface markers are selected from CD38, CD64 and CD197, and wherein the one or more M2 cell surface markers are selected from CD200 receptor, CD206 and CD209, iiid) measuring the expression level(s) of one or more M1 marker mRNA(s) and one or more M2 marker mRNA(s) in macrophages incubated with a wound exudate sample or wound biofilm sample obtained from said skin wound, wherein the macrophages are in co-culture with fibroblasts, wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18, iiie) measuring the amount(s) of one or more cytokine markers in the supernatant of macrophages incubated with a wound exudate sample or wound biofilm sample obtained from said skin wound, wherein the macrophages are in co-culture with fibroblasts, and wherein the one or more cytokine markers are selected from IL-1alpha, IL-1 beta and TNF-alpha, and wherein step b) comprises:

b) identifying the skin wound as being a non-healing skin wound in case at least two, preferably three, four, five or six of (1) to (6), or at least two, preferably three, four, five, six or seven of (1) to (7) are fulfilled:
  (1) the value obtained in i) is below the respective control value established in the absence of wound exudate or wound biofilm,
  (2) the value obtained in ii) is below the respective control value established in the absence of wound exudate or wound biofilm,
  (3) the value obtained in iiia) is below the respective control value established in the absence of wound exudate or wound biofilm,
  (4) the ratio of amount(s) of one or more M1 marker(s) to the amount(s) of one or more M2 marker(s) obtained in iiib) is/are above a cut-off value,
  (5) the ratio of amount(s) and/or frequency distribution(s) of one or more M1 cell surface marker(s) to the amount(s) and/or frequency distribution(s) of one or more M2 cell surface marker(s) obtained in iiic) is/are above a cut-off value, in particular wherein the ratio is selected from a CD38/CD209 ratio, a CD197/CD209 ratio and a CD197/CD206 ratio,
  (6) the ratio of expression level(s) of one or more M1 marker mRNA(s) to the expression level(s) of one or more M2 marker mRNA(s) obtained in iiid) is/are above a cut-off value,
  (7) the value obtained in iiie) is above a cut-off value,
  or
identifying the skin wound as being a healing skin wound in case at least two, preferably three, four, five or six of (1) to (6) or at least two, preferably three, four, five, six or seven of (1) to (7) are fulfilled:
  (1) the value obtained in i) is equal to or above the respective control value established in the absence of wound exudate or wound biofilm, (2) the value obtained in ii) is equal to or above the respective control value established in the absence of wound exudate or wound biofilm,
(3) the value obtained in iiia) is equal to or above the respective control value established in the absence of wound exudate or wound biofilm,
(4) the ratio of amount(s) of one or more M1 marker(s) to the amount(s) of one or more M2 marker(s) obtained in iiib) is/are below a cut-off value,
(5) the ratio of amount(s) and/or frequency distribution(s) of one or more M1 cell surface marker(s) to the amount(s) and/or frequency distribution(s) of one or more M2 cell surface marker(s) obtained in iiic) is/are below a cut-off value, in particular wherein the ratio is selected from a CD38/CD209 ratio, a CD197/CD209 ratio and a CD197/CD206 ratio,
(6) the ratio of expression level(s) of one or more M1 marker mRNA(s) to the expression level(s) of one or more M2 marker mRNA(s) obtained in iiid) is/are below a cut-off value,
(7) the value obtained in iiie) is below a cut-off value,
preferably wherein a combined value is established for the values obtained in i), ii), iiia), iiib), iiic) iiid) and/or iiie).

In one preferred embodiment of the present invention, the sample is a wound exudate sample. In another preferred embodiment, the sample is a wound biofilm sample. In a more preferred embodiment, the sample is a wound exudate sample.

In a yet further preferred embodiment of the present invention, step a) of the method of the invention further comprises one, two or three of the above steps iiib), iiic) and iiie). In such preferred embodiment, step b) comprises identifying the skin wound as being a non-healing skin wound in case at least two, preferably three, four, five or six of (1) to (5) and (7) of the criteria for a non-healing skin wound above are fulfilled. Further, in such preferred embodiment, step b) comprises identifying the skin wound as being a healing skin wound in case at least two, preferably three, four, five or six of (1) to (5) and (7) of the criteria for a healing skin wound above are fulfilled.

Figure 34:
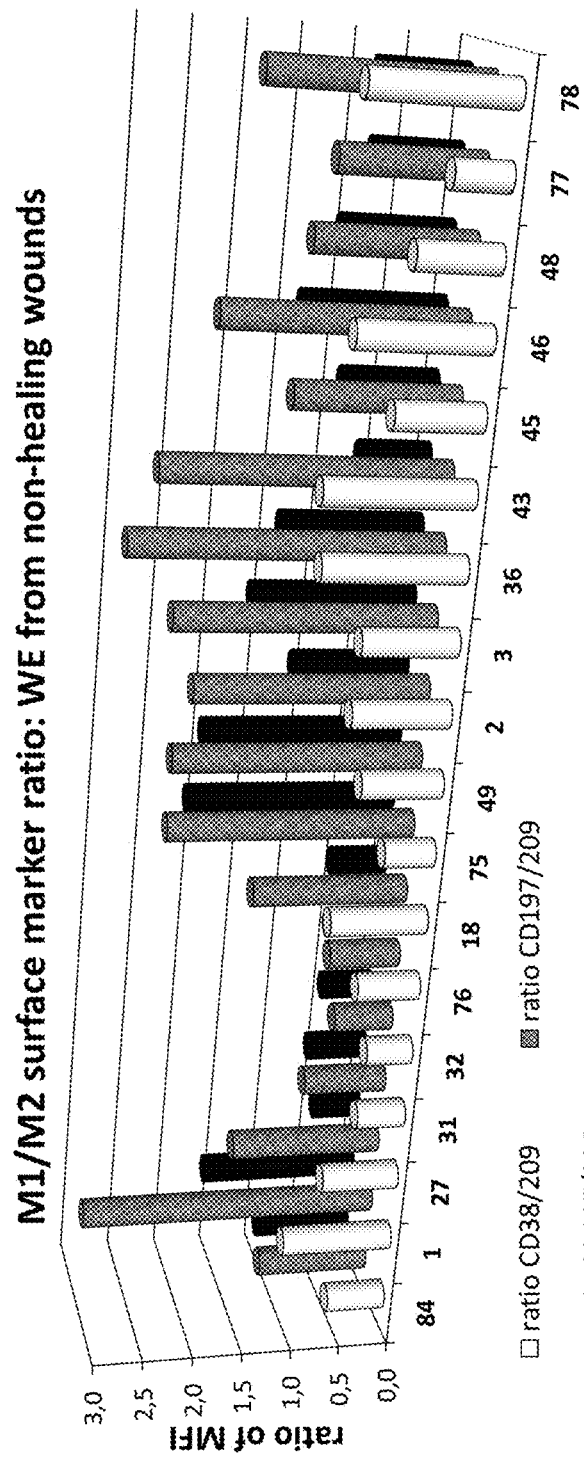
Figure 35:
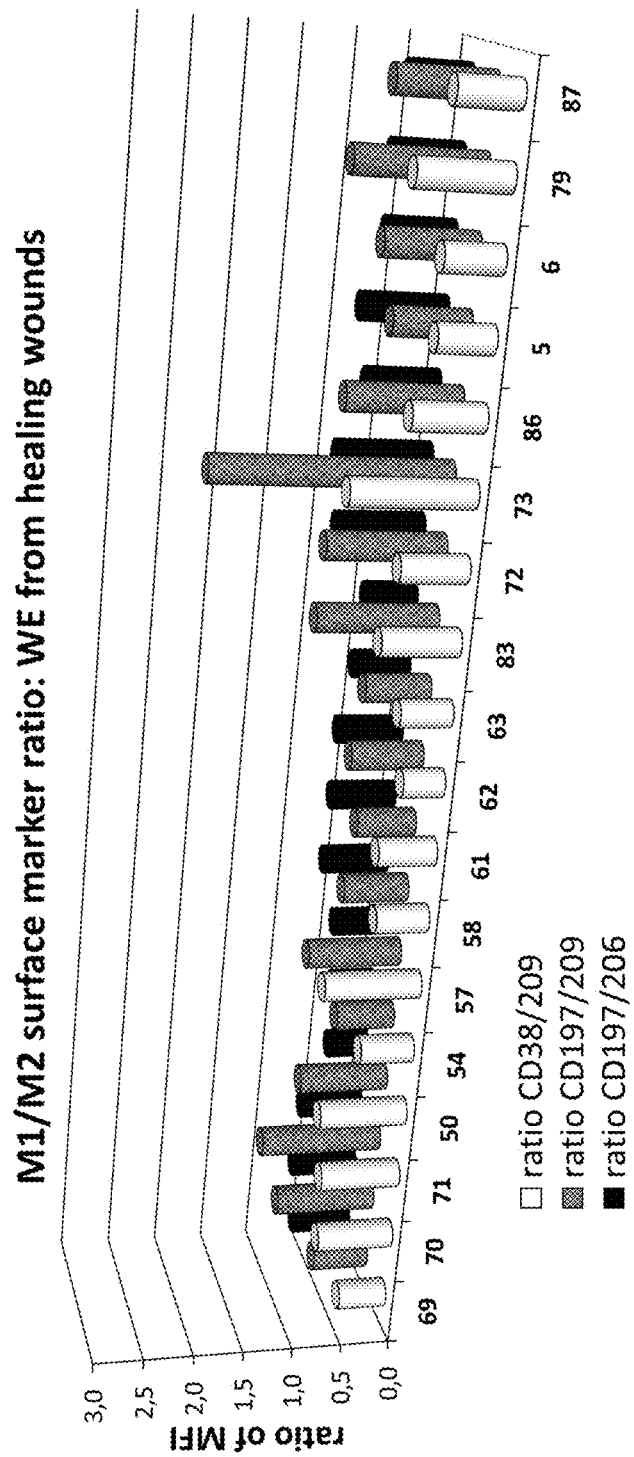
Figure 44:
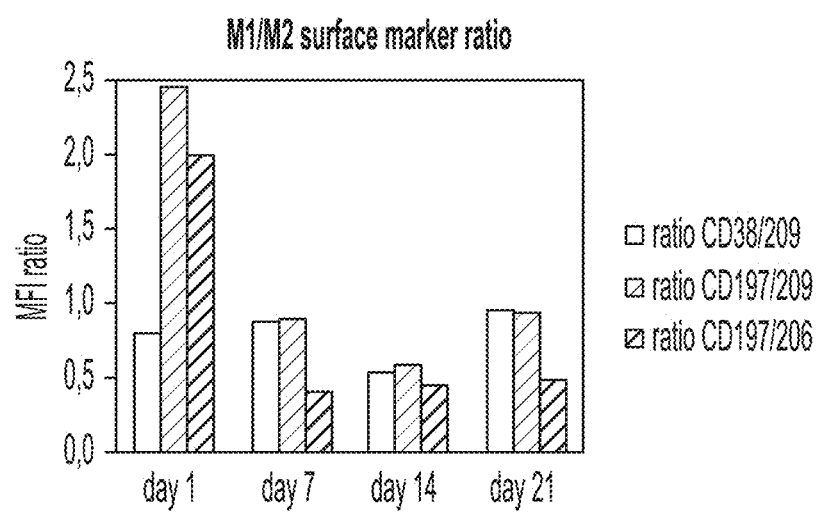

As shown in Example 3.1.6 and FIGS. 34, 35 and 44, it was surprisingly found that the following M1 cell surface marker/M2 cell surface marker ratios were found to be particularly predictive for identifying healing skin wounds or non-healing skin wounds, respectively: a CD38/CD209 ratio, a CD197/CD209 ratio and a CD197/CD206 ratio.

Accordingly, in a preferred embodiment, the skin wound is identified as non-healing skin wound, in case the ratio of amount(s) and/or frequency distribution(s) selected from a CD38/CD209 ratio, a CD197/CD209 ratio and a CD197/CD206 ratio obtained in iiic) is/are above a cut-off value.

Accordingly, in another preferred embodiment, the skin wound is identified as healing skin wound, in case the ratio of amount(s) and/or frequency distribution(s) selected from a CD38/CD209 ratio, a CD197/CD209 ratio and a CD197/CD206 ratio obtained in iiic) is/are below a cut-off value.

The frequency distribution may be determined by determining the % age of cells which are positive for a given marker within a population, which is the most commonly used readout in FACS analysis. Alternatively, the amount may be determined by determining the quantity of cell surface expression, as a surrogate for the number of labelled molecules on the cell surface per individual cell when using labelled binding agents for the markers, as for example measured by the mean fluorescence intensity.

In a preferred embodiment, measuring the amount(s) of one or more M1 marker(s) and one or more M2 marker(s) in the supernatant of macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample or wound biofilm sample, which is optionally diluted,
(iv) determining the amount of one or more M1 markers and one or more M2 markers in the cell culture supernatant, preferably wherein the one or more M1 markers are selected from CXCL10 and IL-23p19, and/or the one or more M2 markers are selected from CCL22 and CCL18, more preferably wherein the markers are determined by using an immunological assay, even more preferably by using an ELISA assay, In one preferred embodiment of the present invention, the sample is a wound exudate sample. In another preferred embodiment, the sample is a wound biofilm sample. In a more preferred embodiment, the sample is a wound exudate sample.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample or wound biofilm sample, which is optionally diluted, for example by pipetting the sample to the cells, and optionally gentle mixing. Further, the cells are incubated, preferably for 1 hour 100 hours, e.g. 4 hours to 100 hours. Subsequently, the amount of one or more M1 markers and one or more M2 markers in the cell culture supernatant is determined. The supernatant is typically harvested for such purpose and the markers are determined using a suitable assay, such as immunological assay. For example, an ELISA may be used. In a preferred embodiment, the sample is a wound exudate sample.

In another preferred embodiment, measuring the amount(s) and/or frequency distribution(s) of one or more M1 cell surface marker(s) and one or more M2 cell surface marker(s) on macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample or wound biofilm sample, which is optionally diluted,
(iv) determining the amount(s) and/or frequency distribution(s) of one or more M1 marker(s) and one or more M2 marker(s) on the cell surface of macrophages.

In one preferred embodiment of the present invention, the sample is a wound exudate sample. In another preferred embodiment, the sample is a wound biofilm sample. In a more preferred embodiment, the sample is a wound exudate sample.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample or wound biofilm sample, which is optionally diluted, for example by pipetting the sample to the cells, and optionally gentle mixing. Further, the cells are incubated, preferably for 1 hour 100 hours, e.g. 4 hours to 100 hours. Subsequently, the amount(s) and/or frequency distribution(s) of one or more M1 marker(s) and one or more M2 marker(s) on the cell surface of macrophages is determined. For example, the cells may be harvested and subjected to FACS analysis, gating on the monocyte/macrophage population. Geometric means of mean fluorescence intensities can be used to quantify surface marker expression.

Preferably, the one or more M1 cell surface markers are selected from CD38, CD64 and CD197, and/or the one or more M2 cell surface markers are selected from CD200 receptor (CD200R), CD206 and CD209, more preferably wherein the amount(s) and/or frequency distribution(s) of the cell surface markers are determined by an immunological assay and/or a fluorescence assay, in particular by FACS analysis.

In one preferred embodiment, step (iv) comprises contacting the macrophages with binding agents, preferably antibodies, which specifically recognize one or more M1 cell surface marker(s) and one or more M2 cell surface marker(s), wherein the binding agents are optionally labelled, in particular labelled with a fluorescent label, and determining the amounts of binding molecules bound to the macrophages, in particular by determining mean fluorescence intensity, thereby determining the amount(s) of the cell surface markers. For example, antibodies specifically recognizing the surface markers and which contain a fluorescent label may be used.

In another preferred embodiment, step (iv) comprises contacting the macrophages with binding agents, preferably antibodies, which specifically recognize one or more M1 cell surface marker(s) and one or more M2 cell surface marker(s), wherein the binding agents are optionally labelled, in particular labelled with a fluorescent label, and determining the percentages of cells which are positive for the one or more M1 cell surface marker(s) and the one or more M2 cell surface marker(s), respectively, within a cell population, in particular wherein FACS analysis is performed, thereby determining the frequency distribution(s) of the cell surface markers. For example, antibodies specifically binding to the surface markers and which contain a fluorescent label may be used.

Determination of proteins as binding agents of a marker protein can be performed using any of a number of known methods for identifying and obtaining proteins that specifically interact with proteins or polypeptides, for example, a yeast two-hybrid screening system such as that described in U.S. Pat. Nos. 5,283,173 and 5,468,614, or the equivalent. A binding agent which specifically recognizes a marker has preferably at least an affinity of $10^7$ l/mol for its corresponding target molecule. The binding agent which specifically recognizes a marker preferably has an affinity of $10^8$ l/mol or even more preferred of $10^9$ l/mol for its target marker molecule. As the skilled person will appreciate, the term specific is used to indicate that other biomolecules present in the sample do not significantly bind to the binding agent which specifically recognizes the marker. Preferably, the level of binding to a biomolecule other than the target marker molecule results in a binding affinity which is only 10% or less, more preferably only 5% or less of the affinity to the target marker molecule, respectively. A preferred specific binding agent will fulfill both the above minimum criteria for affinity as well as for specificity.

A binding agent which specifically recognizes a marker preferably is an antibody reactive with the marker. The term antibody refers to a polyclonal antibody, a monoclonal antibody, antigen binding fragments of such antibodies, single chain antibodies as well as to genetic constructs comprising the binding domain of an antibody.

The term "antibodies" includes polyclonal antibodies, monoclonal antibodies, fragments thereof such as F(ab')2, and Fab fragments, as well as any naturally occurring or recombinantly produced binding partners, which are molecules that specifically bind to a marker protein. Any antibody fragment retaining the above criteria of a specific binding agent can be used. Antibodies are generated by state of the art procedures, e.g., as described in Tijssen (Tijssen, P., Practice and theory of enzyme immunoassays, Elsevier Science Publishers B.V., Amsterdam (1990), the whole book, especially pages 43-78). In addition, the skilled person is well aware of methods based on immunosorbents that can be used for the specific isolation of antibodies. By these means the quality of polyclonal antibodies and hence their performance in immunoassays can be enhanced (Tijssen, P., supra, pages 108-115).

For the achievements as disclosed in the present invention polyclonal antibodies raised in e.g. goats may be used. However, clearly also polyclonal antibodies from different species, e.g., rats, rabbits or guinea pigs, as well as monoclonal antibodies can be used. Since monoclonal antibodies can be produced in any amount required with constant properties, they represent ideal tools in development of an assay for clinical routine.

For measurement, the sample obtained from an individual is incubated with the binding agent that specifically recognizes the marker in question under conditions appropriate for formation of a binding agent marker-complex. Such conditions need not be specified, since the skilled artisan without any inventive effort can easily identify such appropriate incubation conditions. The amount of binding agent marker-complex is measured and used in the methods and uses of the invention. As the skilled artisan will appreciate there are numerous methods to measure the amount of the specific binding agent marker-complex all described in detail in relevant textbooks (cf., e.g., Tijssen P., supra, or Diamandis, E. P. and Christopoulos, T. K. (eds.), Immunoassay, Academic Press, Boston (1996)).

Particularly, monoclonal antibodies to the marker(s) are used in a quantitative (amount or concentration of the marker(s) is determined) immunoassay.

For example, the marker may be detected in a sandwich type assay format. In such assay a first specific binding agent is used to capture the marker in question on the one side and a second specific binding agent (e.g. a second antibody), is which is labeled to be directly or indirectly detectable, is used on the other side. The second specific binding agent may contain a detectable reporter moiety or label such as an enzyme, dye, radionuclide, luminescent group, fluorescent group or biotin, or the like. Any reporter moiety or label could be used with the methods disclosed herein so long as the signal of such is directly related or proportional to the quantity of binding agent remaining on the support after wash. The amount of the second binding agent that remains bound to the solid support is then determined using a method appropriate for the specific detectable reporter moiety or label. For radioactive groups, scintillation counting or autoradiographic methods are generally appropriate. Antibody-enzyme conjugates can be prepared using a variety of coupling techniques (for review see, e.g., Scouten, W. H., Methods in Enzymology 135:30-65, 1987). Spectroscopic methods can be used to detect dyes (including, for example, colorimetric products of enzyme reactions), luminescent groups and fluorescent groups. Biotin can be detected using avidin or streptavidin, coupled to a different reporter group (commonly a radioactive or fluorescent group or an enzyme). Enzyme reporter groups can generally be detected by the addition of substrate (generally for a specific period of time), followed by spectroscopic, spectrophotometric or other analysis of the reaction products. Standards and standard additions can be used to determine the level of antigen in a sample, using well known techniques.

Immunoassays for measuring marker proteins of the invention include for example ELISA, enzyme immunoassay (EIA) and electro-chemiluminescence immunoassay (ECLIA) for the quantitative determination of a marker protein described herein.

In another preferred embodiment, measuring the expression level(s) of one or more M1 marker mRNA(s) and one or more M2 marker mRNAs) in macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample or wound biofilm sample, which is optionally diluted,
(iv) determining the expression level(s) of one or more M1 marker mRNA(s) and one or more M2 marker mRNA(s) in the macrophages.

In one preferred embodiment of the present invention, the sample is a wound exudate sample. In another preferred embodiment, the sample is a wound biofilm sample. In a more preferred embodiment, the sample is a wound exudate sample.

Preferably, the one or more M1 marker mRNA(s) are selected from CD38, CD64, CD197, CXCL10 and IL-23p19, and/or the one or more M2 marker mRNA(s) are selected from CD200 receptor (CD200R), CD206, CD209, CCL22 and CCL18, more preferably the method comprises contacting a probe which specifically binds to a marker mRNA, wherein the probe is optionally labelled, with the macrophage RNA under conditions which are conducive to hybridization, and detecting the hybridized probe.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample or wound biofilm sample, which is optionally diluted, for example by pipetting the sample to the cells, and optionally gentle mixing. Further, the cells are incubated, preferably for 1 hour 100 hours, e.g. 4 hours to 100 hours.

Subsequently, the expression level(s) of one or more M1 marker mRNA(s) and one or more M2 marker mRNA(s) in the macrophages is determined. For example, the cells may be harvested and mRNA expression level(s) may be determined using suitable probes. For example, the expression level of a housekeeping gene such as actin or GAPDH may be determined and the expression level(s) of M1 or M2 marker RNA(s) may be determined as expression level relative to a housekeeping gene.

In another preferred embodiment, measuring the amount(s) of one or more cytokine markers selected from IL-1 alpha, IL-1 beta and TNF-alpha in the supernatant of macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample or wound biofilm sample, which is optionally diluted,
(iv) determining the amount of one or more cytokine markers selected from IL-1alpha, IL-1beta and TNF-alpha in the cell culture supernatant,
preferably wherein the cytokine markers are determined by using an immunological assay, more preferably by using an ELISA assay.

In one preferred embodiment of the present invention, the sample is a wound exudate sample. In another preferred embodiment, the sample is a wound biofilm sample. In a more preferred embodiment, the sample is a wound exudate sample.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample or wound biofilm sample, which is optionally diluted, for example by pipetting the sample to the cells, and optionally gentle mixing. Further, the cells are incubated, preferably for 1 hour to 100 hours, e.g. 4 hours to 100 hours. Subsequently, the amount of one or more of IL-1alpha, IL-1 beta and TNF-alpha in the cell culture supernatant is determined. The supernatant is typically harvested for such purpose and the cytokine markers are determined using a suitable assay, such as immunological assay. For example, an ELISA may be used. In a preferred embodiment, the sample is a wound exudate sample.

As shown in Example 3.1.6 and FIGS. 38 to 43 and 45, the amounts of IL-1alpha, IL-1beta and TNF-alpha in the supernatant are higher in the presence of wound exudates from non-healing wounds as compared to healing wounds, and are higher in the presence of a wound exudate from a wound in a non-healing situation as compared to a wound exudate from the same wound in a healing situation, at different time points. Accordingly, the amounts of IL-1 alpha, IL-1beta and TNF-alpha are indicative for a healing or non-healing wound, respectively, as well as for monitoring wound healing of a skin wound. In this context, a cut-off value is suitably determined.

A suitable cut-off value for the assays may be chosen depending on the sensitivity and specificity desired. Sensitivity and specificity are statistical measures of the performance of a binary classification test, also known in statistics as classification function:

Sensitivity (also called the true positive rate) measures the proportion of positives that are correctly identified as such (e.g., the percentage of healing skin wounds identified as healing skin wound, respectively).

Specificity (also called the true negative rate) measures the proportion of negatives that are correctly identified as such (e.g., the percentage of healing skin wounds identified as being a non-healing skin wound).

For any test, there is usually a trade-off between the measures. For instance, in an airport security setting in which one is testing for potential threats to safety, scanners may be set to trigger on low-risk items like belt buckles and keys (low specificity), in order to reduce the risk of missing objects that do pose a threat to the aircraft and those aboard (high sensitivity). This trade-off can be represented graphically as a receiver operating characteristic curve. A perfect predictor would be described as 100% sensitive (e.g., all non-healing skin wounds are identified as non-healing skin wounds) and 100% specific (e.g., all healing skin wounds are not identified as non-healing skin wounds); however, theoretically any predictor will possess a minimum error bound known as the Bayes error rate. The cut-off can be set in order to either increase sensitivity or specificity.

If two or more values, such as the values determined when performing the assays measuring the proliferation of primary fibroblast cells and measuring the fibroblast-derived matrix formation by primary fibroblast cells, are used in the methods of the invention, a combined value may be calculated using the two or more values obtained in the assays. The combined value is compared to the combined value of the respective control, which has been obtained using the same mathematical procedure. In a preferred embodiment, the combined value is obtained by weighted calculation of the values. This means that one of the assays is given a higher weighting that the other. Preferably, the weighting factors have been obtained by analyzing a reference population of skin wounds.

Further, it was surprisingly found that an increased accuracy and reliability can be achieved in case two or more of the cellular and biochemical assays described herein are performed, wherein the value(s) obtained the assays measuring the proliferation of primary fibroblast cells and/or measuring the fibroblast-derived matrix (FDM) formation by primary fibroblast cells are mandatory for identifying a skin wound as healing skin wound or non-healing skin wound. For example, identifying a skin wound as non-healing skin wound preferably requires that at least the value(s) obtained in the assays measuring the proliferation of primary fibroblast cells and/or measuring the fibroblast-derived matrix (FDM) formation by primary fibroblast cells is/are below the respective control value(s) established in the absence of wound exudate or wound biofilm. Further, identifying a skin wound as healing skin wound preferably requires that at least the value(s) obtained in the assays measuring the proliferation of primary fibroblast cells and/or measuring the fibroblast-derived matrix (FDM) formation by primary fibroblast cells is/are equal or above the respective control value(s) established in the absence of wound exudate or wound biofilm. Preferably, the sample is a wound exudate sample.

Therefore, in a more preferred embodiment of the present invention, step b) comprises:
identifying the skin wound as being a non-healing skin wound in case at least two, preferably three, four, five or six of (1) to (6) are fulfilled:
(1) the value obtained in i) is below the respective control value established in the absence of wound exudate or wound biofilm,
(2) the value obtained in ii) is below the respective control value established in the absence of wound exudate or wound biofilm,
(3) the value obtained in iiia) is below the respective control value established in the absence of wound exudate or wound biofilm,
(4) the ratio of amount(s) of one or more M1 marker(s) to the amount(s) of one or more M2 marker(s) obtained in iiib) is/are above a cut-off value,
(5) the ratio of amount(s) and/or frequency distribution(s) of one or more M1 cell surface marker(s) to the amount(s) and/or frequency distribution(s) of one or more M2 cell surface marker(s) obtained in iiic) is/are above a cut-off value,
(6) the ratio of expression level(s) of one or more M1 marker mRNA(s) to the expression level(s) of one or more M2 marker mRNA(s) obtained in iiid) is/are above a cut-off value,
with the proviso that at least the value(s) obtained in i) and/or ii) is/are below the respective control value(s) established in the absence of wound exudate or wound biofilm, and/or
identifying the skin wound as being a healing skin wound in case at least two, preferably three, four, five or six of (1) to (6) are fulfilled:
(1) the value obtained in i) is above the respective control value established in the absence of wound exudate or wound biofilm,
(2) the value obtained in ii) is above the respective control value established in the absence of wound exudate or wound biofilm,
(3) the value obtained in iiia) is above the respective control value established in the absence of wound exudate or wound biofilm,
(4) the ratio of amount(s) of one or more M1 marker(s) to the amount(s) of one or more M2 marker(s) obtained in iiib) is/are below a cut-off value,
(5) the ratio of amount(s) and/or frequency distribution(s) of one or more M1 cell surface marker(s) to the amount(s) and/or frequency distribution(s) of one or more M2 cell surface marker(s) obtained in iiic) is/are below a cut-off value,
(6) the ratio of expression level(s) of one or more M1 marker mRNA(s) to the expression level(s) of one or more M2 marker mRNA(s) obtained in iiid) is/are below a cut-off value,
with the proviso that at least the value(s) obtained in i) and/or ii) is/are equal to or above the respective control value(s) established in the absence of wound exudate or wound biofilm.

Therefore, in another more preferred embodiment of the present invention, step b) comprises:
b) identifying the skin wound as being a non-healing skin wound in case at least two, preferably three, four, five or six of (1) to (6) or at least two, preferably three, four, five, six or seven of (1) to (7) are fulfilled:
(1) the value obtained in i) is below the respective control value established in the absence of wound exudate or wound biofilm, (2) the value obtained in ii) is below the respective control value established in the absence of wound exudate or wound biofilm, (3) the value obtained in iiia) is below the respective control value established in the absence of wound exudate or wound biofilm, (4) the ratio of amount(s) of one or more M1 marker(s) to the amount(s) of one or more M2 marker(s) obtained in iiib) is/are above a cut-off value, wherein the one or more M1 markers are selected from CXCL10 and IL-23p19, and the one or more M2 markers are selected from CCL22 and CCL18, (5) the ratio of amount(s) and/or frequency distribution(s) of one or more M1 cell surface marker(s) to the amount(s) and/or frequency distribution(s) of one or more M2 cell surface marker(s) obtained in iiic) is/are above a cut-off value, wherein the one or more M1 cell surface markers are selected from CD38, CD64 and CD197, and wherein the one ore more M2 cell surface markers are selected from CD200 receptor, CD206 and CD209, in particular wherein the ratio is selected from a CD38/CD209 ratio, a CD197/CD209 ratio and a CD197/CD206 ratio, (6) the ratio of expression level(s) of one or more M1 marker mRNA(s) to the expression level(s) of one or more M2 marker mRNA(s) obtained in iiid) is/are above a cut-off value, wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18, (7) the value of amount(s) of one or more cytokine markers selected from IL-1alpha, IL-1beta and TNF-alpha obtained in iiie) are above a cut-off value, with the proviso that at least the value(s) obtained in i) and/or ii) is/are below the respective control value(s) established in the absence of wound exudate or wound biofilm, and/or identifying the skin wound as being a healing skin wound in case at least two, preferably three, four, five or six of (1) to (6) or at least two, preferably three, four, five, six or seven of (1) to (7) are fulfilled:

(1) the value obtained in i) is above the respective control value established in the absence of wound exudate or wound biofilm, (2) the value obtained in ii) is above the respective control value established in the absence of wound exudate or wound biofilm, (3) the value obtained in iiia) is above the respective control value established in the absence of wound exudate or wound biofilm, (4) the ratio of amount(s) of one or more M1 marker(s) to the amount(s) of one or more M2 marker(s) obtained in iiib) is/are below a cut-off value, (5) the ratio of amount(s) and/or frequency distribution(s) of one or more M1 cell surface marker(s) to the amount(s) and/or frequency distribution(s) of one or more M2 cell surface marker(s) obtained in iiic) is/are below a cut-off value, in particular wherein the ratio is selected from a CD38/CD209 ratio, a CD197/CD209 ratio and a CD197/CD206 ratio, (6) the ratio of expression level(s) of one or more M1 marker mRNA(s) to the expression level(s) of one or more M2 marker mRNA(s) obtained in iiid) is/are below a cut-off value, (7) the value of amount(s) of one or more cytokine markers selected from IL-1alpha, IL-1 beta and TNF-alpha obtained in iiie) are below a cut-off value, with the proviso that at least the value(s) obtained in i) and/or ii) is/are equal to or above the respective control value(s) established in the absence of wound exudate or wound biofilm.

In one preferred embodiment of the present invention, the sample is a wound exudate sample. In another preferred embodiment, the sample is a wound biofilm sample. In a more preferred embodiment, the sample is a wound exudate sample.

In another more preferred embodiment of the present invention, step b) comprises identifying the skin wound as being a non-healing skin wound in case at least two, preferably three, four, five or six of (1) to (5) and (7) of the criteria for a non-healing skin wound above are fulfilled, with the proviso that at least the value(s) obtained in i) and/or ii) is/are below the respective control value(s) established in the absence of wound exudate or wound biofilm. In another more preferred embodiment of the present invention, step b) comprises identifying the skin wound as being a healing skin wound in case at least two, preferably three, four, five or six of (1) to (5) and (7) of the criteria for a healing skin wound above are fulfilled, with the proviso that at least the value(s) obtained in i) and/or ii) is/are equal to or above the respective control value(s) established in the absence of wound exudate or wound biofilm.

In a more preferred embodiment, the skin wound as identified as being a healing skin wound in case at least two, preferably three, four, five or six of (1) to (6) above or at least two, preferably three, four, five, six or seven of (1) to (7) above or at least two, preferably three, four, five or six of (1) to (5) and (7) above for a healing skin wound are fulfilled, with the proviso that at least the value(s) obtained in i) and/or ii) is/are at least 10% above the respective control values, more preferably wherein the values obtained in i) and/or ii) is/are at least 15%, even more preferably at least 20%, 30%, 40% or 50% above the respective control values, even more preferably wherein the value obtained in i) is at least 15%, even more preferably at least 20%, 30%, 40% or 50% above the respective control value and the value obtained in ii) is at least 50%, more preferably at least 100%, even more preferably 110%, 120%, 130% or 140% above the respective control value.

In another more preferred embodiment, the skin wound as identified as being a non-healing skin wound in case at least two, preferably three, four, five or six of (1) to (6) above or at least two, preferably three, four, five, six or seven of (1) to (7) above or at least two, preferably three, four, five or six of (1) to (5) and (7) above for a non-healing skin wound are fulfilled, with the proviso that at least the value(s) obtained in i) and/or ii) is/are at least 10% below the respective control values, more preferably wherein the values obtained in i) and/or ii) is/are at least 15%, even more preferably at least 20%, 30%, 40% or 50% below the respective control values.

Further, it was surprisingly possible to establish an in vitro method for monitoring the healing of a skin wound in an individual using one or more of the above-described cellular and biochemical assays. In particular, it was surprisingly found that measuring the proliferation of primary fibroblast cells in the presence of wound exudate samples obtained from a skin wound at two different time points, and/or measuring the fibroblast-derived matrix formation by primary fibroblast cells in the presence of a wound exudate sample obtained from said skin wound at two different time points allows for monitoring the healing of a wound: an increase in the value(s) determined at the later, second time point as compared to the earlier, first time point indicates that the healing of the skin wound has improved, whereas a decrease in the value(s) determined at the later time point as compared to the earlier time point indicates that the healing of the skin wound has worsened. The cellular assays are performed as described above for the methods of identifying. In addition, it is optionally possible to determine at each time point whether a skin wound is a healing skin wound or non-healing skin wound, respectively, by applying the methods of identifying described above.

Further, it is in one preferred embodiment possible to repeat the method steps one or more further time points, thereby further monitoring the healing of the patient over time.

As shown in the Figures for 3 individual patients (FIG. 27 for patient "B", FIG. 30 for patient "C" and FIG. 33 for patient "A"), the method of the invention allows for reliably monitoring and predicting the wound healing of skin wounds in a patient. For example, the method of the invention correctly predicted the subsequent worsening of skin wound healing in a patient, at a time point where visual inspection concluded an improvement in wound healing.

Therefore, in another embodiment, the present invention relates to an in vitro method for monitoring the healing of a skin wound in an individual, the method comprising:
a) measuring
  i) the proliferation of primary fibroblast cells in the presence of a wound exudate sample or wound biofilm sample obtained from said skin wound at a first time point, and/or
  ii) the fibroblast-derived matrix formation by primary fibroblast cells in the presence of a wound exudate sample or wound biofilm sample obtained from said skin wound at a first time point,
b) optionally identifying the skin wound as being a non-healing skin wound at said first time point in case the value(s) obtained in a)i) and/or a)ii) is/are below a control value established in the absence of wound exudate or wound biofilm, or identifying the skin wound as being a healing skin wound at a first time point in case the value(s) obtained in a)i) and/or a)ii) is/are equal to or above a control value established in the absence of wound exudate or wound biofilm,
c) measuring
  i) the proliferation of primary fibroblast cells in the presence of a wound exudate sample or wound biofilm sample obtained from said skin wound at a second time point, and/or
  ii) the fibroblast-derived matrix formation by primary fibroblast cells in the presence of a wound exudate sample or wound biofilm sample obtained from said skin wound at a second time point,
d) optionally identifying said skin wound as being a non-healing skin wound at said second time point, in case the value(s) obtained in c)i) and/or c)ii) is/are below a control value established in the absence of wound exudate or wound biofilm, or identifying the skin wound as being a healing skin wound at said second time point in case the value(s) obtained in c)i) and/or c)ii) is/are equal to or above a control value established in the absence of wound exudate or wound biofilm,
e)
  A) identifying a skin wound at a second time point to exhibit improved healing in case the value obtained in c)i) at said second time point is higher than the value obtained in a)i) at said first time point, and/or the value obtained in c)ii) at said second time point is higher than the value obtained in a)ii) at said first time point,
  or
  B) identifying a skin wound at a second time point to exhibit worsened healing in case the value obtained in c)i) at said second time point is lower than the value obtained in a)i) at said first time point, and/or the value obtained in c)ii) at said second time point is lower than the value obtained in a)ii) at said first time point,
and
f) optionally repeating steps a) to e) at one or more later time points,
thereby monitoring the healing of the skin wound,
preferably
wherein the first time point and the second time point are separated by between 6 hours and 12 months, and/or the values are measured at least in triplicate and/or a statistical significance is established.

In one preferred embodiment of the present invention, the sample is a wound exudate sample. In another preferred embodiment, the sample is a wound biofilm sample. In a more preferred embodiment, the sample is a wound exudate sample.

The second time point is understood to be later than the first time point. In general, the first time point and the second time point are separated by at least 6 hours, in particular by between 6 hours and 12 months. For example, the first time point and the second time point are separated by 12 hours to 3, 6 or 12 months, or 1 day, 1 week or 1 month to 12 months.

The monitoring is surprisingly reliable for determining a skin wound at a second time point to exhibit improved healing as compared to the first time point when an increase in the value(s) for one or both of the fibroblast-based assays is determined at the later time point as compared to the earlier time point, in cases where the value obtained in one or both of the assays measuring the proliferation of primary fibroblast cells in the presence of wound exudate samples or wound biofilm samples obtained from a skin wound, and measuring the fibroblast-derived matrix formation by primary fibroblast cells in the presence of a wound exudate sample or wound biofilm sample is/are equal to or below a control value established in the absence of wound exudate or wound biofilm at the first, earlier time point. Accordingly, the monitoring of an improved healing is particularly reliable in case the wound is a non-healing wound at the first, earlier time point, as determined by a method of identifying the present invention.

Accordingly, it is preferred that the method for monitoring the healing of a skin wound in an individual of the invention includes identifying the skin wound as being a non-healing skin wound or healing skin wound, respectively, at the respective time point, by performing the methods of the invention.

Further, the monitoring is surprisingly reliable for determining a skin wound at a second time point to exhibit worsened healing when a decrease in the value(s) for the one or both of the fibroblast-based assays is determined at the later time point as compared to the earlier time point, in case the value obtained in one or both of the assays measuring the proliferation of primary fibroblast cells in the presence of wound exudate samples or wound biofilm samples obtained from a skin wound, and measuring the fibroblast-derived matrix formation by primary fibroblast cells in the presence of a wound exudate sample or wound biofilm samples at the second later time point is/are equal to or below 100% of a control value established in the absence of wound exudate or wound biofilm at the first, earlier time point. Accordingly, the monitoring of a worsened healing is particularly reliable in case the wound is a non-healing wound at the second, later time point, as determined by a method for identifying of the present invention.

In one preferred embodiment of the present invention, the sample is a wound exudate sample. In another preferred embodiment, the sample is a wound biofilm sample. In a more preferred embodiment, the sample is a wound exudate sample.

It is understood that the preferred embodiments for the methods for identifying also apply to the methods for monitoring of the present invention.

Therefore, in another embodiment, the present invention relates to an in vitro method for monitoring the healing of a skin wound in an individual, the method comprising:

a) measuring
  i) the proliferation of primary fibroblast cells in the presence of a wound exudate sample or wound biofilm sample obtained from said skin wound at a first time point, and/or
  ii) the fibroblast-derived matrix formation by primary fibroblast cells in the presence of a wound exudate sample or wound biofilm sample obtained from said skin wound at a first time point,
b) optionally identifying the skin wound as being a non-healing skin wound at said first time point in case the value(s) obtained in a)i) and/or a)ii) is/are below a control value established in the absence of wound exudate or wound biofilm sample, or identifying the skin wound as being a healing skin wound at a first time point in case the value(s) obtained in a)i) and/or a)ii) is/are equal to or above a control value established in the absence of wound exudate or wound biofilm,
c) measuring
  i) the proliferation of primary fibroblast cells in the presence of a wound exudate sample or wound biofilm sample obtained from said skin wound at a second time point, and/or
  ii) the fibroblast-derived matrix formation by primary fibroblast cells in the presence of a wound exudate sample or wound biofilm sample obtained from said skin wound at a second time point,
d) optionally identifying said skin wound as being a non-healing skin wound at said second time point, in case the value(s) obtained in c)i) and/or c)ii) is/are below a control value established in the absence of wound exudate or wound biofilm sample, or identifying the skin wound as being a healing skin wound at said second time point in case the value(s) obtained in c)i) and/or c)ii) is/are equal to or above a control value established in the absence of wound exudate or wound biofilm,
e)
  A) identifying a skin wound at a second time point to exhibit improved healing in case the value obtained in c)i) at said second time point is higher than the value obtained in a)i) at said first time point, and/or the value obtained in c)ii) at said second time point is higher than the value obtained in a)ii) at said first time point, with the proviso that the value obtained in a)i) at said first time point and/or a)ii) at said first time point is equal to or below a control value established in the absence of wound exudate or wound biofilm, or
  B) identifying a skin wound at a second time point to exhibit worsened healing in case the value obtained in c)i) at said second time point is lower than the value obtained in a)i) at said first time point, and/or the value obtained in c)ii) at said second time point is lower than the value obtained in a)ii) at said first time point, with the proviso that the value(s) obtained in c)i) and/or c)ii) at said second time point is/are equal to or below 100% of a control value established in the absence of wound exudate or wound biofilm,
and
f) optionally repeating steps a) to e) at one or more later time points, thereby monitoring the healing of the skin wound, preferably wherein the first time point and the second time point are separated by between 6 hours and 12 months, and/or the values are measured at least in triplicate and/or a statistical significance is established.

In one preferred embodiment of the present invention, the sample is a wound exudate sample. In another preferred embodiment, the sample is a wound biofilm sample. In a more preferred embodiment, the sample is a wound exudate sample. In case the sample is a wound exudate sample at a first time point, the sample at the second time point is preferably also a wound exudate sample. The same applies for any repetitions of the method steps of step f).

In case the sample is a wound biofilm sample at a first time point, the sample at the second time point is preferably also a wound biofilm sample. The same applies for any repetitions of the method steps of step f).

In one preferred embodiment, the method of the invention comprises:

a) measuring
  i) the proliferation of primary fibroblast cells in the presence of a wound exudate sample or wound biofilm sample obtained from said skin wound at a first time point, and
  ii) the fibroblast-derived matrix formation by primary fibroblast cells in the presence of a wound exudate sample or wound biofilm sample obtained from said skin wound at a first time point,
b) optionally identifying the skin wound as being a non-healing skin wound at said first time point in case the value obtained in a)i) is below a control value established in the absence of wound exudate or wound biofilm, and the value obtained in a)ii) is below a control value established in the absence of wound exudate or wound biofilm, or
  identifying the skin wound as being a healing skin wound at said first time point in case the value obtained in a)i) is equal to or above a control value established in the absence of wound exudate or wound biofilm, and the value obtained in a)ii) is equal to or above a control value established in the absence of wound exudate or wound biofilm,
c) measuring
  i) the proliferation of primary fibroblast cells in the presence of a wound exudate sample or wound biofilm sample obtained from said skin wound at a second time point, and
  ii) the fibroblast-derived matrix formation by primary fibroblast cells in the presence of a wound exudate sample or wound biofilm sample obtained from said skin wound at a second time point,
d) optionally identifying the skin wound as being a non-healing skin wound at said second time point in case the value obtained in c)i) is below a control value established in the absence of wound exudate or wound biofilm, and the value obtained in c)ii) is below a control value established in the absence of wound exudate or wound biofilm, or identifying the skin wound as being a healing skin wound at said second time point in case the value obtained in c)i) is equal to or above a control value established in the absence of wound exudate or wound biofilm, and the value obtained in c)ii) is equal to or above a control value established in the absence of wound exudate or wound biofilm, e)
A) identifying a skin wound at a second time point to exhibit improved healing in case the value obtained in c)i) at said second time point is higher than the value obtained in a)i) at said first time point, and the value obtained in c)ii) at said second time point is higher than the value obtained in a)ii) at said first time point,
with the proviso that the values obtained in a)i) at said first time point and a)ii) at said first time point are equal to or below a respective control value established in the absence of wound exudate or wound biofilm,
or
B) identifying a skin wound at a second time point to exhibit worsened healing in case the value obtained in c)i) at said second time point is lower than the value obtained in a)i) at said first time point, and the value obtained in c)ii) at said second time point is lower than the value obtained in a)ii) at said first time point,
with the proviso that the values obtained in c)i) and c)ii) at said second time point are equal to or below 100% of a respective control value established in the absence of wound exudate or wound biofilm, and f) optionally repeating steps a) to e) at one or more later time points.

In one preferred embodiment of the present invention, the sample is a wound exudate sample. In another preferred embodiment, the sample is a wound biofilm sample. In a more preferred embodiment, the sample is a wound exudate sample.

For example, steps a) to e) may be repeated at two, three, four, five, six, seven, eight, nine, 10 or more later time points.

In one preferred embodiment, a skin wound at a second time point is identified to exhibit improved healing in case the value obtained in c)i) at said second time point is at least at least 10%, more preferably 15%, even more preferably 20%, 25%, 30%, 40% or 50% higher than the value obtained in a)i) at said first time point, and the value obtained in c)ii) at said second time point is at least 10%, more preferably 15%, even more preferably 20%, 25%, 30%, 40% or 50% higher than the value obtained in a)ii) at said first time point, with the proviso that the values obtained in a)i) at said first time point and a)ii) at said first time point are equal to or below a respective control value established in the absence of wound exudate or wound biofilm, preferably wherein the value(s) at said first time point is/are at least 10% below the respective control value, more preferably at least 15%, even more preferably at least 20%, 30%, 40% or 50% below the respective control value established in the absence of wound exudate or wound biofilm at said first time point, In another preferred embodiment, a skin wound at a second time point is identified to exhibit worsened healing in case the value obtained in c)i) at said second time point is at least at least 10%, more preferably 15%, even more preferably 20%, 25%, 30%, 40% or 50% lower than the value obtained in a)i) at said first time point, and the value obtained in c)ii) at said second time point is at least 10%, more preferably 15%, even more preferably 20%, 25%, 30%, 40% or 50% lower than the value obtained in a)ii) at said first time point, with the proviso that the values obtained in c)i) and c)ii) at said second time point are equal to or below 100% of a respective control value established in the absence of wound exudate or wound biofilm, preferably wherein the value(s) at said second time point is/are at least 10% below the respective control value, more preferably at least 15%, even more preferably at least 20%, 30%, 40% or 50% below the respective control value established in the absence of wound exudate or wound biofilm at said second time point.

Further, it was surprisingly found that an even more accurate and reliable monitoring can be achieved in case both assays relating to assays measuring the proliferation of primary fibroblast cells in the presence of wound exudate samples or wound biofilm samples obtained from a skin wound, and measuring the fibroblast-derived matrix formation by primary fibroblast cells in the presence of a wound exudate sample or wound biofilm sample are performed, and optionally the further assays relating to macrophage M1 and M2 markers and/or cytokine markers IL1alpha, IL1beta and/or TNFalpha, as described above.

Therefore, in another preferred embodiment, the method of the present invention comprises:

a) measuring
i) the proliferation of primary fibroblast cells in the presence of a wound exudate sample or wound biofilm sample obtained from said skin wound at a first time point, and
ii) the fibroblast-derived matrix formation by primary fibroblast cells in the presence of a wound exudate sample or wound biofilm sample obtained from said skin wound at a first time point,
and one, two, three or four of iiia), iiib), iiic) and iiid):
iiia) the proliferation of keratinocyte cells in the presence of a wound exudate sample or wound biofilm sample obtained from said skin wound at a first time point,
iiib) the amount(s) of one or more M1 marker(s) and one or more M2 marker(s) in the supernatant of macrophages incubated with a wound exudate sample or wound biofilm sample obtained from said skin wound at a first time point, wherein the macrophages are in co-culture with fibroblasts,
iiic) the amount(s) and/or frequency distribution(s) of one or more M1 cell surface marker(s) and one or more M2 cell surface marker(s) on macrophages incubated with a wound exudate sample or wound biofilm sample obtained from said skin wound at a first time point, wherein the macrophages are in co-culture with fibroblasts,
iiid) the expression level(s) of one or more M1 marker mRNA(s) and one or more M2 marker mRNA(s) in macrophages incubated with a wound exudate sample or wound biofilm sample obtained from said skin wound at a first time point, wherein the macrophages are in co-culture with fibroblasts, b) optionally identifying the skin wound as being a non-healing skin wound at said first time point or as a healing skin wound at a first time point pursuant to a method of the present invention, c) measuring
i) the proliferation of primary fibroblast cells in the presence of a wound exudate sample or wound biofilm sample obtained from said skin wound at a second time point, and ii) the fibroblast-derived matrix formation by primary fibroblast cells in the presence of a wound exudate sample or wound biofilm sample obtained from said skin wound at a second time point, and one two, three or four of iiia), iiib), iiic) and iiid):
iiia) the proliferation of keratinocyte cells in the presence of a wound exudate sample or wound biofilm sample obtained from said skin wound at a second time point,
iiib) the amount(s) of one or more M1 markers and one or more M2 markers in the supernatant of macrophages incubated with a wound exudate sample or wound biofilm sample obtained from said skin wound at a second time point, wherein the macrophages are in co-culture with fibroblasts,
iiic) the amount(s) and/or frequency distribution(s) of one or more M1 cell surface marker(s) and one or more M2 cell surface marker(s) on macrophages incubated with a wound exudate sample or wound biofilm sample obtained from said skin wound at a second time point, wherein the macrophages are in co-culture with fibroblasts,
iiid) the expression level(s) of one or more M1 marker mRNA(s) and one or more M2 marker mRNA(s) in macrophages incubated with a wound exudate sample or wound biofilm obtained from said skin wound at a second time point, wherein the macrophages are in co-culture with fibroblasts,
d) optionally identifying the skin wound as being a non-healing skin wound at said second time point or as a healing skin wound at said second time point pursuant to a method of the present invention,
e)
  A) identifying a skin wound at a second time point to exhibit improved healing in case at least two, preferably three, four, five or six of (1) to (6) are fulfilled:
    (1) the value obtained in c)i) at said second time point is higher than the value obtained in a)i) at said first time point,
    (2) the value obtained in c)ii) at said second time point is higher than the value obtained in a)ii) at said first time point,
    (3) the value obtained in c)iiia) at said second time point is higher than the value obtained in a)iiia) at said first time point,
    (4) the ratio of amount(s) of one or more M1 marker(s) to the amount(s) of one or more M2 marker(s) obtained in c)iiib) at said second time point is lower than the ratio of amount(s) of one or more M1 marker(s) to the amounts of one or more M2 markers obtained in a)iiib) at said first time point,
    (5) the ratio of amount(s) and/or frequency distribution(s) of one or more M1 cell surface marker(s) to the amount(s) and/or frequency distribution(s) of one or more M2 cell surface marker(s) obtained in c)iiic) at said second time point is lower than the ratio of amount(s) and/or frequency distribution(s) of one or more M1 cell surface marker(s) to the amount(s) and/or frequency distribution(s) of one or more M2 cell surface marker(s) obtained in a)iiic) at said first time point,
    (6) the ratio of expression level(s) of one or more M1 marker mRNA(s) to the expression level(s) of one or more M2 marker mRNA(s) obtained in c)iiid) at said second time point is lower than the ratio of expression level(s) of one or more M1 marker mRNA(s) to the expression level(s) of one or more M2 marker mRNA(s) obtained in a)iiid) at said first time point,
    with the proviso that at least the value(s) obtained in c)i) and/or c)ii) at said second time point is/are higher at said second time point than the value(s) obtained in a)i) and/or a)ii) at said first time point, and with the proviso that the value obtained in a)i) at said first time point and/or a)ii) at said first time point is equal to or below a control value established in the absence of wound exudate or wound biofilm,
    or
  B) identifying a skin wound at a second time point to exhibit worsened healing in case at least two, preferably three, four, five or six of (1) to (6) are fulfilled:
    (1) the value obtained in c)i) at said second time point is lower than the value obtained in a)i) at said first time point,
    (2) the value obtained in c)ii) at said second time point is lower than the value obtained in a)ii) at said first time point,
    (3) the value obtained in c)iiia) at said second time point is lower than the value obtained in a)iiia) at said first time point,
    (4) the ratio of amount(s) of one or more M1 marker(s) to the amount(s) of one or more M2 marker(s) obtained in c)iiib) at said second time point is higher than the ratio of amount(s) of one or more M1 marker(s) to the amounts of one or more M2 markers obtained in a)iiib) at said first time point,
    (5) the ratio of amount(s) and/or frequency distribution(s) of one or more M1 cell surface marker(s) to the amount(s) and/or frequency distribution(s) of one or more M2 cell surface marker(s) obtained in c)iiic) at said second time point is higher than the ratio of amount(s) and/or frequency distribution(s) of one or more M1 cell surface marker(s) to the amount(s) and/or frequency distribution(s) of one or more M2 cell surface marker(s) obtained in a)iiic) at said first time point,
    (6) the ratio of expression level(s) of one or more M1 marker mRNA(s) to the expression level(s) of one or more M2 marker mRNA(s) obtained in c)iiid) at said second time point is higher than the ratio of expression level(s) of one or more M1 marker mRNA(s) to the expression level(s) of one or more M2 marker mRNA(s) obtained in a)iiid) at said first time point,
    with the proviso that at least the value(s) obtained in c)i) and/or c)ii) at said second time point is/are lower than the value(s) obtained in a)i) and/or a)ii) at said first time point, and
    with the proviso that the value(s) obtained in c)i) and/or c)ii) at said second time point is/are equal to or below 100% of a control value established in the absence of wound exudate or wound biofilm,
  and
f) optionally repeating steps a) to e) at one or more later time points.

Therefore, in yet another preferred embodiment, the method of the present invention comprises:
a) measuring
  i) the proliferation of primary fibroblast cells in the presence of a wound exudate sample or wound biofilm sample obtained from said skin wound at a first time point, and
  ii) the fibroblast-derived matrix formation by primary fibroblast cells in the presence of a wound exudate sample or wound biofilm sample obtained from said skin wound at a first time point, and one, two, three or four of iiia), iiib), iiic) and iiid), or one, two, three, four or five of iiia), iiib), iiic), iiid) and iiie):

iiia) the proliferation of HaCaT cells in the presence of a wound exudate sample or wound biofilm sample obtained from said skin wound at a first time point, iiib) the amount(s) of one or more M1 marker(s) and one or more M2 marker(s) in the supernatant of macrophages incubated with a wound exudate sample or wound biofilm sample obtained from said skin wound at a first time point, wherein the macrophages are in co-culture with fibroblasts, wherein the one or more M1 markers are selected from CXCL10 and IL-23p19, and the one or more M2 markers are selected from CCL22 and CCL18, iiic) the amount(s) and/or frequency distribution(s) of one or more M1 cell surface marker(s) and one or more M2 cell surface marker(s) on macrophages incubated with a wound exudate sample or wound biofilm sample obtained from said skin wound at a first time point, wherein the macrophages are in co-culture with fibroblasts, wherein the one or more M1 cell surface marker are selected from CD38, CD64 and CD197, and wherein the one or more M2 cell surface markers are selected from CD200 receptor, CD206 and CD209, iiid) the expression level(s) of one or more M1 marker mRNA(s) and one or more M2 marker mRNA(s) in macrophages incubated with a wound exudate sample or wound biofilm sample obtained from said skin wound at a first time point, wherein the macrophages are in co-culture with fibroblasts, iiie) the amount(s) of one or more cytokine markers in the supernatant of macrophages incubated with a wound exudate sample or wound biofilm sample obtained from said skin wound at a first time point, wherein the macrophages are in co-culture with fibroblasts, and wherein the one or more cytokine markers are selected from IL-1alpha, IL-1 beta and TNF-alpha, b) optionally identifying the skin wound as being a non-healing skin wound at said first time point or as a healing skin wound at a first time point pursuant to a method of the present invention, c) measuring
i) the proliferation of primary fibroblast cells in the presence of a wound exudate sample or wound biofilm sample obtained from said skin wound at a second time point, and
ii) the fibroblast-derived matrix formation by primary fibroblast cells in the presence of a wound exudate sample or wound biofilm sample obtained from said skin wound at a second time point, and one two, three or four of iiia), iiib), iiic) and iiid), or one, two, three, four or five of iiia), iiib), iiic), iiid) and iiie):

iiia) the proliferation of HaCaT cells in the presence of a wound exudate sample or wound biofilm sample obtained from said skin wound at a second time point, iiib) the amount(s) of one or more M1 markers and one or more M2 markers in the supernatant of macrophages incubated with a wound exudate sample or wound biofilm sample obtained from said skin wound at a second time point, wherein the macrophages are in co-culture with fibroblasts, wherein the one or more M1 markers are selected from CXCL10 and IL-23p19, and the one or more M2 markers are selected from CCL22 and CCL18, iiic) the amount(s) and/or frequency distribution(s) of one or more M1 cell surface marker(s) and one or more M2 cell surface marker(s) on macrophages incubated with a wound exudate sample or wound biofilm sample obtained from said skin wound at a second time point, wherein the macrophages are in co-culture with fibroblasts, wherein the one or more M1 cell surface marker are selected from CD38, CD64 and CD197, and wherein the one or more M2 cell surface markers are selected from CD200 receptor, CD206 and CD209, iiid) the expression level(s) of one or more M1 marker mRNA(s) and one or more M2 marker mRNA(s) in macrophages incubated with a wound exudate sample or wound biofilm sample obtained from said skin wound at a second time point, wherein the macrophages are in co-culture with fibroblasts, wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18, iiie) the amount(s) of one or more cytokine markers in the supernatant of macrophages incubated with a wound exudate sample or wound biofilm sample obtained from said skin wound at a second time point, wherein the macrophages are in co-culture with fibroblasts, and wherein the one or more cytokine markers are selected from IL-1alpha, IL-1 beta and TNF-alpha, d) optionally identifying the skin wound as being a non-healing skin wound at said second time point or as a healing skin wound at said second time point pursuant to a method of the present invention, e)
A) identifying a skin wound at a second time point to exhibit improved healing in case at least two, preferably three, four, five or six of (1) to (6), or at least two, preferably three, four, five, six or seven of (1) to (7) are fulfilled:

(1) the value obtained in c)i) at said second time point is higher than the value obtained in a)i) at said first time point, (2) the value obtained in c)ii) at said second time point is higher than the value obtained in a)ii) at said first time point, (3) the value obtained in c)iiia) at said second time point is higher than the value obtained in a)iiia) at said first time point, (4) the ratio of amount(s) of one or more M1 marker(s) to the amount(s) of one or more M2 marker(s) obtained in c)iiib) at said second time point is lower than the ratio of amount(s) of one or more M1 marker(s) to the amounts of one or more M2 markers obtained in a)iiib) at said first time point,
wherein the one or more M1 markers are selected from CXCL10 and IL-23p19, and the one or more M2 markers are selected from CCL22 and CCL18

(5) the ratio of amount(s) and/or frequency distribution(s) of one or more M1 cell surface marker(s) to the amount(s) and/or frequency distribution(s) of one or more M2 cell surface marker(s) obtained in c)iiic) at said second time point is lower than the ratio of amount(s) and/or frequency distribution(s) of one or more M1 cell surface marker(s) to the amount(s) and/or frequency distribution(s) of one or more M2 cell surface marker(s) obtained in a)iiic) at said first time point, wherein the one or more M1 cell surface markers are selected from CD38, CD64 and CD197, and wherein the M2 cell surface markers are selected from CD200 receptor, CD206 and CD209, in particular wherein the ratio is selected from a CD38/ CD209 ratio, a CD197/CD209 ratio and a CD197/ CD206 ratio, (6) the ratio of expression level(s) of one or more M1 marker mRNA(s) to the expression level(s) of one or more M2 marker mRNA(s) obtained in c)iiid) at said second time point is lower than the ratio of expression level(s) of one or more M1 marker mRNA(s) to the expression level(s) of one or more M2 marker mRNA(s) obtained in a)iiid) at said first time point, wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18, (7) the value obtained in c)iiie) at said second time point is lower than the value obtained in a)iiie) at said first time point, with the proviso that at least the value(s) obtained in c)i) and/or c)ii) at said second time point is/are higher at said second time point than the value(s) obtained in a)i) and/or a)ii) at said first time point, and with the proviso that the value obtained in a)i) at said first time point and/or a)ii) at said first time point is equal to or below a control value established in the absence of wound exudate or wound biofilm, or B) identifying a skin wound at a second time point to exhibit worsened healing in case at least two, preferably three, four, five or six of (1) to (6), or at least two, preferably three, four, five, six or seven of (1) to (7) are fulfilled:

(1) the value obtained in c)i) at said second time point is lower than the value obtained in a)i) at said first time point, (2) the value obtained in c)ii) at said second time point is lower than the value obtained in a)ii) at said first time point, (3) the value obtained in c)iiia) at said second time point is lower than the value obtained in a)iiia) at said first time point, (4) the ratio of amount(s) of one or more M1 marker(s) to the amount(s) of one or more M2 marker(s) obtained in c)iiib) at said second time point is higher than the ratio of amount(s) of one or more M1 marker(s) to the amounts of one or more M2 markers obtained in a)iiib) at said first time point, wherein the one or more M1 markers are selected from CXCL10 and IL 23p19, and the one or more M2 markers are selected from CCL22 and CCL18, in particular wherein the ratio is selected from a CD38/ CD209 ratio, a CD197/CD209 ratio and a CD197/ CD206 ratio, (5) the ratio of amount(s) and/or frequency distribution(s) of one or more M1 cell surface marker(s) to the amount(s) and/or frequency distribution(s) of one or more M2 cell surface marker(s) obtained in c)iiic) at said second time point is higher than the ratio of amount(s) and/or frequency distribution(s) of one or more M1 cell surface marker(s) to the amount(s) and/or frequency distribution(s) of one or more M2 cell surface marker(s) obtained in a)iiic) at said first time point, wherein the one or more M1 cell surface markers are selected from CD38, CD64 and CD197, and wherein the one or more M2 cell surface markers are selected from CD200 receptor, CD206 and CD209, (6) the ratio of expression level(s) of one or more M1 marker mRNA(s) to the expression level(s) of one or more M2 marker mRNA(s) obtained in c)iiid) at said second time point is higher than the ratio of expression level(s) of one or more M1 marker mRNA(s) to the expression level(s) of one or more M2 marker mRNA(s) obtained in a)iiid) at said first time point, wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18, (7) the value obtained in c)iiie) at said second time point is higher than the value obtained in a)iiie) at said first time point, with the proviso that at least the value(s) obtained in c)i) and/or c)ii) at said second time point is/are lower than the value(s) obtained in a)i) and/or a)ii) at said first time point, and with the proviso that the value(s) obtained in c)i) and/or c)ii) at said second time point is/are equal to or below 100% of a control value established in the absence of wound exudate or wound biofilm, and f) optionally repeating steps a) to e) at one or more later time points In one preferred embodiment of the present invention, the sample is a wound exudate sample. In another preferred embodiment, the sample is a wound biofilm sample. In a more preferred embodiment, the sample is a wound exudate sample.

In one preferred embodiment of the method of the present invention, steps a) and c) comprise measuring one, two or three or four of iiia), iiib), iiic) and iiie). In such preferred embodiment, a skin wound is identified in step e)A) at a second time point to exhibit improved healing in case at least two, preferably three, four, five or six of (1) to (5) and (7) for improved wound healing are fulfilled, with the proviso that at least the value(s) obtained in c)i) and/or c)ii) at said second time point is/are higher at said second time point than the value(s) obtained in a)i) and/or a)ii) at said first time point, and with the proviso that the value obtained in a)i) at said first time point and/or a)ii) at said first time point is equal to or below a control value established in the absence of wound exudate or wound biofilm. Further, in such preferred embodiment, a skin wound is identified in step e)B) at a second time point to exhibit worsened healing in case at least two, preferably three, four, five or six of (1) to (5) and (7) for worsened skin wound healing are fulfilled, with the proviso that at least the value(s) obtained in c)i) and/or c)ii) at said second time point is/are lower than the value(s) obtained in a)i) and/or a)ii) at said first time point, and with the proviso that the value(s) obtained in c)i) and/or c)ii) at said second time point is/are equal to or below 100% of a control value established in the absence of wound exudate or wound biofilm.

In one preferred embodiment, a skin wound at a second time point is identified to exhibit improved healing in case at least two, preferably three, four, five or six of (1) to (6) or at least two, preferably three, four, five, six or seven of (1) to (7) or at least two, preferably three, four, five or six of (1) to (5) and (7) for improved healing are fulfilled, preferably wherein the value obtained in c)i) at said second time point is at least at least 10%, more preferably 15%, even more preferably 20%, 25%, 30%, 40% or 50% higher than the value obtained in a)i) at said first time point, and/or the value obtained in c)ii) at said second time point is at least 10%, more preferably 15%, even more preferably 20%, 25%, 30%, 40% or 50% higher than the value obtained in a)ii) at said first time point,
with the proviso that the values obtained in a)i) at said first time point and/or a)ii) at said first time point are equal to or below a respective control value established in the absence of wound exudate or wound biofilm, preferably wherein the value(s) at said first time point is/are at least 10% below the respective control value, more preferably at least 15%, even more preferably at least 20%, 30%, 40% or 50% below the respective control value established in the absence of wound exudate or wound biofilm at said first time point.

Preferably, the sample is a wound exudate sample.

In one more preferred embodiment, a skin wound at a second time point is identified to exhibit improved healing in case at least two, preferably three, four, five or six of (1) to (6) or at least two, preferably three, four, five, six or seven of (1) to (7) or at least two, preferably three, four, five or six of (1) to (5) and (7) for improved healing are fulfilled, preferably wherein the value obtained in c)i) at said second time point is at least at least 10%, more preferably 15%, even more preferably 20%, 25%, 30%, 40% or 50% higher than the value obtained in a)i) at said first time point, and the value obtained in c)ii) at said second time point is at least 10%, more preferably 15%, even more preferably 20%, 25%, 30%, 40% or 50% higher than the value obtained in a)ii) at said first time point,
with the proviso that the values obtained in a)i) at said first time point and a)ii) at said first time point are equal to or below a respective control value established in the absence of wound exudate or wound biofilm, preferably wherein the values at said first time point are at least 10% below the respective control value, more preferably at least 15%, even more preferably at least 20%, 30%, 40% or 50% below the respective control value established in the absence of wound exudate or wound biofilm at said first time point.

In another preferred embodiment, a skin wound at a second time point is identified to exhibit worsened healing in case healing in case at least two, preferably three, four, five or six of (1) to (6) or at least two, preferably three, four, five, six or seven of (1) to (7) or at least two, preferably three, four, five or six of (1) to (5) and (7) for worsened wound healing are fulfilled, preferably wherein the value obtained in c)i) at said second time point is at least at least 10%, more preferably 15%, even more preferably 20%, 25%, 30%, 40% or 50% lower than the value obtained in a)i) at said first time point, and/or the value obtained in c)ii) at said second time point is at least 10%, more preferably 15%, even more preferably 20%, 25%, 30%, 40% or 50% lower than the value obtained in a)ii) at said first time point,
with the proviso that the values obtained in c)i) and/or c)ii) at said second time point are equal to or below 100% of a respective control value established in the absence of wound exudate or wound biofilm, preferably wherein the value(s) at said second time point is/are at least 10% below a respective control value, more preferably at least 15%, even more preferably at least 20%, 30%, 40% or 50% below a respective control value established in the absence of wound exudate or wound biofilm at said second time point.

In another more preferred embodiment, a skin wound at a second time point is identified to exhibit worsened healing in case healing in case at least two, preferably three, four, five or six of (1) to (6) or at least two, preferably three, four, five, six or seven of (1) to (7) or at least two, preferably three, four, five or six of (1) to (5) and (7) for worsened wound healing are fulfilled, preferably wherein the value obtained in c)i) at said second time point is at least at least 10%, more preferably 15%, even more preferably 20%, 25%, 30%, 40% or 50% lower than the value obtained in a)i) at said first time point, and the value obtained in c)ii) at said second time point is at least 10%, more preferably 15%, even more preferably 20%, 25%, 30%, 40% or 50% lower than the value obtained in a)ii) at said first time point,
with the proviso that the values obtained in c)i) and c)ii) at said second time point are equal to or below 100% of a respective control value established in the absence of wound exudate or wound biofilm, preferably wherein the values at said second time point are at least 10% below a respective control value, more preferably at least 15%, even more preferably at least 20%, 30%, 40% or 50% below a respective control value established in the absence of wound exudate or wound biofilm at said second time point.

Further, it is preferred to perform at least the three assays measuring the proliferation of primary fibroblast cells, measuring the fibroblast-derived matrix formation by primary fibroblast cells and measuring the proliferation of keratinocyte cells at said first and second time point. Therefore, in yet another preferred embodiment of a method of the invention, the method steps a)i), a)ii) and a)iii) at said first time point, and c)i), c)ii) and c)iii) at said second time point are performed.

In one more preferred embodiment, a skin wound at a second time point is identified to exhibit improved healing in case at least two, preferably three of (1) to (3) for improved healing are fulfilled, preferably wherein the value obtained in c)i) at said second time point is at least at least 10%, more preferably 15%, even more preferably 20%, 25%, 30%, 40% or 50% higher than the value obtained in a)i) at said first time point, and/or the value obtained in c)ii) at said second time point is at least 10%, more preferably 15%, even more preferably 20%, 25%, 30%, 40% or 50% higher than the value obtained in a)ii) at said first time point, and/or the value obtained in c)iiia) at said second time point is at least 10%, more preferably 15%, even more preferably 20%, 25%, 30%, 40% or 50% higher than the value obtained in a)iiia) at said first time point,
with the proviso that the values obtained in a)i) at said first time point and/or a)ii) at said first time point and/or a)iiia) at said first time point are equal to or below a respective control value established in the absence of wound exudate or wound biofilm, preferably wherein the value(s) at said first time point is/are at least 10% below the respective control value, more preferably at least 15%, even more preferably at least 20%, 30%, 40% or 50% below the respective control value established in the absence of wound exudate or wound biofilm at said first time point.

In one more preferred embodiment, a skin wound at a second time point is identified to exhibit improved healing in case at least two, preferably three of (1) to (3) for improved healing are fulfilled, preferably wherein the value obtained in c)i) at said second time point is at least at least 10%, more preferably 15%, even more preferably 20%, 25%, 30%, 40% or 50% higher than the value obtained in a)i) at said first time point, and the value obtained in c)ii) at said second time point is at least 10%, more preferably 15%, even more preferably 20%, 25%, 30%, 40% or 50% higher than the value obtained in a)ii) at said first time point, and/or the value obtained in c)iiia) at said second time point is at least 10%, more preferably 15%, even more preferably 20%, 25%, 30%, 40% or 50% higher than the value obtained in a)iiia) at said first time point
with the proviso that the values obtained in a)i) at said first time point and a)ii) at said first time point and/or a)iiia) at said first time point are equal to or below a respective control value established in the absence of wound exudate or wound biofilm, preferably wherein the values at said first time point are at least 10% below the respective control value, more preferably at least 15%, even more preferably at least 20%, 30%, 40% or 50% below the respective control value established in the absence of wound exudate or wound biofilm at said first time point.

In another preferred embodiment, a skin wound at a second time point is identified to exhibit worsened healing in case healing in case at least two, preferably three of (1) to (6) or at least two, preferably three of (1) to (7) or at least two, preferably three of (1) to (5) and (7) for worsened wound healing are fulfilled, preferably wherein the value obtained in c)i) at said second time point is at least at least 10%, more preferably 15%, even more preferably 20%, 25%, 30%, 40% or 50% lower than the value obtained in a)i) at said first time point, and/or the value obtained in c)ii) at said second time point is at least 10%, more preferably 15%, even more preferably 20%, 25%, 30%, 40% or 50% lower than the value obtained in a)ii) at said first time point, and/or the value obtained in c)iiia) at said second time point is at least 10%, more preferably 15%, even more preferably 20%, 25%, 30%, 40% or 50% lower than the value obtained in a)iiia) at said first time point,
with the proviso that the values obtained in c)i) and/or c)ii) and/or c)iiia) at said second time point are equal to or below 100% of a respective control value established in the absence of wound exudate or wound biofilm, preferably wherein the value(s) at said second time point is/are at least 10% below a respective control value, more preferably at least 15%, even more preferably at least 20%, 30%, 40% or 50% below a respective control value established in the absence of wound exudate or wound biofilm at said second time point.

In another more preferred embodiment, a skin wound at a second time point is identified to exhibit worsened healing in case healing in case at least two, preferably three of (1) to (3) for worsened wound healing are fulfilled, preferably wherein the value obtained in c)i) at said second time point is at least at least 10%, more preferably 15%, even more preferably 20%, 25%, 30%, 40% or 50% lower than the value obtained in a)i) at said first time point, and the value obtained in c)ii) at said second time point is at least 10%, more preferably 15%, even more preferably 20%, 25%, 30%, 40% or 50% lower than the value obtained in a)ii) at said first time point, and/or the value obtained in c)iiia) at said second time point is at least 10%, more preferably 15%, even more preferably 20%, 25%, 30%, 40% or 50% lower than the value obtained in a)iiia) at said first time point,
with the proviso that the values obtained in c)i) and c)ii) and/or c)iiia) at said second time point are equal to or below 100% of a respective control value established in the absence of wound exudate or wound biofilm, preferably wherein the values at said second time point are at least 10% below a respective control value, more preferably at least 15%, even more preferably at least 20%, 30%, 40% or 50% below a respective control value established in the absence of wound exudate or wound biofilm at said second time point.

In one preferred embodiment of any method of the invention described herein, the individual is a mammal, more preferably a human.

In another preferred embodiment of any method of the invention described herein, a skin wound is selected from a wound of a diabetic patient, a wound which is infected by at least one microorganism, an ischemic wound, a wound in a patient suffering from deficient blood supply or venous stasis, an ulcer, such a diabetic ulcer, venous ulcer, arterial ulcer (e.g. ulcus cruris arteriosum), mixed ulcer, or pressure ulcer, a neuropathic wound, ulcus cruris, surgical wound, burn, dehiscence, neoplastic ulcer and rare ulcer.

As described in the examples, such wounds have a high risk for developing into chronic skin wounds and/or non-healing skin wounds and/or to exhibit worsened wound healing. Such skin wounds can in particular benefit from the methods of the present invention. In another preferred embodiment of any method of the invention described herein, a non-healing skin wound is understood as a wound which does not close within 2 months under standard therapy.

In another preferred embodiment of any method of the invention described herein, the individual exhibits further diseases and/or co-morbidities, and/or is treated with medication(s) for further diseases and/or co-morbidities. As described in the examples, such individuals may have a risk for developing chronic skin wounds and/or non-healing skin wounds and/or to exhibit worsened wound healing. Such skin wounds can in particular benefit from the methods of the present invention.

In another preferred embodiment of a method of the invention described herein, the skin wound is untreated or treated with one or more of the following: compression, wound dressings, surgical debridement, biological debridement, infection control, antibiotic therapy, negative pressure therapy, proteins, in particular growth factors, antibodies, peptides, sugars, cells or cell constituents, artificial skin, human blood-derived products, gene therapy or genetically engineered wound bed modifications, drugs, herbal medicines, plant extracts.

In another preferred embodiment of a method of the invention described herein, the individual is identified to be treated with one or more of the therapies selected from compression, wound dressings, surgical debridement, biological debridement, infection control, antibiotic therapy, negative pressure therapy, proteins, in particular growth factors, antibodies, peptides, sugars, cells or cell constituents, artificial skin, human blood-derived products, gene therapy or genetically engineered wound bed modifications, drugs, herbal medicines, plant extracts, in case (i) a skin wound of the individual is identified as being a non-healing skin wound by a method for identifying a skin wound in an individual as being a non-healing skin wound or healing skin wound of the present invention, and/or a skin wound of the individual is identified to exhibit worsened healing at a second time point as compared to a first time point by a method for monitoring skin wound healing of the present invention.

Therefore, in a yet further embodiment, the present invention relates to a method of treating a non-healing skin wound in an individual, comprising administering to an individual one or more of the therapies selected from compression, wound dressings, surgical debridement, biological debridement, infection control, antibiotic therapy, negative pressure therapy, proteins, in particular growth factors, antibodies, peptides, sugars, cells or cell constituents, artificial skin, human blood-derived products, gene therapy or genetically engineered wound bed modifications, drugs, herbal medicines, plant extracts, wherein the individual is identified to have at least one non-healing skin wound by performing a method of the present invention.

Therefore, in a yet further embodiment, the present invention relates to a method of treating a skin wound in an individual which exhibits worsened healing, comprising administering to an individual one or more of the therapies selected from compression, wound dressings, surgical debridement, biological debridement, infection control, antibiotic therapy, negative pressure therapy, proteins, in particular growth factors, antibodies, peptides, sugars, cells or cell constituents, artificial skin, human blood-derived products, gene therapy or genetically engineered wound bed modifications, drugs, herbal medicines, plant extracts, wherein the individual is identified to have at least one skin wound which exhibits worsened wound healing by performing a method of the present invention.

For therapies which involve administration of at least one active agent, such as antibiotic therapy, proteins, in particular growth factors, antibodies, peptides, sugars, cells or cell constituents, artificial skin, human blood-derived products, gene therapy or genetically engineered wound bed modifications, drugs, herbal medicines, and plant extracts, a therapeutically effective amount is administered to the individual. Preferably, such at least one active agent is comprised in a pharmaceutical composition which may further comprise at least one pharmaceutically acceptable carrier or excipient. The therapeutically effective amount depends on the nature of the agent and is known to a skilled person. Further, at least one active agent may be administered once or repeatedly.

In another preferred embodiment of any method of the invention described herein, the wound exudate sample is obtained by a physical or chemical method, in particular by applying negative pressure to the skin wound, in particular by using a negative pressure drainage device, a method using capillary forces, collecting wound exudate in a film dressing or membrane, collecting wound exudate in a syringe, applying an absorptive material, such as absorptive beads, or a filter, or by using a swab, such as a cotton swab, in particular wherein the film dressing or membrane is a cellulose layer and/or wherein the absorptive material is a cellulose layer. In the examples, negative pressure was applied to the skin wound in order to obtain a wound exudate sample.

In another preferred embodiment of any method of the invention described herein, a healing skin wound is characterized by ongoing wound closure, granulation, absence of necrosis and/or absence of infections.

In another preferred embodiment of any method of the invention described herein, a non-healing skin wound is characterized by a lack of wound closure, an increase of the area and/or depth of the wound, necrosis and/or infections of the skin wound, and/or lack of granulation.

In another preferred embodiment of a method of the invention described herein, the fibroblast and/or monocyte cells used in the methods are human cells, preferably human cells and/or primary cells obtained from healthy human individuals, from patients with comorbidities associated with impaired wound healing, such as diabetes, and/or from the individual patients providing the wound exudates.

In another preferred embodiment of a method of the invention described herein, the wound exudate sample is diluted between 1:2 to 1:1000, preferably between 1:10 and 1:200 or 1:20 to 1:100. For example, dilutions of 1:25 or 1:50, such as dilutions in medium were successfully used. The wound exudate sample is preferably diluted in an aqueous liquid, such as aqueous solution or suspension. In a preferred embodiment, the wound exudate sample is diluted in a cell medium, such as DMEM containing FCS. Also, an aqueous saline solution, such as an aqueous buffered saline solution may be used. Preferably, the wound exudate sample is diluted in an aqueous liquid, which does not substantially interfere with the viability of the cells used in the assays of the methods of the invention.

In another preferred embodiment of a method of the invention described herein, the wound biofilm sample is diluted between 1:2 to 1:1000, preferably between 1:10 and 1:200 or 1:20 to 1:100. The wound biofilm sample is preferably diluted in an aqueous liquid, such as aqueous solution or suspension. In a preferred embodiment, the wound biofilm sample is diluted in a cell medium, such as DMEM containing FCS. Also, an aqueous saline solution, such as an aqueous buffered saline solution may be used. Preferably, the wound biofilm sample is diluted in an aqueous liquid, which does not substantially interfere with the viability of the cells used in the assays of the methods of the invention.

In one preferred embodiment of a method of the invention, measuring the proliferation of primary fibroblast cells in the presence of a wound exudate sample or wound biofilm sample obtained from a skin wound includes the following steps:

(i) culturing primary human dermal fibroblast cells,
(ii) incubating the cells on a solid support, thereby allowing the cells to adhere to the support,
(iii) contacting the cells with the wound exudate sample or wound biofilm sample, which is optionally diluted, wherein the contacting may be performed before or after adherence of the cells occurs,
(iv) determining the amount, preferably the cell number, including the formation of extracellular matrix, of the primary fibroblast cells, such as by fixing cells and determining total protein content, preferably wherein the method is performed in 2D cell culture.

In one preferred embodiment of a method of the invention, measuring the fibroblast-derived matrix formation by primary fibroblast cells in the presence of a wound exudate sample or wound biofilm sample obtained from a skin wound includes the following steps:

(i) seeding primary human dermal fibroblast cells on a support, which is preferably pre-coated with an adhesion enhancing agent, such as gelatin,
(ii) culturing the cells on the support, preferably until confluence is reached,
(iii) contacting the cells with (i) a matrix promoting supplement, and (ii) the wound exudate sample or wound biofilm sample, which is optionally diluted, wherein (i) and (ii) may be contacted simultaneously or sequentially,
(iv) determining the amount of the fibroblast-derived matrix, such as by fixing cells and determining total protein content, preferably wherein the method is performed in 3D cell culture.

In one preferred embodiment of a method of the invention, measuring the proliferation of keratinocyte cells in the presence of a wound exudate sample or wound biofilm sample obtained from a skin wound includes the following steps:

(i) culturing keratinocyte cells,
(ii) incubating the cells on a solid support, thereby allowing the cells to adhere to the support,
(iii) contacting the cells with the wound exudate sample or wound biofilm sample, which is optionally diluted, wherein the contacting may be performed before or after adherence of the cells occurs,
(iv) determining the amount, preferably the cell number, of the keratinocyte cells, such as by fixing cells and determining total protein content, preferably wherein the method is performed in 2D cell culture.

In one preferred embodiment of a method of the invention, measuring the amount(s) of one or more M1 marker(s) and one or more M2 marker(s) in the supernatant of macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample or wound biofilm sample, which is optionally diluted,
(iv) determining the amount of one or more M1 markers and one or more M2 markers in the cell culture supernatant,
preferably wherein the one or more M1 markers are selected from CXCL10 and IL-23p19, and/or the one or more M2 markers are selected from CCL22 and CCL18, more preferably wherein the markers are determined by using an immunological assay, even more preferably by using an ELISA assay.

In one preferred embodiment of a method of the invention, measuring the amount(s) and/or frequency distribution(s) of one or more M1 cell surface marker(s) and one or more M2 cell surface marker(s) on macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample or wound biofilm sample, which is optionally diluted,
(iv) determining the amount(s) and/or frequency distribution(s) of one or more M1 marker(s) and one or more M2 marker(s) on the cell surface of macrophages,
preferably wherein the one or more M1 cell surface markers are selected from CD38, CD64 and CD197, and/or the one or more M2 cell surface markers are selected from CD200 receptor (CD200R), CD206 and CD209, more preferably wherein the amount(s) and/or frequency distribution(s) of the cell surface markers are determined by an immunological assay and/or a fluorescence assay, in particular by FACS analysis,
even more preferably wherein step iv) includes:
contacting the macrophages with binding agents, preferably antibodies, which specifically recognize one or more M1 cell surface marker(s) and one or more M2 cell surface marker(s), wherein the binding agents are optionally labelled, in particular labelled with a fluorescent label, and determining the amounts of binding molecules bound to the macrophages, in particular by determining mean fluorescence intensity, thereby determining the amount(s) of the cell surface markers,
and/or
contacting the macrophages with binding agents, preferably antibodies, which specifically recognize one or more M1 cell surface marker(s) and one or more M2 cell surface marker(s), wherein the binding agents are optionally labelled, in particular labelled with a fluorescent label, and determining the percentages of cells which are positive for the one or more M1 cell surface marker(s) and the one or more M2 cell surface marker(s), respectively, within a cell population, in particular wherein FACS analysis is performed, thereby determining the frequency distribution(s) of the cell surface markers.

In one preferred embodiment of a method of the invention, measuring the expression level(s) of one or more M1 marker mRNA(s) and one or more M2 marker mRNA(s) in macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample or wound biofilm sample, which is optionally diluted,
(iv) determining the expression level(s) of one or more M1 marker mRNA(s) and one or more M2 marker mRNA(s) in the macrophages,
preferably wherein the one or more M1 marker mRNA(s) are selected from CD38, CD64, CD197, CXCL10 and IL-23p19, and/or the one or more M2 marker mRNA(s) are selected from CD200 receptor (CD200R), CD206, CD209, CCL22 and CCL18, more preferably wherein the method comprises contacting a probe which specifically binds to a marker mRNA, wherein the probe is optionally labelled, with the macrophage RNA under conditions which are conducive to hybridization, and detecting the hybridized probe.

In one preferred embodiment of the present invention, the sample is a wound exudate sample. In another preferred embodiment, the sample is a wound biofilm sample. In a more preferred embodiment, the sample is a wound exudate sample.

In one preferred embodiment, measuring the amount(s) of one or more cytokine markers selected from IL-1alpha, IL-1beta and TNF-alpha in the supernatant of macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample or wound biofilm sample, which is optionally diluted,
(iv) determining the amount of one or more cytokine markers selected from IL-1alpha, IL-1 beta and TNF-alpha in the cell culture supernatant.

In one preferred embodiment, the cytokine markers are determined by using an immunological assay, more preferably by using an ELISA assay.

In one preferred embodiment of the present invention, the sample is a wound exudate sample. In another preferred embodiment, the sample is a wound biofilm sample. In a more preferred embodiment, the sample is a wound exudate sample.

Further, it is preferred that two or more assays performed in the methods of the present invention are performed simultaneously, even more preferably wherein the method steps are performed on a single support. In such embodiment, a wound-on-a-chip test method is provided. Thereby, the demands of clinicians are met.

In a preferred embodiment of a method of the invention described herein, the following method steps are performed simultaneously:
i) measuring the proliferation of primary fibroblast cells in the presence of a wound exudate sample or wound biofilm sample obtained from a skin wound, and
ii) measuring the fibroblast-derived matrix formation by primary fibroblast cells in the presence of a wound exudate sample or wound biofilm sample obtained from a skin wound,
and optionally
iiia) measuring the proliferation of keratinocyte cells in the presence of a wound exudate sample or wound biofilm sample obtained from a skin wound, and/or
iiib) measuring the amount(s) of one or more M1 marker(s) and one or more M2 marker(s) in the supernatant of macrophages incubated with a wound exudate sample or wound biofilm sample obtained from a skin wound, wherein the macrophages are in co-culture with fibroblasts, and/or
iiic) measuring the amount(s) and/or frequency distribution(s) of one or more M1 cell surface marker(s) and one or more M2 cell surface marker(s) on macrophages incubated with a wound exudate sample or wound biofilm sample obtained from a skin wound, wherein the macrophages are in co-culture with fibroblasts, and/or
iiid) measuring the expression level(s) of one or more M1 marker mRNA(s) and one or more M2 marker mRNA(s) in macrophages incubated with a wound exudate sample or wound biofilm sample obtained from a skin wound, wherein the macrophages are in co-culture with fibroblasts,
preferably wherein the method steps are performed on a single support, more preferably wherein the support is a chip, array, such as a microarray or nanoarray, a plate, such as a multiwell plate, or a dish.

In another preferred embodiment of a method of the invention described herein, the following method steps are performed simultaneously:
i) measuring the proliferation of primary fibroblast cells in the presence of a wound exudate sample or wound biofilm sample obtained from a skin wound, and
ii) measuring the fibroblast-derived matrix formation by primary fibroblast cells in the presence of a wound exudate sample or wound biofilm sample obtained from a skin wound,
and optionally
iiia) measuring the proliferation of keratinocyte cells in the presence of a wound exudate sample or wound biofilm sample obtained from a skin wound, and/or
iiib) measuring the amount(s) of one or more M1 marker(s) and one or more M2 marker(s) in the supernatant of macrophages incubated with a wound exudate sample or wound biofilm sample obtained from a skin wound, wherein the macrophages are in co-culture with fibroblasts, wherein the one or more M1 markers are selected from CXCL10 and IL-23p19, and the one or more M2 markers are selected from CCL22 and CCL18, and/or
iiic) measuring the amount(s) and/or frequency distribution(s) of one or more M1 cell surface marker(s) and one or more M2 cell surface marker(s) on macrophages incubated with a wound exudate sample or wound biofilm sample obtained from a skin wound, wherein the macrophages are in co-culture with fibroblasts, wherein the one or more M1 cell surface markers are selected from CD38, CD64 and CD197, and wherein the one or more M2 cell surface marker are selected from CD200 receptor, CD206 and CD209, and/or
iiid) measuring the expression level(s) of one or more M1 marker mRNA(s) and one or more M2 marker mRNA(s) in macrophages incubated with a wound exudate sample or wound biofilm sample obtained from a skin wound, wherein the macrophages are in co-culture with fibroblasts, wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18,
and/or
iiie) measuring the amount(s) of one or more cytokine markers in the supernatant of macrophages incubated with a wound exudate sample or wound biofilm sample obtained from a skin wound, wherein the macrophages are in co-culture with fibroblasts, and wherein the one or more cytokine markers are selected from IL-1alpha, IL-1beta and TNF-alpha,
preferably wherein the method steps are performed on a single support, more preferably wherein the support is a chip, array, such as a microarray or nanoarray, a plate, such as a multiwell plate, or a dish.

"Simultaneously" is understood to mean that the method steps relating to the assays are at least partially overlapping in time.

Preferably, the method steps of any method of the invention are performed on a single support, more preferably wherein the support is a chip, array, such as a microarray or nanoarray, a plate, such as a multiwell plate, or a dish. The solid support preferably contains at least one, preferably a plurality of defined areas or cavities, more preferably at least one, even more preferably a plurality of cavities which allow for filling of the space and therefore allow for a 3D cell culture. For example, a multiwell plate or a microarray or nanoarray comprising a plurality of defined cavities may be used. In the examples, a multiwell plate was successfully used. Preferably, the solid support does not substantially interfere with the viability of the cells and/or is suitable for culturing cells, for example the support may be a plastic support. For 3D cell culture, the solid support preferably contains at least one cavity, such as a well, more preferably a plurality of defined cavities. For example, multi-well plates may be used. Such multi-well plates comprise a plurality of defined cavities.

In a further embodiment, the present invention relates to a kit comprising the agents for performing the method steps i) to iiid) described above, preferably wherein the kit comprises:
a) primary fibroblast cells,
b) keratinocyte cells,
c) a support having a plurality of defined areas or cavities, wherein a subset of areas or cavities are (i) coated with adhesion enhancing agent, preferably gelatin, and/or (ii) are filled with fibroblast-derived matrix (FDM),
d) optionally a matrix promoting supplement, and
e) monocyte cells, and
f) optionally binding agents, preferably antibodies, which specifically recognize one or more M1 marker(s) and one or more M2 marker(s), and/or binding agents, preferably antibodies, which specifically recognize one or more M1 cell surface marker(s) and one or more M2 cell surface marker(s), and/or probes which specifically recognize one or more M1 marker mRNA(s) and one or more M2 marker mRNA(s).

Preferred M1 and M2 marker(s), cell surface marker(s) and/or marker mRNA(s) are described above for the methods of the present invention.

In a further embodiment, the present invention relates to a kit comprising the agents for performing the method steps i) to iiid) or i) to iiie) described above, wherein the kit comprises:
a) primary fibroblast cells,
b) keratinocyte cells,
c) a support having a plurality of defined areas or cavities, wherein a subset of areas or cavities are (i) coated with adhesion enhancing agent, preferably gelatin, and/or (ii) are filled with fibroblast-derived matrix (FDM),
d) optionally a matrix promoting supplement, and
e) optionally monocyte cells, and
f) binding agents, preferably antibodies, which specifically recognize one or more M1 cell surface marker(s) and one or more M2 cell surface marker(s), and, optionally:
binding agents, preferably antibodies, which specifically recognize one or more M1 marker(s) and one or more M2 marker(s), and/or probes which specifically recognize one or more M1 marker mRNA(s) and one or more M2 marker mRNA(s),
wherein the one ore more M1 cell surface markers are selected from CD38, CD64 and CD197, and wherein the one or more M2 cell surface markers are selected from CD200 receptor, CD206 and CD209, and wherein the one or more M1 markers are selected from CXCL10 and IL-23p19, and the one or more M2 markers are selected from CCL22 and CCL18, and wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18, and
g) optionally binding agents, preferably antibodies, which specifically recognize one or more one or more cytokine markers selected from IL-1alpha, IL-1beta and TNF-alpha.

In one preferred embodiment, the keratinocyte cells are selected from HaCaT cells and primary keratinocyte cells, in particular human primary keratinocyte cells.

In a more preferred embodiment, the keratinocyte cells used in the present invention are HaCaT cells.

Fibroblast-derived matrix (FDM) is obtainable by (i) seeding primary human dermal fibroblast cells on a support, which is pre-coated with an adhesion enhancing agent, such as gelatin, (ii) culturing the cells on the support, preferably until confluence is reached and (iii) contacting the cells with a matrix promoting supplement, such as Vitamin C or a physiologically acceptable salt thereof, or 2-phospho-L-ascorbic acid or a physiologically acceptable salt thereof, or a combination of EGF and insulin. FDM may be formed in situ or may be transferred to the support after formation.

Further, supports, such as chips are preferred, which allow for performing the methods of the invention. For example, a wound-on-a-chip may be provided, which allows for diagnosing, monitoring and predicting aspects of skin wound healing, such as identifying a non-healing skin wound and predicting worsened healing of a skin wound.

Therefore, in a yet further embodiment, the present invention relates to a support suitable for performing a method of the present invention, wherein the support comprises a plurality of defined areas or cavities and wherein:
a) a subset of areas or cavities are coated with an adhesion enhancing agent,
b) a subset of areas or cavities are coated with an adhesion enhancing agent and/or filled with fibroblast-derived matrix (FDM),
c) a subset of areas or cavities are untreated,
d) optionally:
   d1) a subset of areas or cavities contain binding agents, preferably antibodies, which specifically recognize one or more M1 marker(s), and
   d2) a subset of areas or cavities contain binding agents, preferably antibodies, which specifically recognize one or more one or more M2 marker(s),
e) optionally:
   e1) a subset of areas or cavities contain binding agents, preferably antibodies, which specifically recognize one or more M1 cell surface marker(s), and
   e2) a subset of areas or cavities contain binding agents, preferably antibodies, which specifically recognize one or more M2 cell surface marker(s),
and
f) optionally:
   f1) a subset of areas or cavities contain probes which specifically recognize one or more M1 marker mRNA(s), and
   f2) a subset of areas or cavities contain probes which specifically recognize one or more M2 marker mRNA(s),
wherein the subsets a) to f) are not overlapping,
preferably
(x) at least some of the areas or cavities pursuant to a) further contain primary fibroblast cells, and/or
(xi) at least some of the areas or cavities pursuant to (x) or b) further contain monocyte cells, and/or
(xii) at least some of the areas or cavities pursuant to c) further contain primary fibroblast cells, and/or
(xiii) at least some of the areas or cavities pursuant to c) further contain keratinocyte cells,
wherein the areas or cavities pursuant to (xii) and (xiii) are not overlapping,
more preferably wherein the support is a chip, array, such as a microarray or nanoarray, a plate, such a multiwell plate, or a dish, and/or the support is a plastic support.

Therefore, in a yet further embodiment, the present invention relates to a support suitable for performing a method of the present invention, wherein the support comprises a plurality of defined areas or cavities and wherein:
a) a subset of areas or cavities are coated with an adhesion enhancing agent,
b) a subset of areas or cavities are coated with an adhesion enhancing agent and/or filled with fibroblast-derived matrix (FDM),
c) a subset of areas or cavities are untreated,
d) optionally:
   d1) a subset of areas or cavities contain binding agents, preferably antibodies, which specifically recognize one or more M1 marker(s), and
   d2) a subset of areas or cavities contain binding agents, preferably antibodies, which specifically recognize one or more one or more M2 marker(s), wherein the one or more M1 markers are selected from CXCL10 and IL-23p19, and the one or more M2 markers are selected from CCL22 and CCL18,
e)
   e1) a subset of areas or cavities contain binding agents, preferably antibodies, which specifically recognize one or more M1 cell surface marker(s), and
   e2) a subset of areas or cavities contain binding agents, preferably antibodies, which specifically recognize one or more M2 cell surface marker(s), wherein the one or more M1 cell surface markers are selected from CD38, CD64 and CD197, and wherein the one or more M2 cell surface markers are selected from CD200 receptor, CD206 and CD209, f) optionally:
 f1) a subset of areas or cavities contain probes which specifically recognize one or more M1 marker mRNA(s), wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18, and
 f2) a subset of areas or cavities contain probes which specifically recognize one or more M2 marker mRNA(s), wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18, and g) optionally, a subset of areas or cavities contain binding agents, preferably antibodies, which specifically recognize one or more cytokine markers selected from IL-1alpha, IL-1 beta and TNF-alpha, wherein the subsets a) to 1) are not overlapping,
preferably
(x) at least some of the areas or cavities pursuant to a) further contain primary fibroblast cells, and/or
(xi) at least some of the areas or cavities pursuant to (x) or b) further contain monocyte cells, and/or
(xii) at least some of the areas or cavities pursuant to c) further contain primary fibroblast cells, and/or
(xiii) at least some of the areas or cavities pursuant to c) further contain keratinocyte cells,
wherein the areas or cavities pursuant to (xii) and (xiii) are not overlapping,
more preferably wherein the support is a chip, array, such as a microarray or nanoarray, a plate, such a multiwell plate, or a dish, and/or the support is a plastic support.

The solid support preferably contains a plurality of defined cavities. Cavities allow for filling of the space and therefore allow for a 3D cell culture. For example, a multiwell plate or a microarray or nanoarray comprising a plurality of defined cavities may be used. In the examples, a multiwell plate was successfully used. Preferably, the solid support does not substantially interfere with the viability of the cells and/or is suitable for culturing cells, for example the support may be a plastic support. For 3D cell culture, the solid support may contain a plurality of defined wells. For example, multi-well plates may be used. In one preferred embodiment, the support comprises 2, 3, 4, 5, 6, 7, 8, 9, 10 or more defined areas or cavities, such as 2, 3, 4, 5, 6, 7, 8, 9 or 10 to $10^5$, 2, 3, 4, 5, 6, 7, 8, 9 or 10 to $10^4$, 2, 3, 4, 5, 6, 7, 8, 9 or 10 to $10^3$, or 2, 3, 4, 5, 6, 7, 8, 9 or 10 to $10^2$ defined areas or cavities.

Traditional drug discovery is a long process. Even though recent advances in genomics and proteomics technologies have led to the identification of many new potential drug targets, preclinical hypothesis-based research still has a high attrition rate. In fact, 8 in 10 medicines fail in clinical trials [DiMasi J (2010), Clin Pharmacol Ther 87:272-277], and the probability of approval by regulatory authorities such as the American Food and Drug Administration (FDA) for drugs in clinical development phase I is as low as 10% [Hay M et al (2014) Nat Biotechnol 32:40-51]. The causes for failure are mostly lack of efficacy (56%) with safety issues (28%) in second place. [Arrowsmith J & Miller P (2013) Nat Rev Drug Discov 12:569].

Lack of efficacy suggests that pathway hypothesis-driven drug discovery has limited translatability into the clinic and thus significant failure rate. This is particularly true for diseases where the underlying pathomechanisms are poorly understood, as it is the case for chronic wounds [Eming S A et al (2014), Sci Transl Med 6:1-16)].

We aim at improving translatability and clinical success rate by using patient material as starting point for systems biology-driven, focused drug discovery. In our approach, we use diseased patient tissue or body fluids that contain key pathomechanistic drivers in newly developed in vitro, ex vivo test systems and search for compounds that will interfere with the pathophysiology.

Human material from healthy donors is currently mostly being used in drug safety and toxicity testing using a variety of organs including skin [Coleman R A (2011) Int Scholarly Res Network article ID 806789; Clotworthy M & Archibald K (2013) Expert Opin Drug Metab Toxicol 9:1155-1169; Atac B (2013) Lab Chip 13:3555-3561]. Translational drug discovery using human tissue is in its infancy [Clotworthy M (2012) Expert Opin Drug Discov 7:543-547], and only in oncology, diseased tissue is being used in significant amounts [Nieva J J (2012) Future Oncol 8:989-998]. With human material containing the relevant pathogenic factors at the beginning of compound screening, we believe we can improve translatability, clinical success rate and substantially shorten the preclinical development time.

Wound exudates from chronic wounds are pro-inflammatory in vitro and delay wound healing in in vivo assays. Thus, we conclude that key factors responsible for delayed healing are contained in these exudates as well as in wound biofilms.

Figure 2:
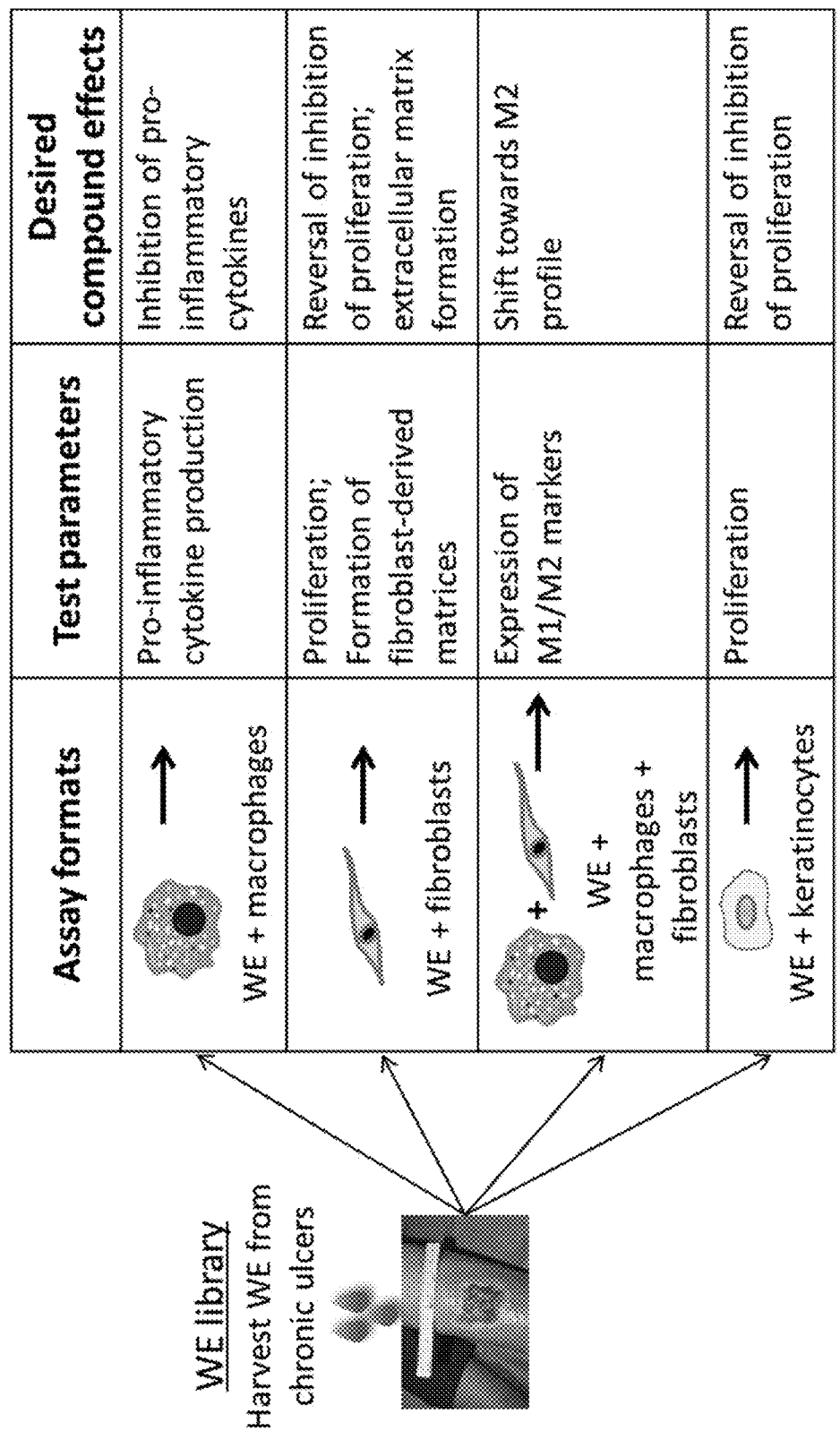

Macrophages, keratinocytes and fibroblasts are perceived as pivotal cells in sustained wound inflammation and resulting wound chronicity. Using WE from chronic wounds as stimulus, we established new test systems in these cell types that are suitable for compound screening. They form the basis for our investigations aimed at the identification of inhibitors of WE-induced cell activation for therapy of non-healing chronic ulcers (FIG. 2).

Surprisingly, we could establish a reliable, robust and effective method for screening for compounds suitable for modulating skin wound healing. The method steps are outlined in Example 4.3 and the method makes use of the assay steps described above for the further methods of the invention. In particular, the proliferation of primary fibroblast cells in the presence of (i) a wound exudate sample or wound biofilm sample obtained from a skin wound of at least one individual, and (ii) at least one candidate compound is measured as primary assay. In case it is found that the candidate compound is found to be active in the assay, at least one of the further assays described herein are performed. The candidate compound is found to be active in the proliferation of primary fibroblast cells assay in case the value obtained in the assay is at least 10% above or at least 10% below a control value established in the absence of the at least one candidate compound, or is above a cut-off value.

Therefore, in a yet further embodiment, the present invention relates to a method for screening for compounds suitable for modulating skin wound healing, comprising the following steps:
A) measuring the proliferation of primary fibroblast cells in the presence of (i) a wound exudate sample or wound biofilm sample obtained from a skin wound of at least one individual, and (ii) at least one candidate compound, and B) performing one, two, three, four or five of the following method steps B1) to B5) in case the value obtained in A) is at least 10% above or at least 10% below a control value established in the absence of the at least one candidate compound:
- B1) measuring the fibroblast-derived matrix formation by primary fibroblast cells in the presence of (i) a wound exudate sample or wound biofilm sample obtained from a skin wound of at least one individual and (ii) said at least one candidate compound,
- B2) measuring the proliferation of keratinocyte cells in the presence of (i) a wound exudate sample or wound biofilm sample obtained from a skin wound of at least one individual and (ii) said at least one candidate compound,
- B3) measuring the amount(s) of one or more M1 marker(s) and one or more M2 marker(s) in the supernatant of macrophages incubated with (i) a wound exudate sample or wound biofilm sample obtained from a skin wound of at least one individual and (ii) said at least one candidate compound, wherein the macrophages are in co-culture with fibroblasts,
- B4) measuring the amount(s) and/or frequency distribution(s) of one or more M1 cell surface marker(s) and one or more M2 cell surface marker(s) on macrophages incubated with (i) a wound exudate sample or wound biofilm sample obtained from a skin wound of at least one individual and (ii) said at least one candidate compound, wherein the macrophages are in co-culture with fibroblasts,
- B5) measuring the expression level(s) of one or more M1 marker mRNA(s) and one or more M2 marker mRNA(s) in macrophages incubated with (i) a wound exudate sample or wound biofilm sample obtained from a skin wound of at least one individual and (ii) said at least one candidate compound, wherein the macrophages are in co-culture with fibroblasts, wherein the compound is identified as being suitable for modulating skin wound healing, in case at least one value obtained in B1) to B5) is at least 10% above or at least 10% below a control value established in the absence of the candidate compound, preferably wherein the method steps pursuant to A) and B1) to 65) are performed as described above for the methods of the invention.

Therefore, in a yet further embodiment, the present invention relates to a method for screening for compounds suitable for modulating skin wound healing, comprising the following steps:

A) measuring the proliferation of primary fibroblast cells in the presence of (i) a wound exudate sample or wound biofilm sample obtained from a skin wound of at least one individual, and (ii) at least one candidate compound, and B) performing one, two, three, four or five of the following method steps B1) to B5) or one, two, three, four, five or six of the following method steps B1) to B6) in case the value obtained in A) is at least 10% above or at least 10% below a control value established in the absence of the at least one candidate compound:
- B1) measuring the fibroblast-derived matrix formation by primary fibroblast cells in the presence of (i) a wound exudate sample or wound biofilm sample obtained from a skin wound of at least one individual and (ii) said at least one candidate compound,
- B2) measuring the proliferation of keratinocyte cells in the presence of (i) a wound exudate sample or wound biofilm sample obtained from a skin wound of at least one individual and (ii) said at least one candidate compound,
- B3) measuring the amount(s) of one or more M1 marker(s) and one or more M2 marker(s) in the supernatant of macrophages incubated with (i) a wound exudate sample or wound biofilm sample obtained from a skin wound of at least one individual and (ii) said at least one candidate compound, wherein the macrophages are in co-culture with fibroblasts, wherein the one or more M1 markers are selected from CXCL10 and IL-23p19, and the one or more M2 markers are selected from CCL22 and CCL18,
- B4) measuring the amount(s) and/or frequency distribution(s) of one or more M1 cell surface marker(s) and one or more M2 cell surface marker(s) on macrophages incubated with (i) a wound exudate sample or wound biofilm sample obtained from a skin wound of at least one individual and (ii) said at least one candidate compound, wherein the macrophages are in co-culture with fibroblasts, wherein the one or more M1 cell surface markers are selected from CD38, CD64 and CD197, and wherein the one or more M2 cell surface markers are selected from CD200 receptor, CD206 and CD209,
- B5) measuring the expression level(s) of one or more M1 marker mRNA(s) and one or more M2 marker mRNA(s) in macrophages incubated with (i) a wound exudate sample or wound biofilm sample obtained from a skin wound of at least one individual and (ii) said at least one candidate compound, wherein the macrophages are in co-culture with fibroblasts, wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18,
- B6) measuring the amount(s) of one or more cytokine markers in the supernatant of macrophages incubated with (i) a wound exudate sample or wound biofilm sample obtained from a skin wound of at least one individual and (ii) said at least one candidate compound, wherein the macrophages are in co-culture with fibroblasts, and wherein the one or more cytokine markers are selected from IL-1 alpha, IL-1 beta and TNF-alpha, wherein the compound is identified as being suitable for modulating skin wound healing, in case at least one value obtained in B1) to B5) or B1) to B6) is at least 10% above or at least 10% below a control value established in the absence of the candidate compound, preferably wherein the method steps pursuant to A) and B1) to B5) or A) and B1) to B6) are performed as described above for the methods of the invention.

In a preferred embodiment, step B) relates to performing one, two, three, four or five of the above method steps B1) to B4) and B6) in case the value obtained in A) is at least 10% above or at least 10% below a control value established in the absence of the at least one candidate compound. In such preferred embodiment, the compound is identified as being suitable for modulating skin wound healing, in case at least one value obtained in B1) to 64) and B6) is at least 10% above or at least 10% below a control value established in the absence of the candidate compound, preferably wherein the method steps pursuant to A) and B1) to B4) and B6) are performed as described above for the methods of the invention.

In one preferred embodiment of the present invention, the sample is a wound exudate sample. In another preferred embodiment, the sample is a wound biofilm sample. In a more preferred embodiment, the sample is a wound exudate sample.

The methods may be repeated one or more times.

In one preferred embodiment, step B) includes performing one, two, three, four or five of said method steps B1) to B5) or one, two, three, four, five or six of said method steps B1) to B6), or one, two, three, four or five of the above method steps B1) to B4) and 66) in case the value obtained in A) is above or below a cut-off value. For example, the cut-off value may be the control value established in the absence of the candidate compound+X*standard deviation, wherein X is 0.5 or more, such as 1, 1.5, 2, 2.5 3, 4 or more, such as up to 5, 6, 7, 8, 9 or 10. In the examples, X is 3. Alternatively, the cut-off value may be the control value established in the absence of the candidate compound–X*standard deviation, wherein X is 0.5 or more, such as 1, 1.5, 2, 2.5 3, 4 or more, such as up to 5, 6, 7, 8, 9 or 10.

In a further preferred embodiment, the compound is identified as being suitable for modulating skin wound healing, in case at least one value obtained in B1) to B5) or B1) to B6) or B1) to B4) and B6) is at least 10% above or 10% below a respective cut-off value.

In one preferred embodiment, the wound exudate sample is diluted, in particular as described above. In another preferred embodiment, the wound biofilm sample is diluted, in particular as described above.

Accordingly, the preferred embodiments for the further methods of the invention, in particular regarding the assays of the invention, also apply to the above method for screening.

In one preferred embodiment, one, two, three, four or five of the method steps B1) to B5) or one, two, three, four, five or six of said method steps B1) to B6) or one, two, three, four or five of the above method steps B1) to B4) and B6) are performed in case the value obtained in A) above is at least 15%, 20%, 25%, 30%, 40% or 50% above a control value established in the absence of the at least one candidate compound.

In a more preferred embodiment, the compound is identified as being suitable for modulating skin wound healing, in case at least one value obtained in B1) and B2) is at least 10%, 15%, 20%, 25%, 30%, 40% or 50% above a control value established in the absence of the at least one candidate compound.

In a more preferred embodiment, modulating wound healing is improving wound healing.

In another preferred embodiment, one, two, three, four or five of the method steps B1) to B5) or one, two, three, four, five or six of said method steps B1) to B6) or one, two, three, four or five of the above method steps B1) to B4) and B6) are performed in case the value obtained in A) above is at least 15%, 20%, 25%, 30%, 40% or 50% below a control value established in the absence of the at least one candidate compound.

In a more preferred embodiment, the compound is identified as being suitable for modulating skin wound healing, in case at least one value obtained in B1) and B2) is at least 10%, 15%, 20%, 25%, 30%, 40% or 50% below a control value established in the absence of the at least one candidate compound.

In another embodiment, modulating wound healing is worsening wound healing. Compounds identified as being suitable for worsening skin wound healing are suitable for treating and/or preventing hypertrophic scars, keloids or fibrosis.

The (i) wound exudate sample or wound biofilm sample obtained from a skin wound of at least one individual, and (ii) the at least one candidate compound may be added for incubation simultaneously, or sequentially. In case of adding simultaneously, (i) and (ii) may be added as separate compositions, or as a single composition. For example, the optionally diluted wound exudate sample or wound biofilm sample may be added to an assay, e.g. by pipetting the liquid into a well of a support, and the candidate compound is added separately, e.g. by pipetting the liquid containing such compound into a well of a support, either before, simultaneous with, or after the optionally diluted wound exudate sample or wound biofilm sample. Alternatively, the optionally diluted wound exudate sample or wound biofilm sample may be mixed with the at least one candidate compound or composition comprising at least one candidate compound, and be added to the assay subsequently.

The method steps include contacting of a wound exudate sample or wound biofilm sample obtained from a skin wound of at least one individual. For example, a wound exudate sample or wound biofilm sample obtained from a skin wound of one individual may be used, or mixtures of wound exudate samples obtained from a skin wound of two or more individuals, such as 2, 3, 4, 5, 6, 7, 8, 9, 10 or more individuals may be used. The wound exudate samples or wound biofilm samples may be samples from healing wounds or non-healing wounds, such as ulcers, or mixtures thereof. In one preferred embodiment of the present invention, the sample is a wound exudate sample. In another preferred embodiment, the sample is a wound biofilm sample. In a more preferred embodiment, the sample is a wound exudate sample.

In one preferred embodiment, measuring the proliferation of primary fibroblast cells in the presence of (i) a wound exudate sample or wound biofilm sample obtained from a skin wound of at least one individual, and (ii) at least one candidate compound includes the following steps:
(i) culturing primary human dermal fibroblast cells,
(ii) incubating the cells on a solid support, thereby allowing the cells to adhere to the support,
(iii) contacting the cells with (i) wound exudate sample or wound biofilm sample obtained from a skin wound of at least one individual, which is optionally diluted, and (ii) at least one candidate compound, wherein the contacting may be performed before or after adherence of the cells occurs, and wherein (i) and (ii) may be contacted simultaneously or sequentially,
(iv) determining the amount, preferably the cell number, including the formation of extracellular matrix, of the primary fibroblast cells, such as by fixing cells and determining total protein content,
preferably wherein the method is performed in 2D cell culture.

In one preferred embodiment, measuring the fibroblast-derived matrix formation by primary fibroblast cells in the presence of (i) a wound exudate sample or wound biofilm sample obtained from a skin wound of at least one individual and (ii) said at least one candidate compound includes the following steps:
(i) seeding primary human dermal fibroblast cells on a support, which is preferably pre-coated with an adhesion enhancing agent, such as gelatin, (ii) culturing the cells on the support, preferably until confluence is reached,
(iii) contacting the cells with (i) a matrix promoting supplement, (ii) wound exudate sample or wound biofilm sample obtained from a skin wound of at least one individual, which is optionally diluted, and (iii) at least one candidate compound, wherein the contacting may be performed before or after adherence of the cells occurs, and wherein (i), (ii) and (iii) may be contacted simultaneously or sequentially,
(iv) determining the amount of the fibroblast-derived matrix, such as by fixing cells and determining total protein content,
preferably wherein the method is performed in 3D cell culture.

In another preferred embodiment, measuring the proliferation of keratinocyte cells in the presence of (i) a wound exudate sample or wound biofilm sample obtained from a skin wound of at least one individual and (ii) said at least one candidate compound includes the following steps:
(i) culturing keratinocyte cells,
(ii) incubating the cells on a solid support, thereby allowing the cells to adhere to the support,
(iii) contacting the cells with (i) wound exudate sample or wound biofilm sample obtained from a skin wound of at least one individual, which is optionally diluted, and (ii) at least one candidate compound, wherein the contacting may be performed before or after adherence of the cells occurs, and wherein (i) and (ii) may be contacted simultaneously or sequentially,
(iv) determining the amount, preferably the cell number, of the keratinocyte cells, such as by fixing cells and determining total protein content,
preferably wherein the method is performed in 2D cell culture.

In another preferred embodiment, measuring the amount(s) of one or more M1 marker(s) and one or more M2 marker(s) in the supernatant of macrophages incubated with (i) a wound exudate sample or wound biofilm sample obtained from a skin wound of at least one individual and (ii) said at least one candidate compound, wherein the macrophages are in co-culture with fibroblasts, includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with i) wound exudate sample or wound biofilm sample obtained from a skin wound of at least one individual, which is optionally diluted, and (ii) at least one candidate compound, wherein (i) and (ii) may be contacted simultaneously or sequentially,
(iv) determining the amount of one or more M1 markers and one or more M2 markers in the cell culture supernatant,
preferably wherein the one or more M1 markers are selected from CXCL10 and IL-23p19, and/or the one or more M2 markers are selected from CCL22 and CCL18, more preferably wherein the markers are determined by using an immunological assay, even more preferably by using an ELISA assay.

In another preferred embodiment, measuring the amount(s) and/or frequency distribution(s) of one or more M1 cell surface marker(s) and one or more M2 cell surface marker(s) on macrophages incubated with (i) a wound exudate sample or wound biofilm sample obtained from a skin wound of at least one individual and (ii) said at least one candidate compound, wherein the macrophages are in co-culture with fibroblasts, includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with i) wound exudate sample or wound biofilm sample obtained from a skin wound of at least one individual, which is optionally diluted, and (ii) at least one candidate compound, wherein (i) and (ii) may be contacted simultaneously or sequentially,
(iv) determining the amount(s) and/or frequency distribution(s) of one or more M1 marker(s) and one or more M2 marker(s) on the cell surface of macrophages,
preferably wherein the one or more M1 cell surface markers are selected from CD38, CD64 and CD197, and/or the one or more M2 cell surface markers are selected from CD200 receptor (CD200R), CD206 and CD209, more preferably wherein the amount(s) and/or frequency distribution(s) of the cell surface markers are determined by an immunological assay and/or a fluorescence assay, in particular by FACS analysis, even more preferably wherein step iv) includes:
contacting the macrophages with binding agents, preferably antibodies, which specifically recognize one or more M1 cell surface marker(s) and one or more M2 cell surface marker(s), wherein the binding agents are optionally labelled, in particular labelled with a fluorescent label, and determining the amounts of binding molecules bound to the macrophages, in particular by determining mean fluorescence intensity, thereby determining the amount(s) of the cell surface markers,
and/or
contacting the macrophages with binding agents, preferably antibodies, which specifically recognize one or more M1 cell surface marker(s) and one or more M2 cell surface marker(s), wherein the binding agents are optionally labelled, in particular labelled with a fluorescent label, and determining the percentages of cells which are positive for the one or more M1 cell surface marker(s) and the one or more M2 cell surface marker(s), respectively, within a cell population, in particular wherein FACS analysis is performed, thereby determining the frequency distribution(s) of the cell surface markers.

In another preferred embodiment, measuring the expression level(s) of one or more M1 marker mRNA(s) and one or more M2 marker mRNA(s) in macrophages incubated with (i) a wound exudate sample or wound biofilm sample obtained from a skin wound of at least one individual and (ii) said at least one candidate compound, wherein the macrophages are in co-culture with fibroblasts, includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with i) wound exudate sample or wound biofilm sample obtained from a skin wound of at least one individual, which is optionally diluted, and (ii) at least one candidate compound, wherein (i) and (ii) may be contacted simultaneously or sequentially, (iv) determining the expression level(s) of one or more M1 marker mRNA(s) and one or more M2 marker mRNA(s) in the macrophages, preferably wherein the one or more M1 marker mRNA(s) are selected from CD38, CD64, CD197, CXCL10 and IL-23p19, and/or the one or more M2 marker mRNA(s) are selected from CD200 receptor (CD200R), CD206, CD209, CCL22 and CCL18, more preferably wherein the method comprises contacting a probe which specifically binds to a marker mRNA, wherein the probe is optionally labelled, with the macrophage RNA under conditions which are conducive to hybridization, and detecting the hybridized probe.

In another preferred embodiment, measuring the amount(s) of one or more cytokine markers selected from IL1alpha, IL1beta and TNFalpha in the supernatant of macrophages incubated with (i) a wound exudate sample or wound biofilm sample obtained from a skin wound of at least one individual and (ii) said at least one candidate compound, wherein the macrophages are in co-culture with fibroblasts, includes the following steps:

(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with i) wound exudate sample or wound biofilm sample obtained from a skin wound of at least one individual, which is optionally diluted, and (ii) at least one candidate compound, wherein (i) and (ii) may be contacted simultaneously or sequentially,
(iv) determining the amount of one or more of the cytokines IL1alpha, IL1beta and TNFalpha in the cell culture supernatant, preferably wherein the cytokine markers are determined by using an immunological assay, more preferably by using an ELISA assay.

It is possible that a wide variety of compounds may be used in the methods for screening. For example, a small molecule, a hormone, sugar, protein, peptide, polymer, biological, such as a protein, a peptide, an antibody or derivative thereof, or a conjugate thereof, a nucleic acid, such a viral agent, a wound dressing which optionally comprises a therapeutically active agent, or one or more cell(s), such as one or more genetically modified cell may be used. Further, a plurality of compounds may be tested in parallel. In case 2, 3, 4, 5, 6, 7, 8, 9, 10 or more candidate compounds are to be tested in parallel, such compounds may be added separately or as at least one composition comprising two or more candidate compounds. Thereby, a huge number of candidate compounds may be tested. For example, 2 or more compositions, such as 1, 2, 3, 4, 5, 6, 7, 8, 9, 10 or more compositions, each comprising at least one, such as 1, 2, 3, 4, 5, 6, 7, 8, 9, 10 or more candidate compounds, may be added. The compounds or composition comprising compounds may be provided as a liquid, such as a solution, in particular aqueous solution or medium or suspension, such as a suspension in an aqueous solution or medium. The liquid, in particular solution or suspension, without candidate compound(s) preferably does not substantially interfere with the viability of cells used in the assay(s).

Therefore, in one preferred embodiment of the method of the invention, the at least one compound is selected from a small molecule, a hormone, sugar, protein, peptide, polymer, biological, such as a protein, a peptide, an antibody or derivative thereof, or a conjugate thereof, a nucleic acid, such a viral agent, or one or more cell(s), such as one or more genetically modified cell. In another preferred embodiment of the method of the invention, the at least one compound is selected from an immunomodulatory agent, more preferably an immunosuppressive agent, an antibiotic, an antiinfective, a growth factor, a cytokine, an antiproliferative agent and an agent stimulating proliferation. For example, known approved active agents may be tested, such as active agents approved in the field of wound healing or for other indications, such as for inflammatory and/or proliferative disorders. Further, novel compounds and/or compound libraries may be tested. For example, combinatorial libraries or other small molecule compound libraries, or antibody libraries may be tested.

In another preferred embodiment of the method of the invention, the at least one compound is a single compound, or 2, 3, 4, 5, or more different compounds, wherein the 2, 3, 4, 5, or more different compounds may be present in a single composition or in 2 or more separate compositions.

In another preferred embodiment of the method of the invention, the values are measured at least in triplicate and/or a statistical significance is established in B), more preferably, wherein $p \leq 0.05$, $p \leq 0.001$ or $p \leq 0.001$, and/or the compound is identified as being suitable for modulating skin wound healing, in case at least one value obtained in B1) to B5) or B1) to B6) or B1) to B4) and B6) is at least 10% above, such as at least 10%, 15%, 20%, 25%, 30%, 40% or 50% above, or at least 10% below, such as at least 10%, 15%, 20%, 25%, 30%, 40% or 50% below a control value established in the absence of the candidate compound with statistical significance, more preferably, wherein $p \leq 0.05$, $p \leq 0.001$ or $p \leq 0.001$.

A compound that is identified to be suitable for modulating, in particular improving skin wound healing can be tested in in vitro, ex vivo and/or in vivo models for efficacy and safety in the context of wound healing.

A compound that is identified to be suitable for modulating, in particular worsening skin wound healing can be tested in in vitro, ex vivo and/or in vivo models for efficacy and safety in the context of hypertrophic scars, keloids and fibrosis.

A keloid is a type of scar of the skin which, depending on its maturity, is composed mainly of either type III or type I collagen. It is a result of an overgrowth of granulation tissue at the site of a healed skin injury which is then slowly replaced by collagen type 1. A keloid scar is benign.

Fibrosis is the formation of excess fibrous connective tissue in an organ or tissue in a reparative or reactive process.

FIGURE LEGEND

FIG. 1: Cell recruitment to skin wounds: normal healing process

FIG. 2: Schematic representation of in vitro assays. Wound exudates from chronic ulcers are collected, diluted into cell culture medium and used to stimulate cells in microtiter plates. Macrophages are generated by in vitro differentiation of monocytes, which are isolated from human blood. Upon stimulation with chronic WE, they produce pro-inflammatory cytokines. Primary human fibroblasts are either grown in monolayer culture or into fibroblast-derived matrices ("artificial skin")—in the absence or presence of WE. Chronic WE can inhibit cell and/or matrix growth. Macrophages are grown in the presence of fibroblasts or fibroblast-derived matrices in the absence or presence of WE. Chronic WE leads to a shift towards the M1 macrophage phenotype. Keratinocytes are grown in monolayer culture in the absence or presence of WE. Chronic WE can inhibit cell growth. We screened for compounds, which counteract the pro-inflammatory and growth inhibitory effects of WE or produce a shift towards an M2 macrophage profile.

Figure 3:
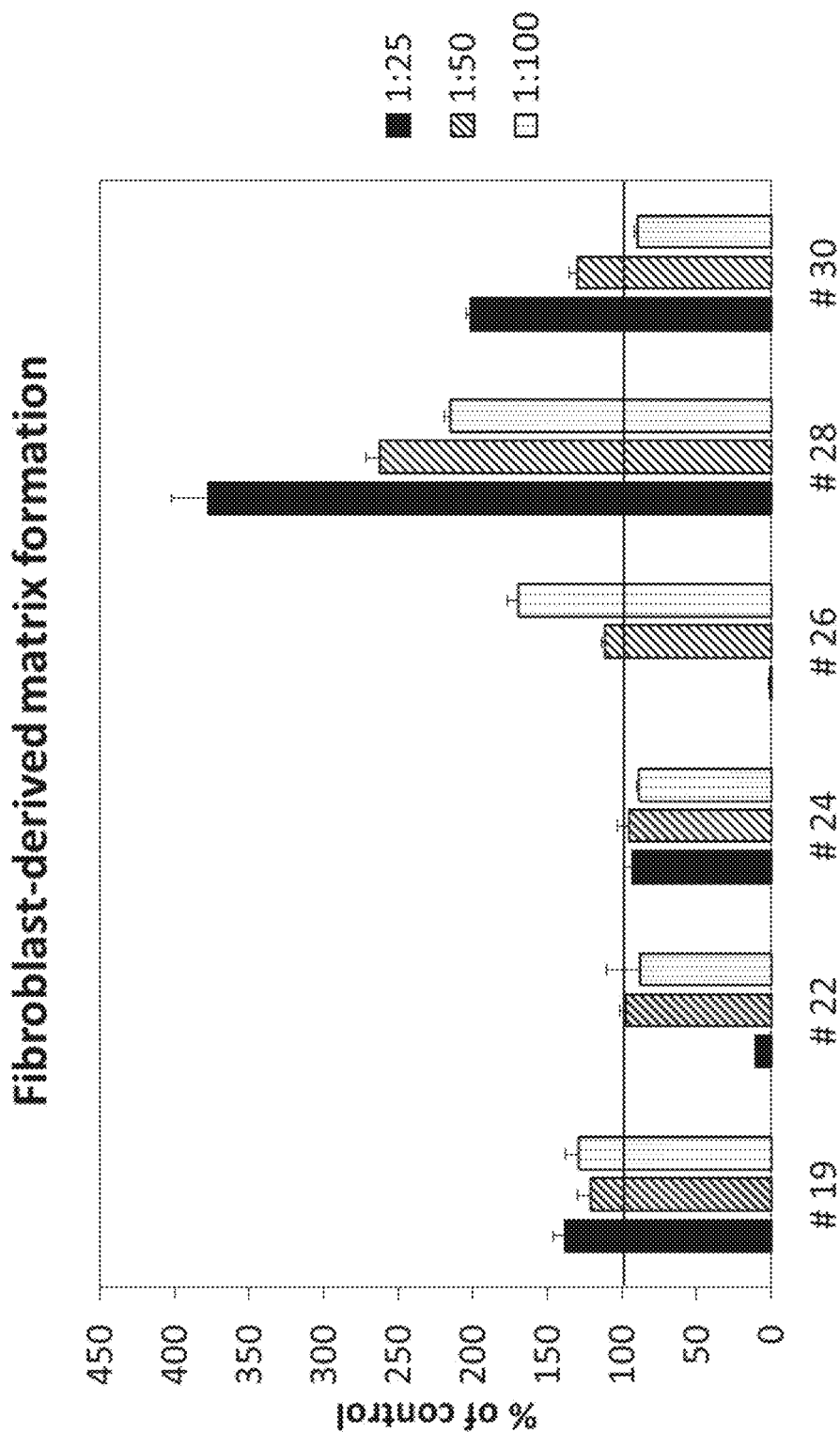

FIG. 3: Effect of different WE on Fibroblast-derived Matrix (FDM) formation. FDM were grown in 96-well plates in the absence (control) or presence of different WEs. Total cellular protein was measured to reflect growth and extracellular matrix production.

Figure 4:
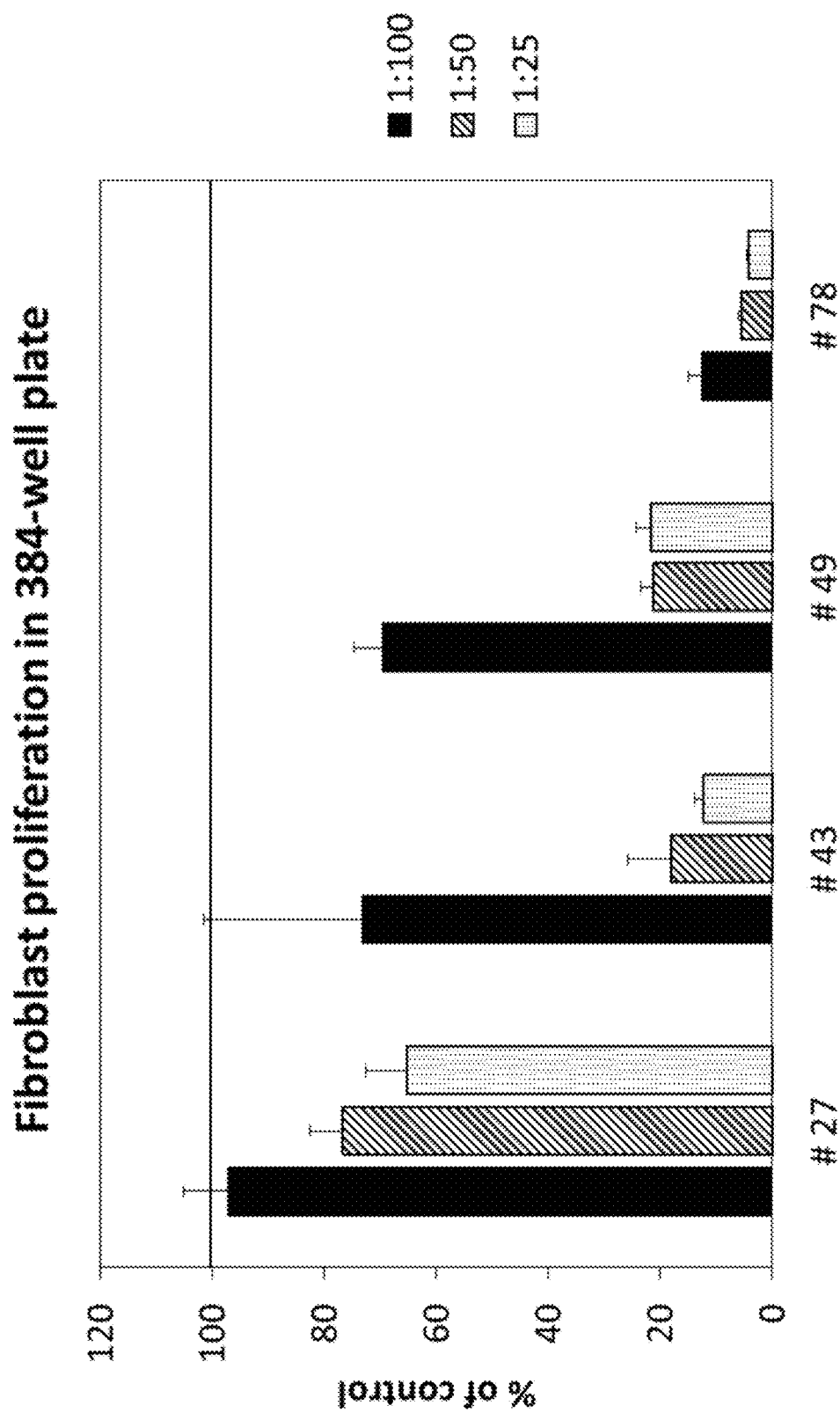

FIG. 4: Growth characteristics of primary human fibroblasts in the presence of four WE. WE were diluted 1:25, 1:50 or 1:100 in medium, and proliferation was compared to untreated controls (=100%). Values are average±SD of 8 samples.

Figure 5:
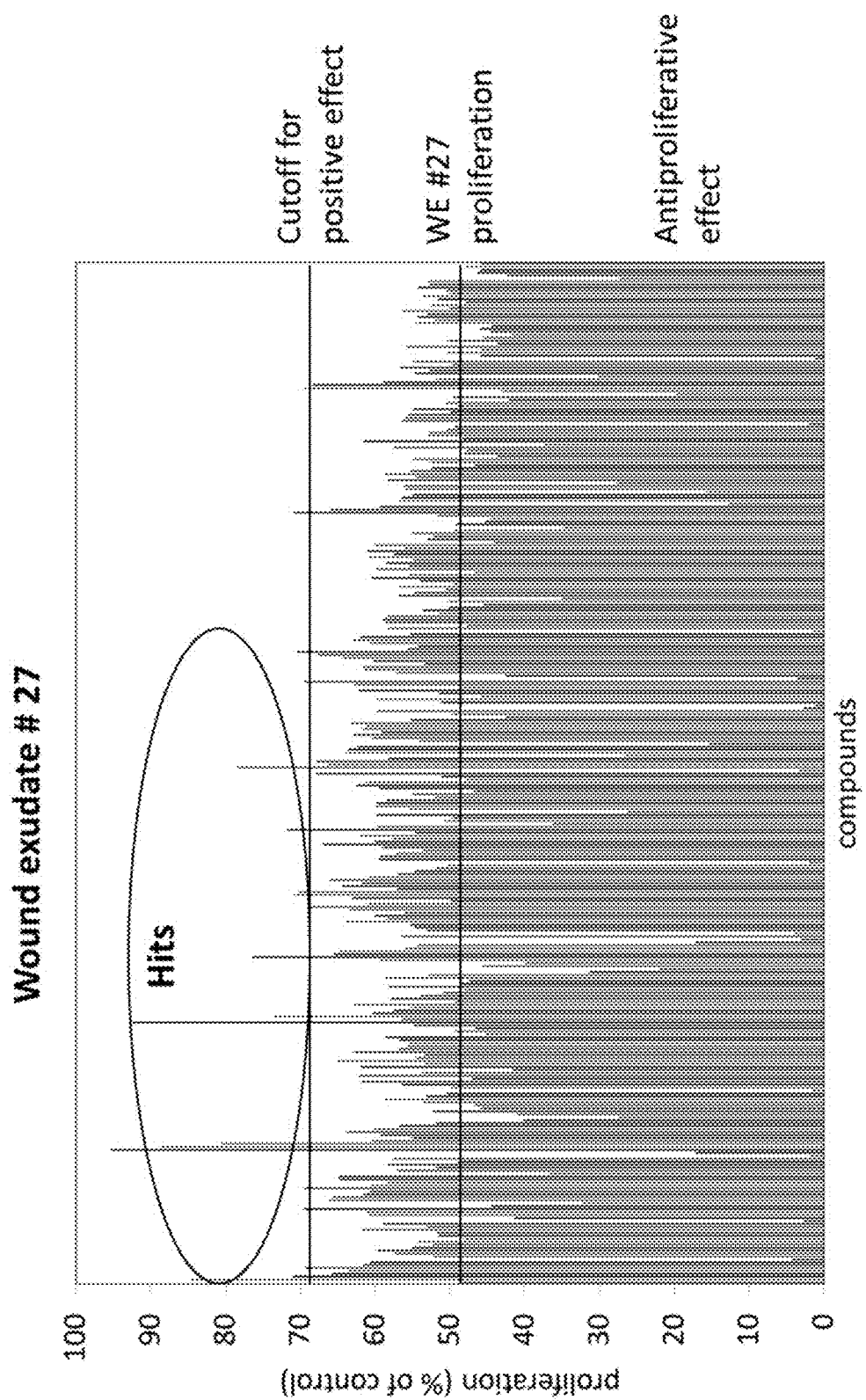

FIG. 5: Proliferation results of primary screen in one exemplary 384-well plate. Lines represent individual compounds. Lines below the cut-off line for proliferation inhibition by WE #27 (48.8% horizontal line "WE #27 proliferation") are antiproliferative compounds. Values above the upper horizontal line were considered positive hits.

FIG. 6: Biochemical and cellular (macrophage) characterization of the screening exudates. A) Enzyme activities of Myeloperoxidase (MPO), neutrophil elastase and metalloproteinases (MMP); B) Levels of inflammatory cytokines IL-1α, IL-1β and TNF-α in the WE, and C) levels of IL-1α, IL-1β and TNF-α induced in the supernatants of macrophages which had been stimulated with WE for 24 hours.

FIG. 7: Patient wound exudate material

FIG. 8: Biochemical characterization of the exudates. Enzyme activities of Myeloperoxidase (MPO), neutrophil elastase and metalloproteinases (MMP).

FIG. 9: Enzyme activities: WE from non-healing wounds. Approximately half of the non-healing wounds show signs of neutrophil influx (MPO, elastase), possibly due to infection. Metalloproteinase activities are generally low with some exceptions. MPO (front line columns): Highest value: $2.2 \times 10^6$ mU/ml. Elastase (middle line columns): Highest value: $5 \times 10^4$ nM. MMP (back line columns): Highest value: $1.8 \times 10^6$ nM.

FIG. 10: Enzyme activities: WE from healing wounds. MPO front line columns. Elastase middle line columns. MMP back line columns. All enzyme levels are generally lower than for the non-healing wounds.

FIG. 11: Cytokines in WE from healing versus non-healing wounds.

Figure 12:
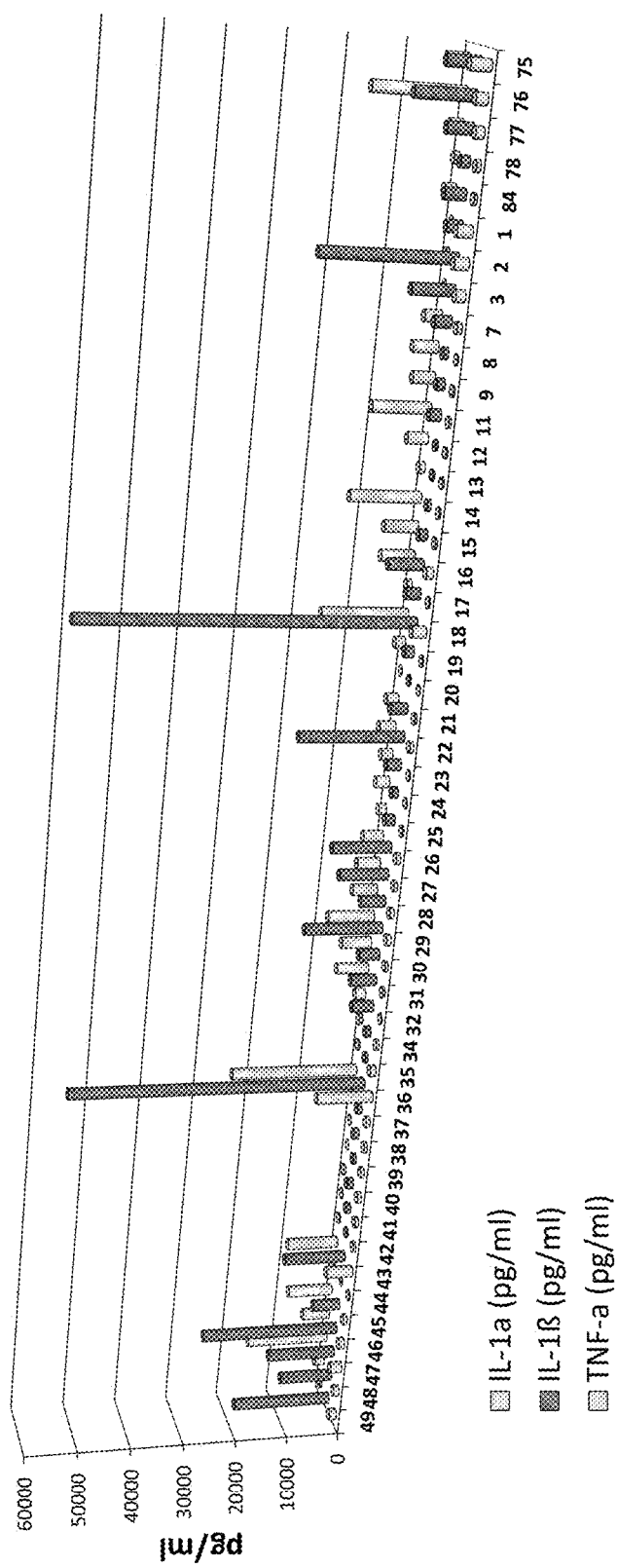

FIG. 12: Cytokines in WE from non-healing wounds. More than half of the non-healing WE contain appreciable levels of IL-1β. IL-1α is measurable in the same WE as IL-1β, but the levels are much lower. TNF-α is present in more than half of the non-healing WE.

Figure 13:
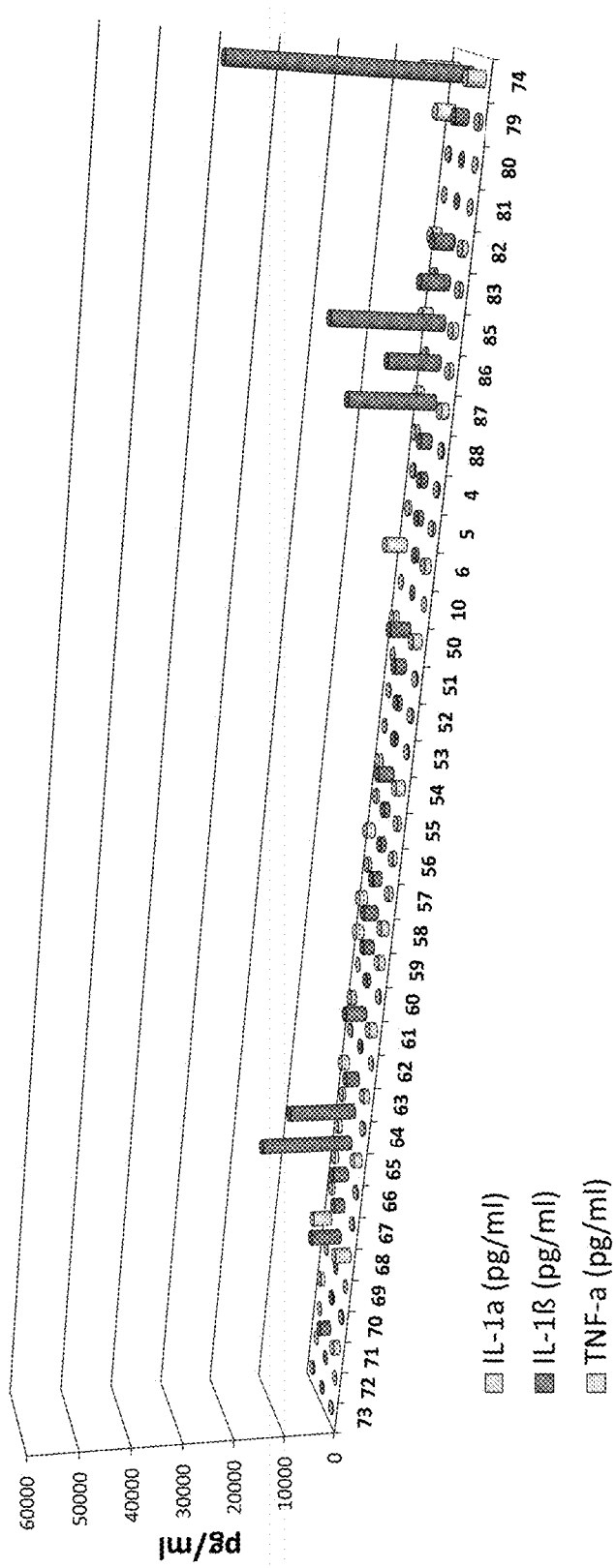

FIG. 13: Cytokines in WE from healing wounds. In some of the healing WE, cytokine levels are in the same range as in non-healing WE.

Figure 14:
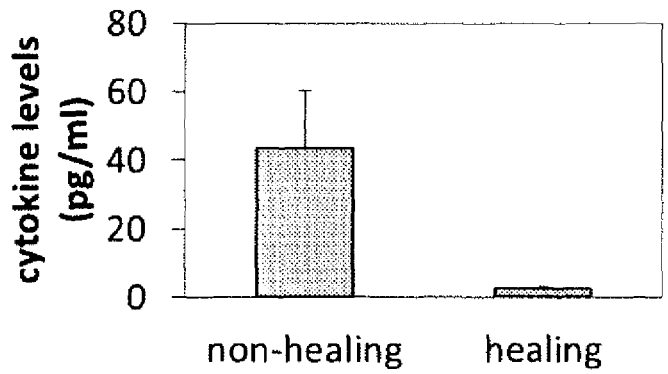
Figure 14:
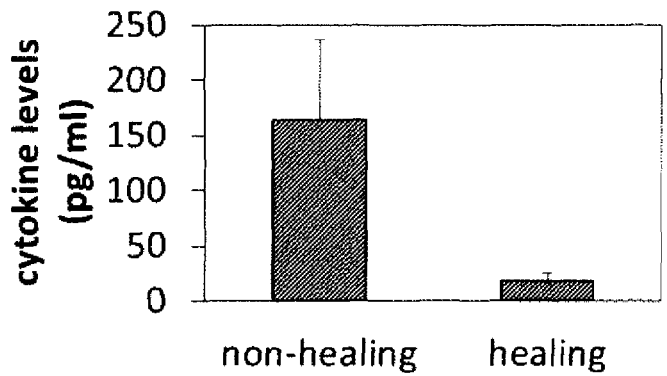
Figure 14:
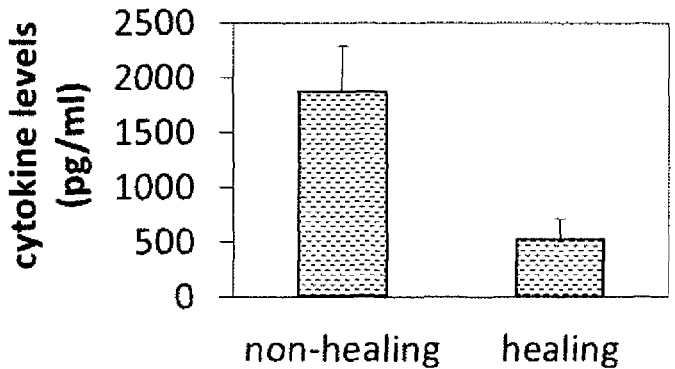

FIG. 14: Cytokines in macrophage supernatants.

FIG. 15: Cytokines in macrophage supernatants. Macrophage IL-1α front line columns. Macrophage IL-1β middle line columns. TNF-α back line columns. Only about 50% of the WE from non-healing wounds induce cytokine secretion by macrophages. The main cytokine induced by WE from non-healing wounds is TNF-α.

Figure 16:
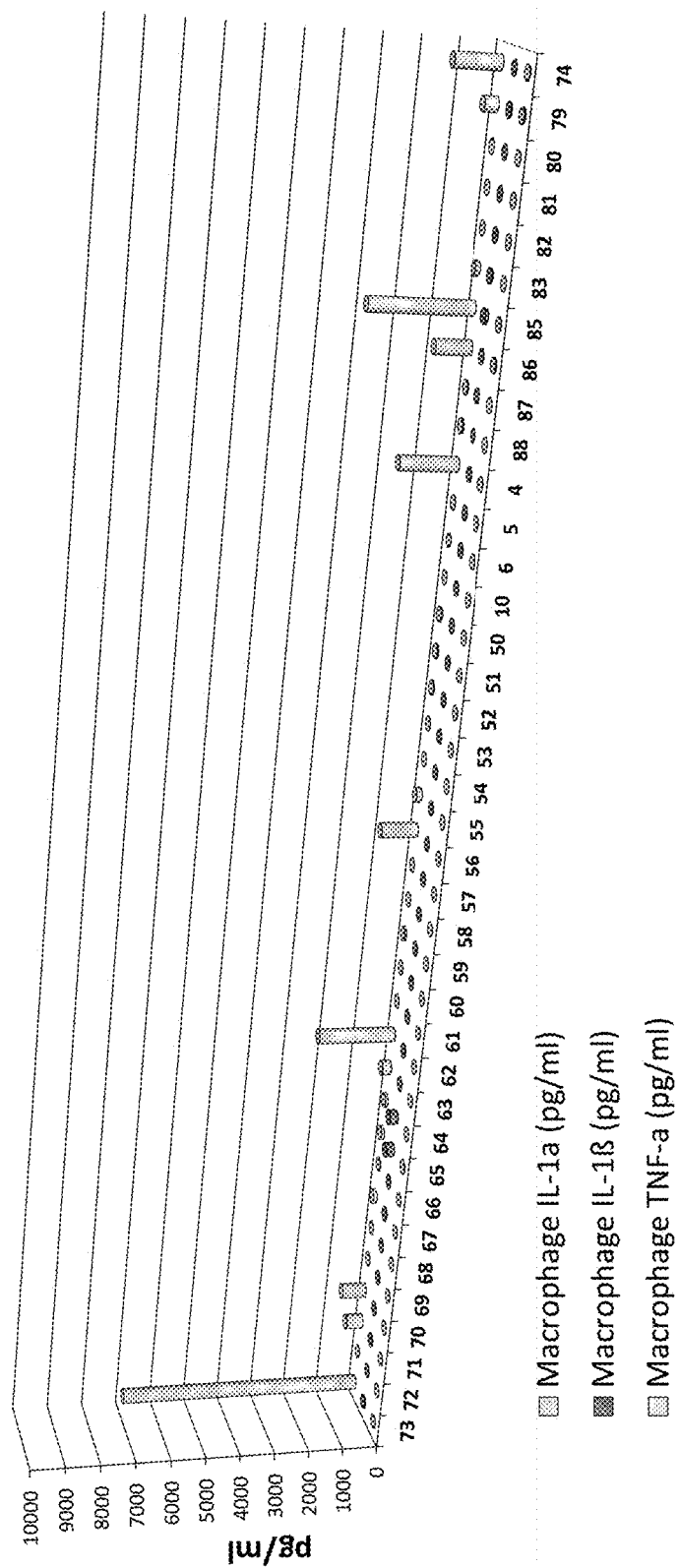

FIG. 16: Cytokines in macrophage supernatants. Macrophage IL-1α front line columns. Macrophage IL-1β middle line columns. TNF-α back line columns. WE from healing wounds induce fewer cytokines. There was no correlation between cytokine levels in WE and macrophage supernatants.

Figure 17:
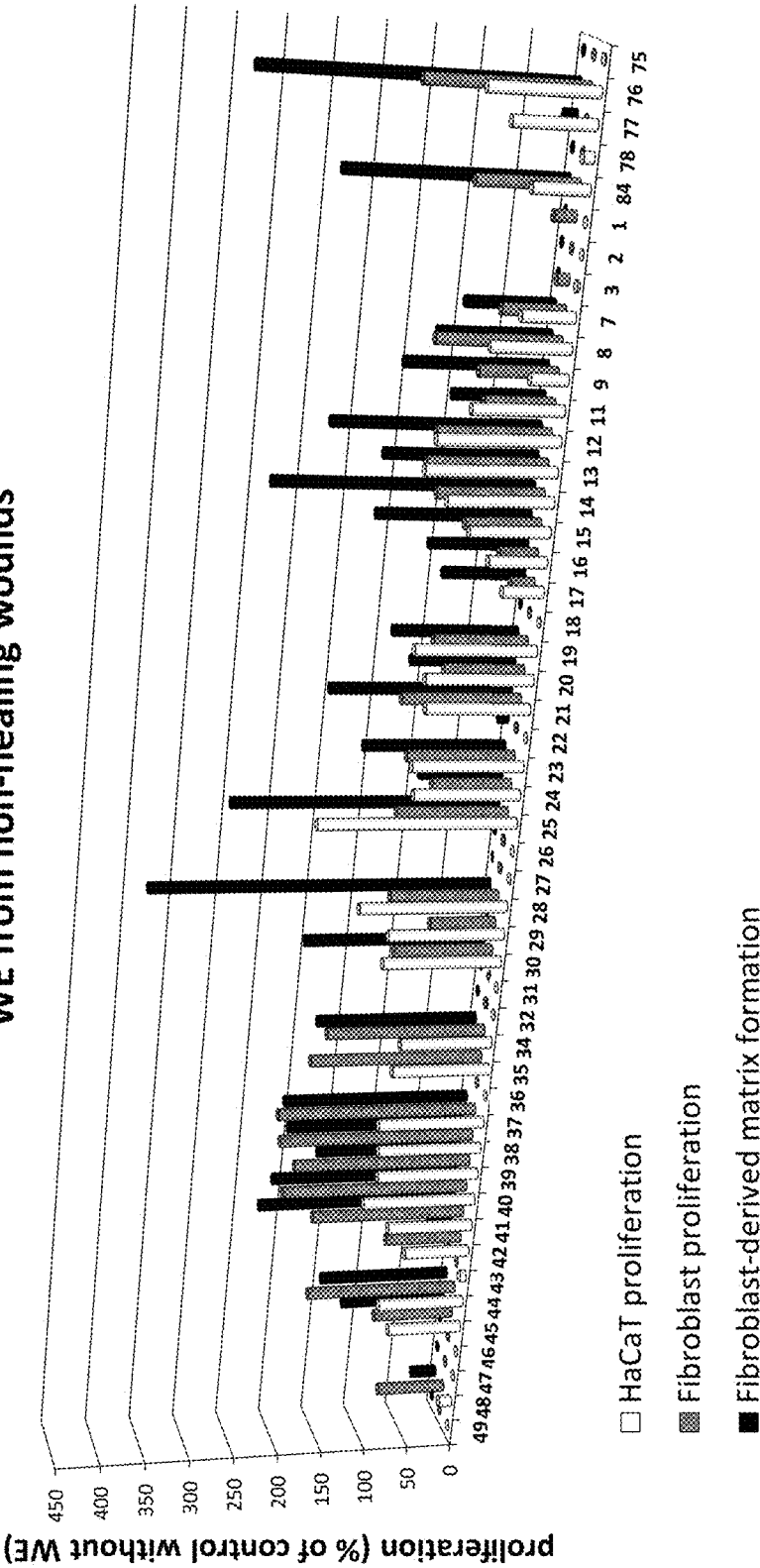

FIG. 17: Proliferation and fibroblast-derived matrix formation in the presence of WE from non-healing wounds. HaCaT proliferation front line columns. Fibroblast proliferation middle line columns. Fibroblast-derived matrix formation back line columns. About half of the non-healing WE inhibit 72-hour proliferation of both primary human fibroblasts and HaCaT keratinocytes, as well as fibroblast-derived matrix formation. All WE tested at 1:25 dilution.

Figure 18:
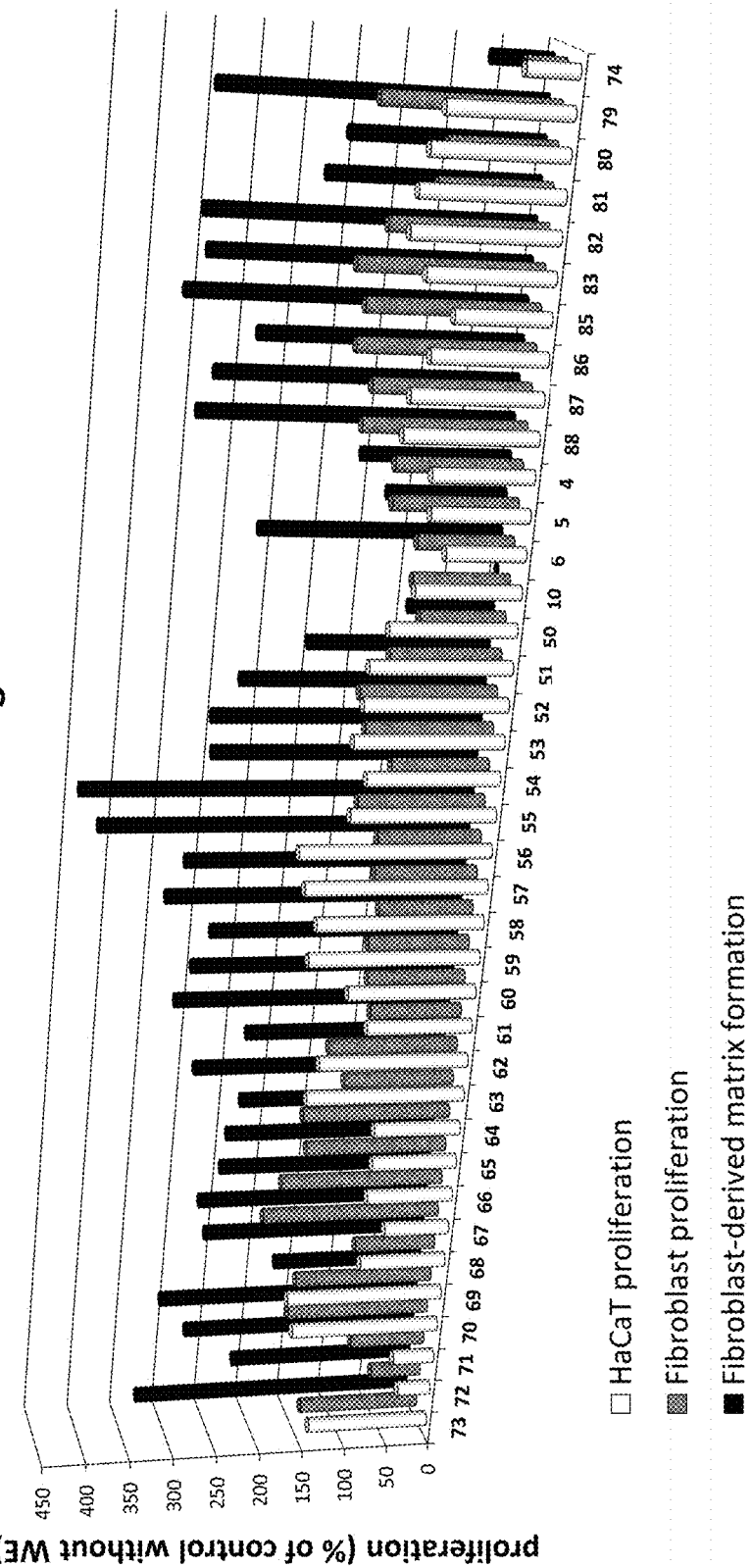

FIG. 18: Proliferation and fibroblast-derived matrix formation in the presence of WE from healing wounds. HaCaT proliferation front line columns. Fibroblast proliferation middle line columns. Fibroblast-derived matrix formation back line columns. Most of the healing WE enhance FDM formation. Only one healing WE inhibits the formation of FDM. For most healing WE, the results in FDM formation assay go in parallel with the HDF and HaCaT proliferation assays. All WE tested at 1:25 dilution.

Figure 19:
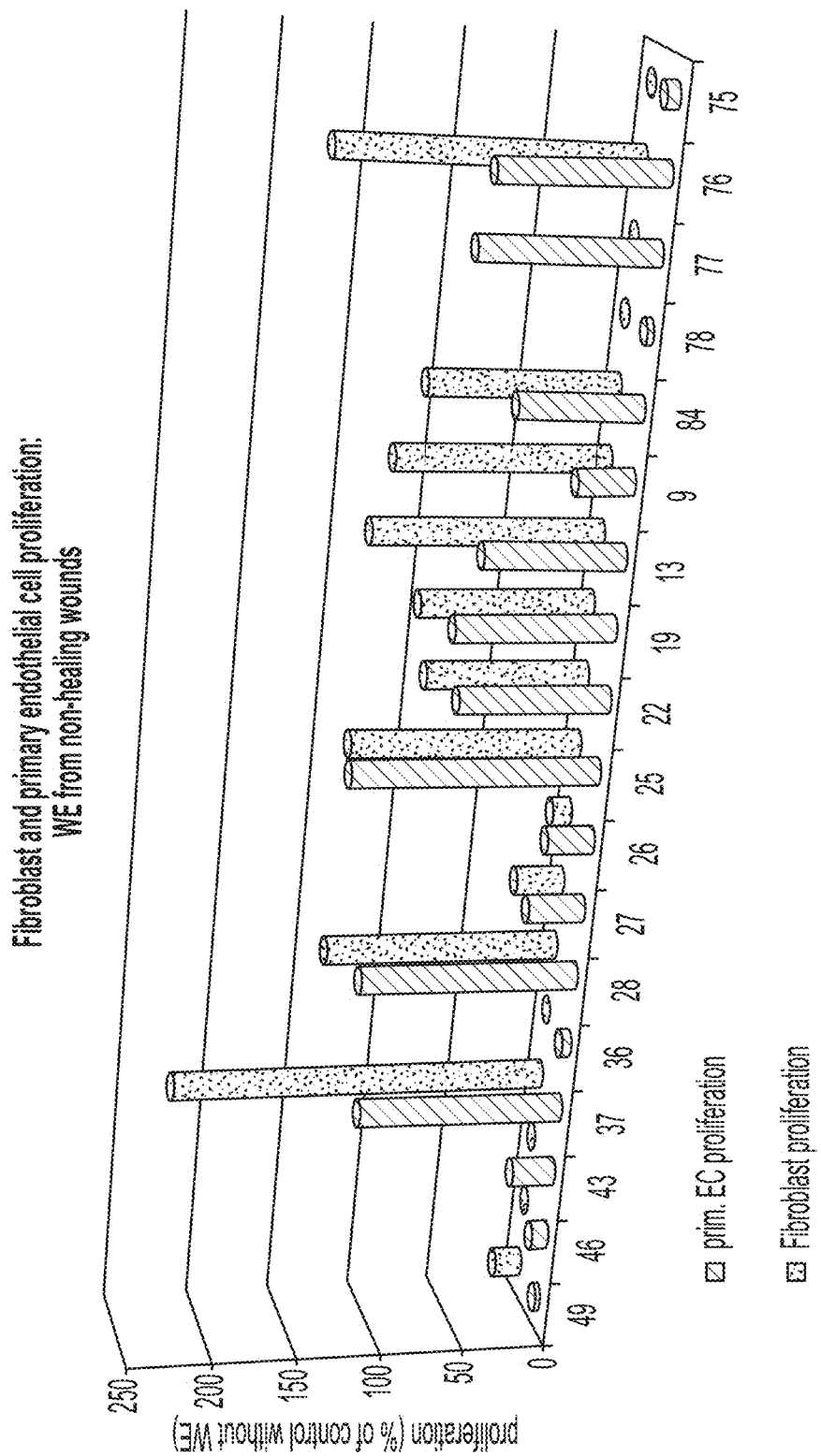

FIG. 19: Fibroblast and primary endothelial cell (EC) proliferation: WE from non-healing wounds. primary EC proliferation front line columns, n=18. fibroblast proliferation back line columns, n=18. WE tested at 1:25 dilution. The activities of 14/18 WE on primary endothelial cell proliferation correlated with their activities on fibroblasts.

Figure 20:
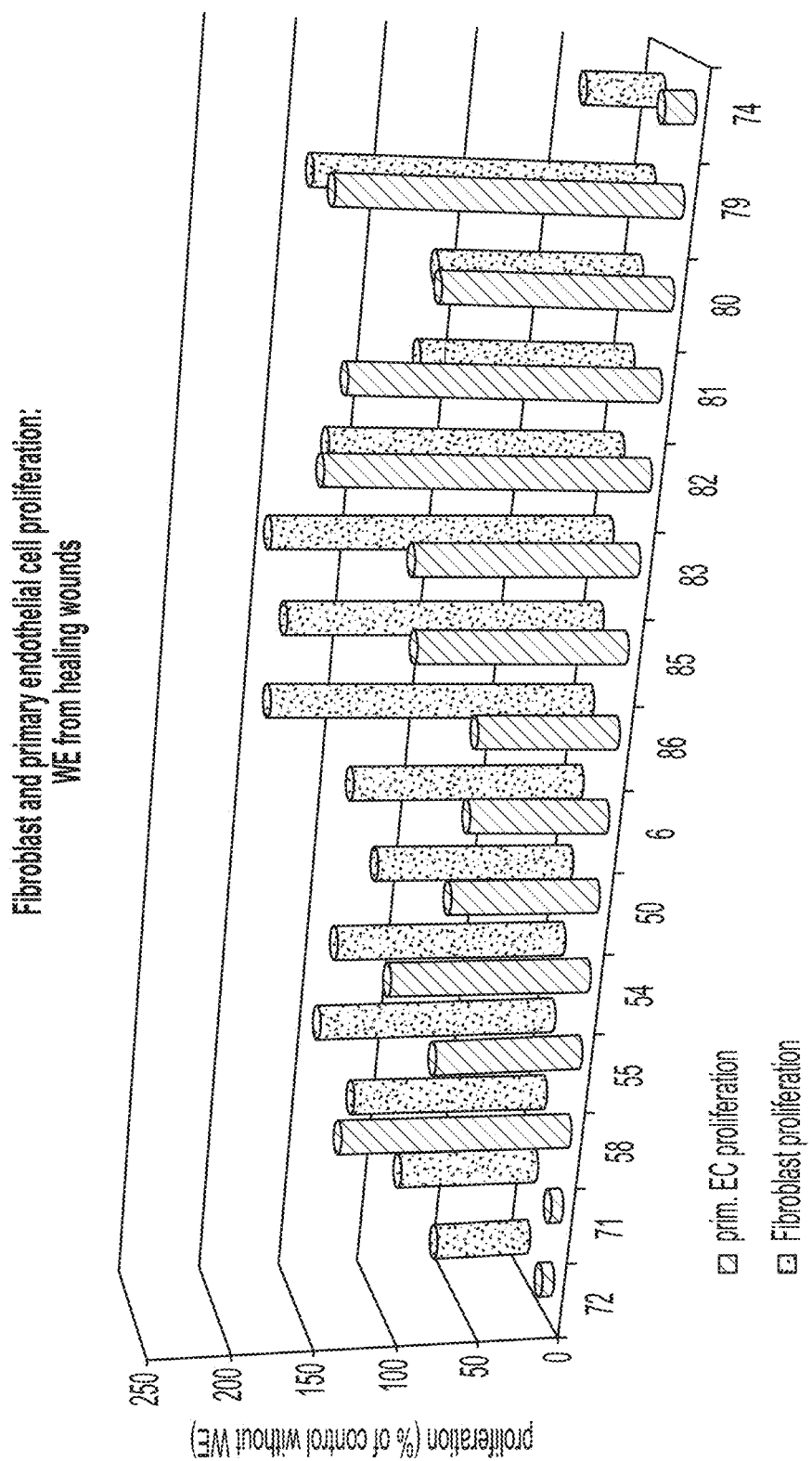

FIG. 20: Fibroblast and primary endothelial cell (EC) proliferation: WE from healing wounds. Primary EC proliferation front line columns, n=15. fibroblast proliferation back line columns, n=15. WE tested at 1:25 dilution. The 3 WE that showed some growth inhibition on fibroblasts were strongly inhibitory on primary endothelial cell proliferation.

Figure 21:
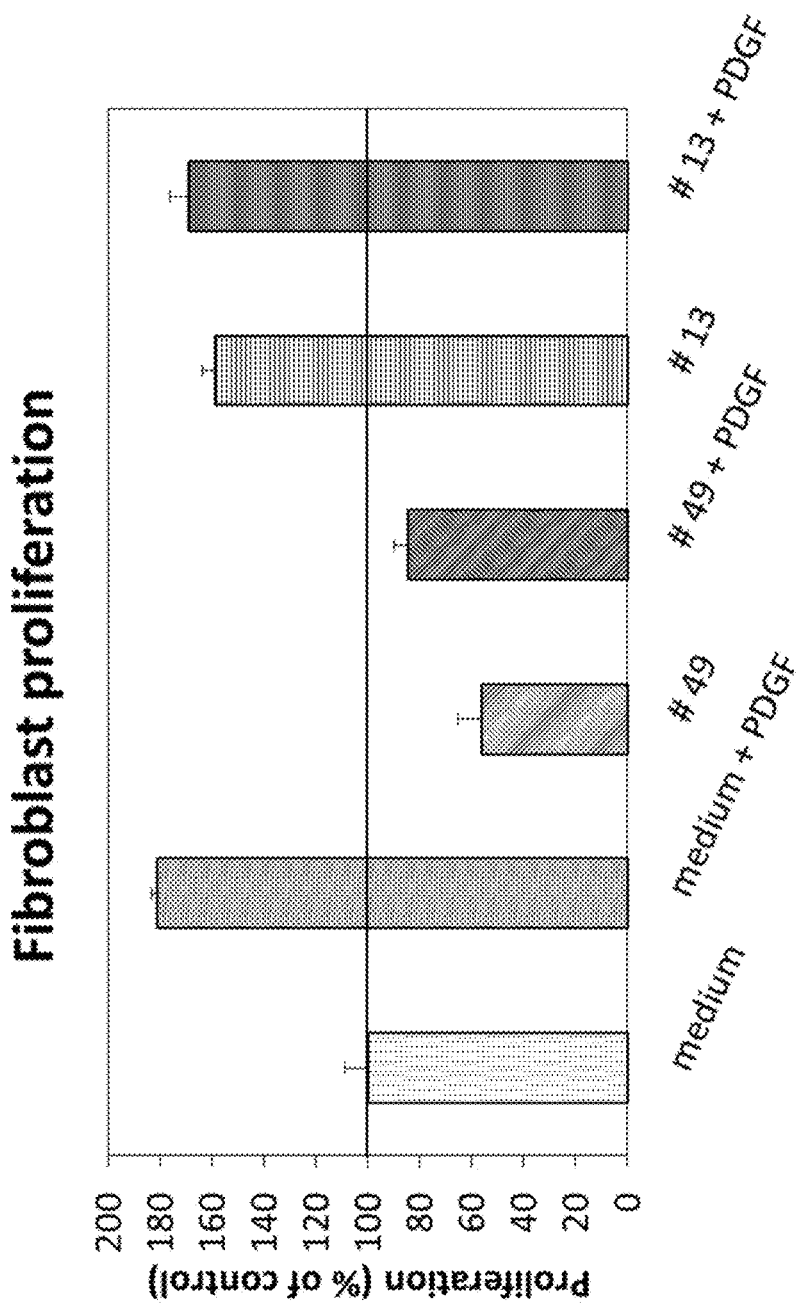

FIG. 21: Relevance of 2D fibroblast assay for wound healing: effect of the registered drug PDGF. The effect of PDGF, is reflected in the 2D fibroblast proliferation assay. PDGF only partially reverses the growth inhibitory effect of an aggressive, non-healing wound exudate (WE #49). WE #13 (healing) has an enhancing effect on HDF proliferation, similar to PDGF.

Figure 22:
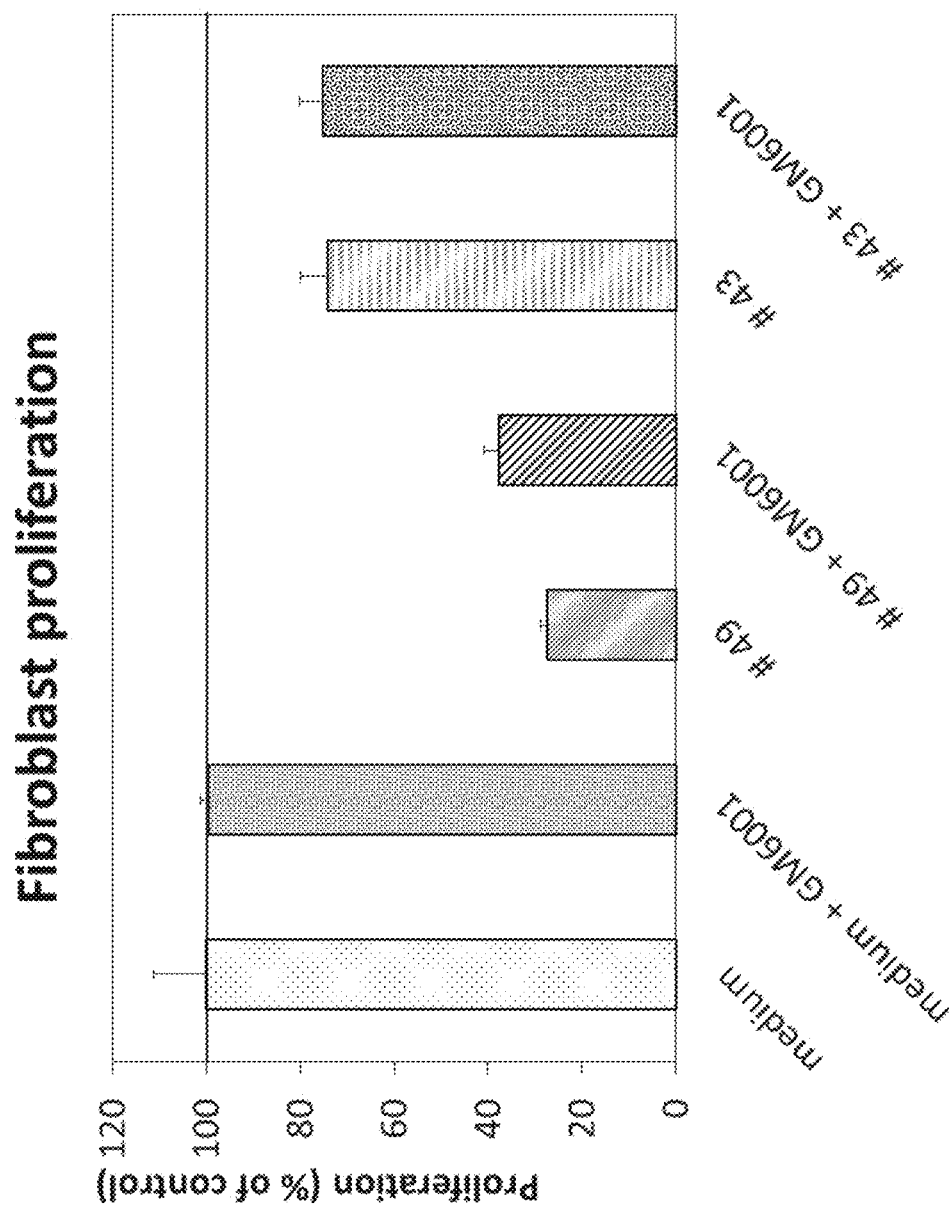

FIG. 22: Fibroblast (HDF) proliferation assay: Effect of metalloproteinase inhibition (GM6001). The pan-MMP inhibitor GM6001 has no effect on medium or WE without MMP activity. GM6001 partially reverses the effect of WE #49, which has the highest MMP activity ($1.8 \times 10^6$ nM).

Figure 23:
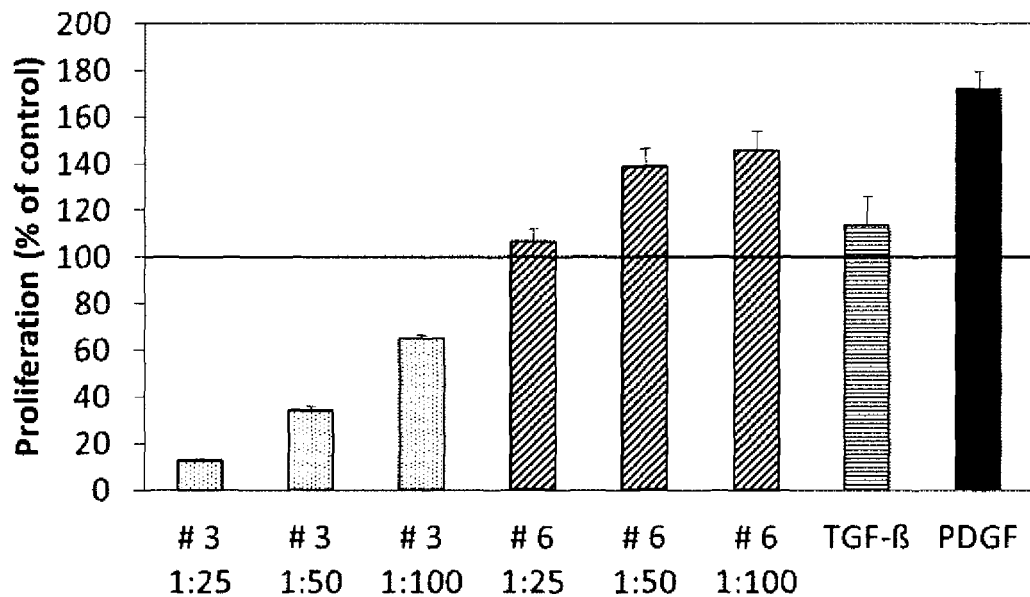
Figure 23:
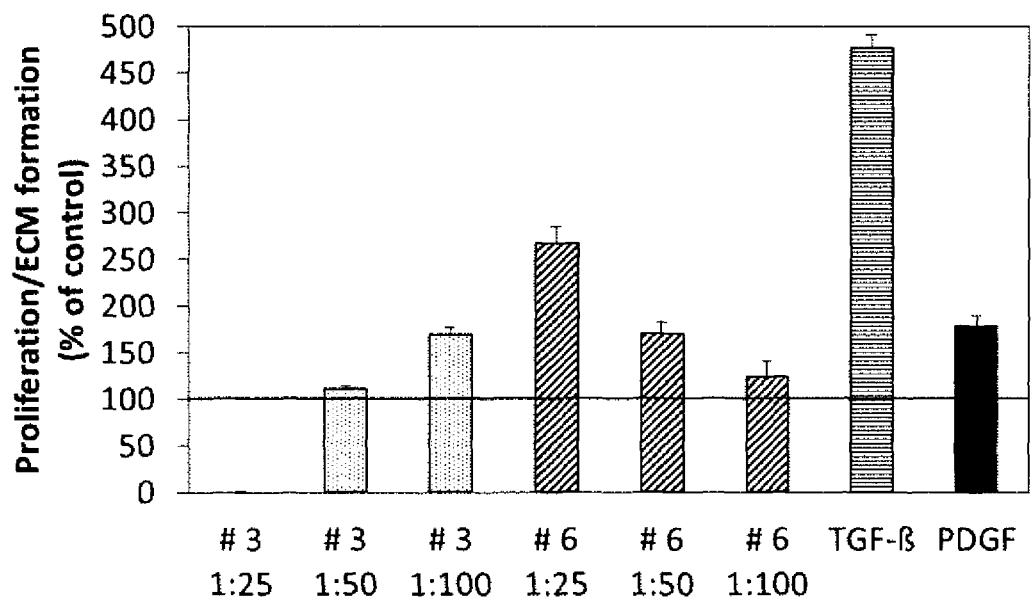

FIG. 23: Proliferation/FDM formation: inhibitory and stimulatory WE. Top: Fibroblast proliferation: Dose-dependent inhibition (non-healing WE). Higher proliferation with lower concentration. Proliferation of some WE approaching positive control (PDGF). Bottom: FDM formation: Dose-dependent inhibition (non-healing WE). Dose-dependent enhancement of FDM formation (some healing WE). Enhancement in line with TGF-β effect.

Figure 24:
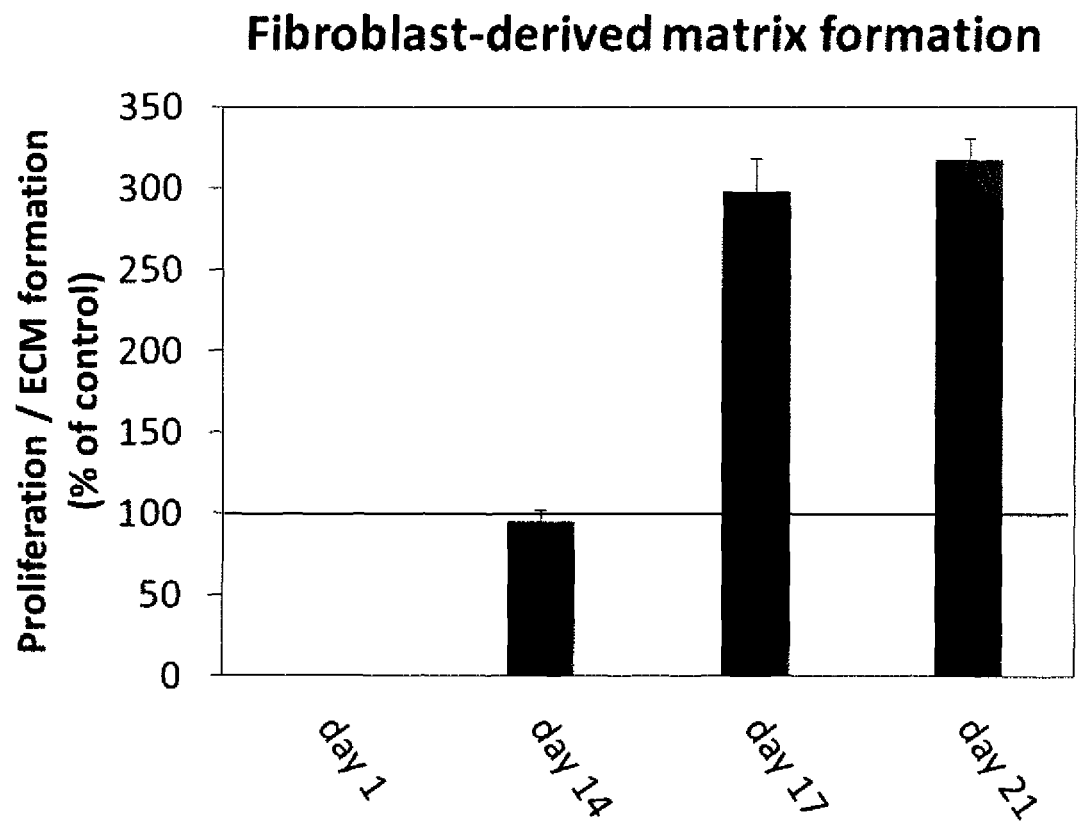

FIG. 24: Relevance of 3D fibroblast assay for wound healing. $1^{st}$ sample (day 1): non-healing ulcer. $2^{nd}$ sample (day 14): beginning granulation. $3^{rd}$ sample (day 17): improvement of healing. $4^{th}$ sample (day 21): healing. The first sample was highly inhibitory of FDM formation. As of the third sample ("improvement") there was a constant increase in FDM formation. Enhanced FDM formation reflects the situation of a healing wound.

Figure 25:
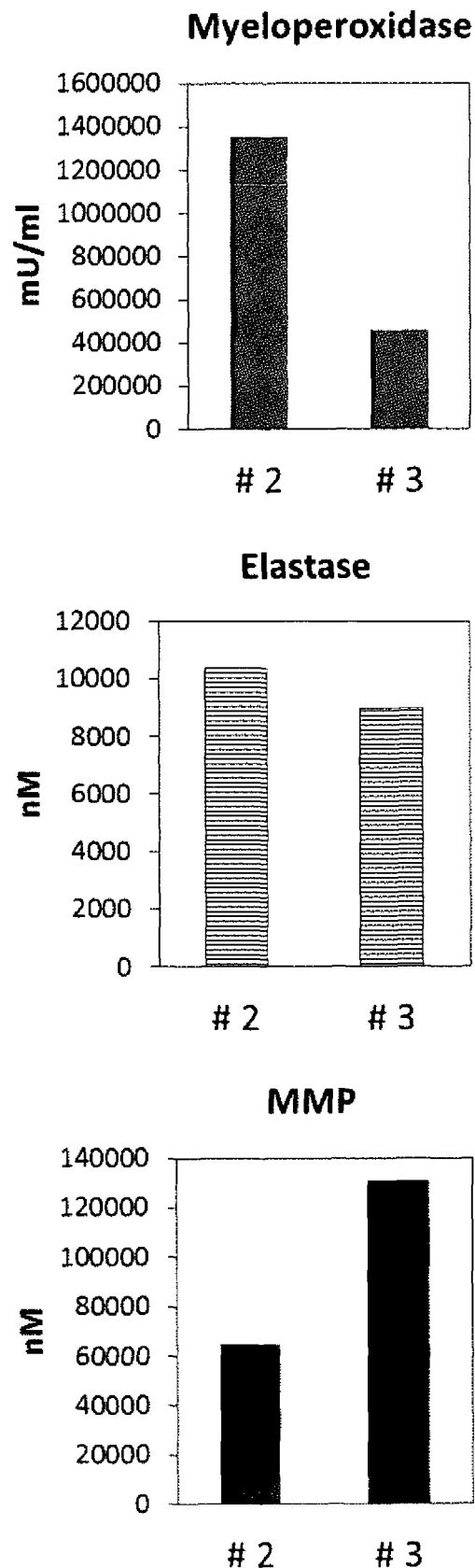

FIG. 25: Patient B: ulcus cruris, right lower leg, positive for *P. aeruginosa* and *S. aureus*. Assessment for sample #2 (1 Jun. 2015): no healing tendency. Assessment for sample #3 (8 Jun. 2015): improvement, but worsening again starting from this time point. Biochemical parameters: MPO and elastase data consistent with decreasing neutrophil influx (due to infection). MMP activities comparatively low (max. 3% of highest value overall)

FIG. 26: Patient B: cytokines as markers. Cytokine levels in exudate consistent with decreasing inflammation, but: Increasing IL-1 induction in macrophages.

Figure 27:
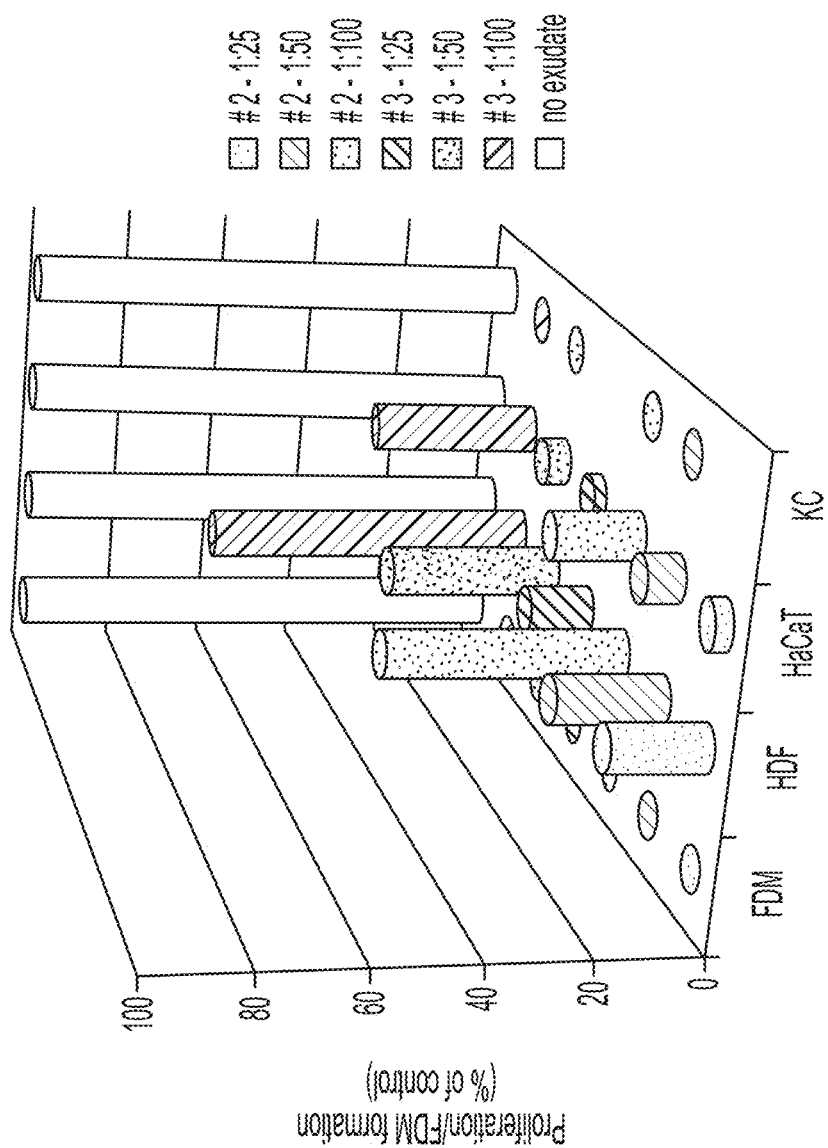

FIG. 27: Patient B: fibroblast and keratinocyte proliferation, FDM formation. Both exudates were aggressively toxic on all fibroblasts and keratinocytes, even though the wound of WE 3 was described as healing. However, one week later the wound had worsened. The experiment shows the predictive value of the methods of the invention.

Figure 28:
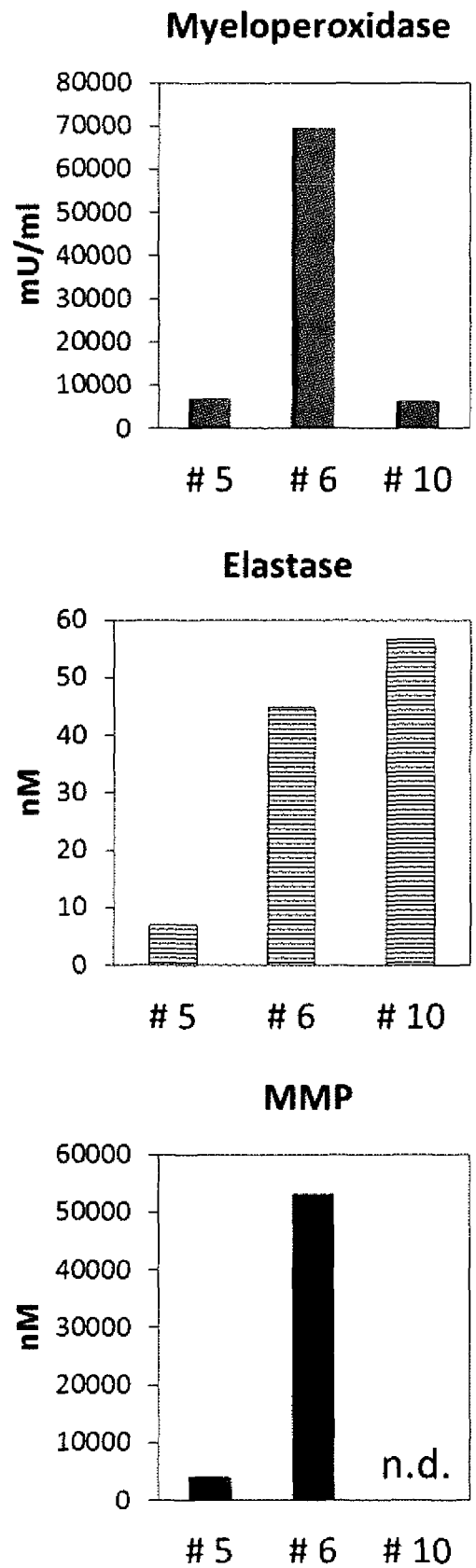

FIG. 28 Patient C: ulcus cruris, lower right leg, healing tendency. Sample #5 (28 Aug. 2015). Assessment for sample #6 (2 Sep. 2015): healing tendency. Assessment for sample #10 (18 Sep. 2015): healing tendency. Biochemical parameters. Low levels of all enzyme activities (max. 5% of highest values overall).

FIG. 29: Patient C: cytokines. Levels in wound exudates vs. macrophage supernatants. Low cytokine levels in exudate (max. 3% of highest values overall). Very low IL-1 induction in macrophages, no TNF-α.

Figure 30:
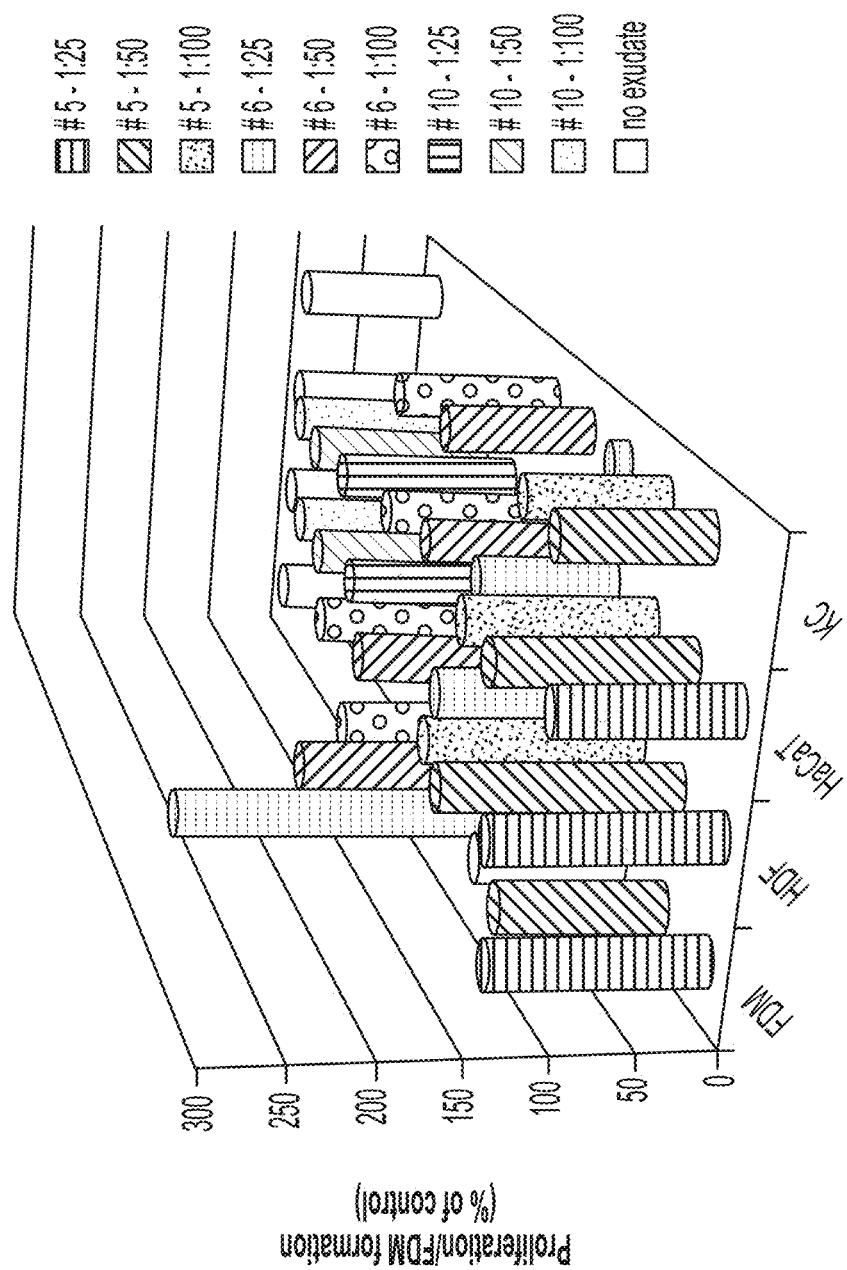

FIG. 30: Patient C: fibroblast and keratinocyte proliferation, FDM formation. None of the exudates showed toxic effects on fibroblasts or KC. Exception: WE #6 at 1:25 dilution on primary KC. One exudate (WE #6) increased FDM formation 2.5 fold at 1:25 dilution. The in vitro data are consistent with clinical phenotype for the individual patient, showing the predictive value of the method.

Figure 31:
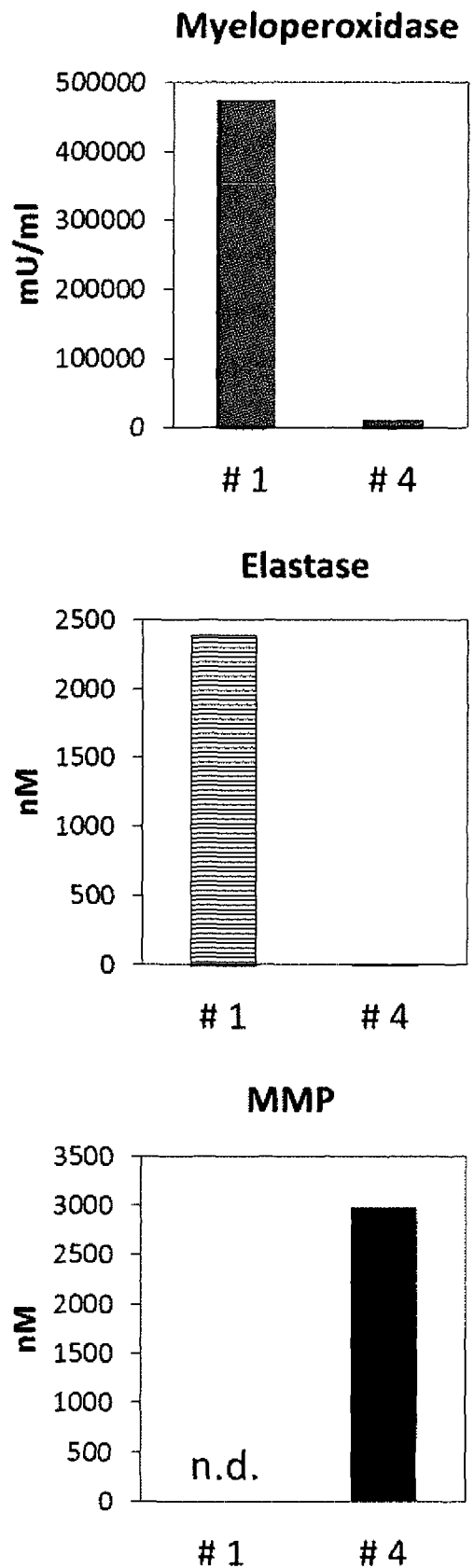

FIG. 31: Patient A: ulcus cruris, lower legs, both sides. Biochemical parameters: MPO and elastase data consistent with decreasing neutrophil influx (18 Mar. 2015: non-healing—23 Jun. 2015: healing). Intermediate MMP activity in sample of healing wound.

FIG. 32: Patient A: cytokines in wound exudates vs. macrophage supernatants. IL-1 levels in exudate consistent with decreasing inflammation, but TNF-α goes in the opposite direction. Low IL-1 induction in macrophages, but intermediate levels of TNF-α in healing wound.

Figure 33:
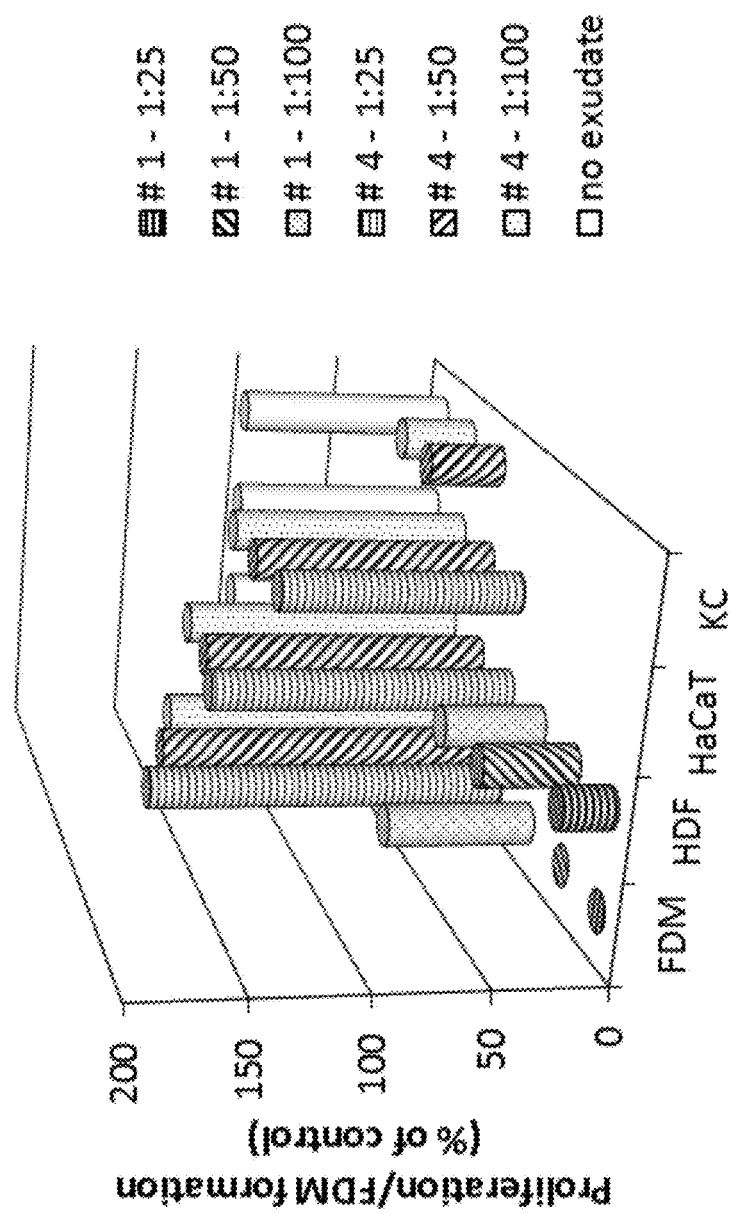

FIG. 33: Patient A: fibroblast and keratinocyte proliferation, FDM formation. The first exudate (18 Mar. 2015—non-healing) was aggressively toxic on all fibroblasts. The following exudate (23 Jun. 2015—healing) showed inhibition only on primary KC. In vitro data are consistent with clinical phenotype, showing the predictive value of the methods of the invention.

FIG. 34: Macrophage cell surface marker expression in fibroblast/macrophage coculture: ratios of CD38/CD209, CD197/CD209 and CD197/CD206. WE from non-healing wounds. n=18. WE tested at 1:25 dilution. Unstimulated cells, i.e. cocultured macrophages in the absence of WE, have ratios of 0.5, 0.6 and 0.6 for CD38/CD209, CD197/CD209 and CD197/CD206, respectively.

FIG. 35: Macrophage cell surface marker expression in fibroblast/macrophage coculture: ratios of CD38/CD209, CD197/CD209 and CD197/CD206. WE from healing wounds. n=18. WE tested at 1:25 dilution. Unstimulated cells, i.e. cocultured macrophages in the absence of WE, have ratios of 0.5, 0.6 and 0.6 for CD38/CD209, CD197/CD209 and CD197/CD206, respectively.

Figure 36:
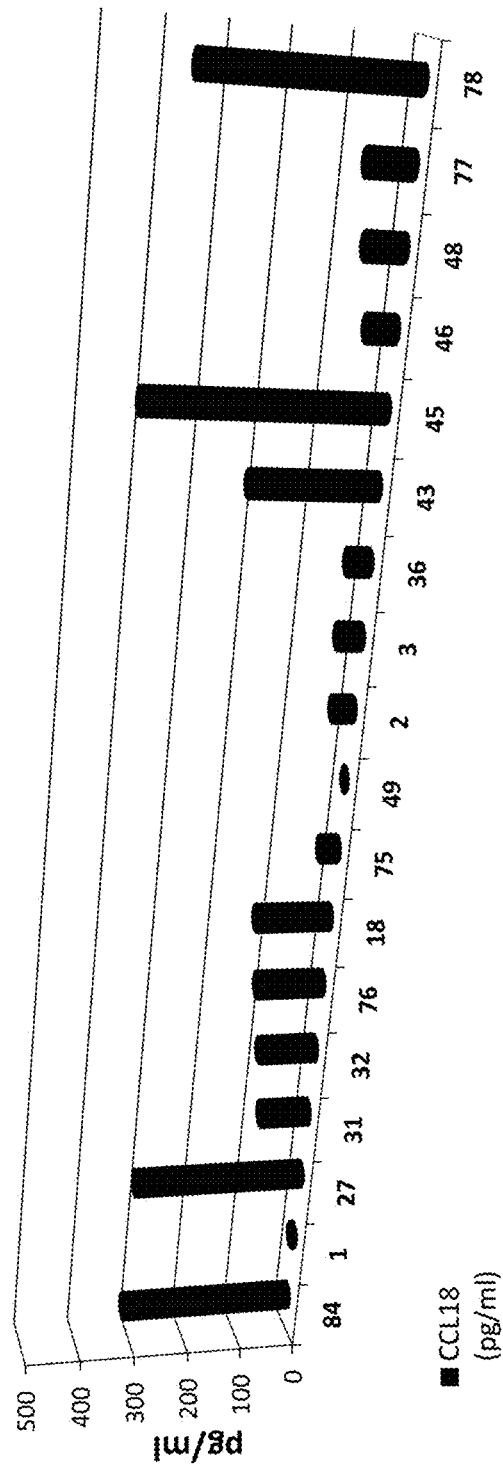

FIG. 36: Macrophage M2 chemokine secretion in fibroblast/macrophage coculture: CCL18. WE from non-healing wounds. n=18. WE tested at 1:25 dilution. Unstimulated cells, i.e. cocultured macrophages in the absence of WE, secreted 70 μg/ml.

Figure 37:
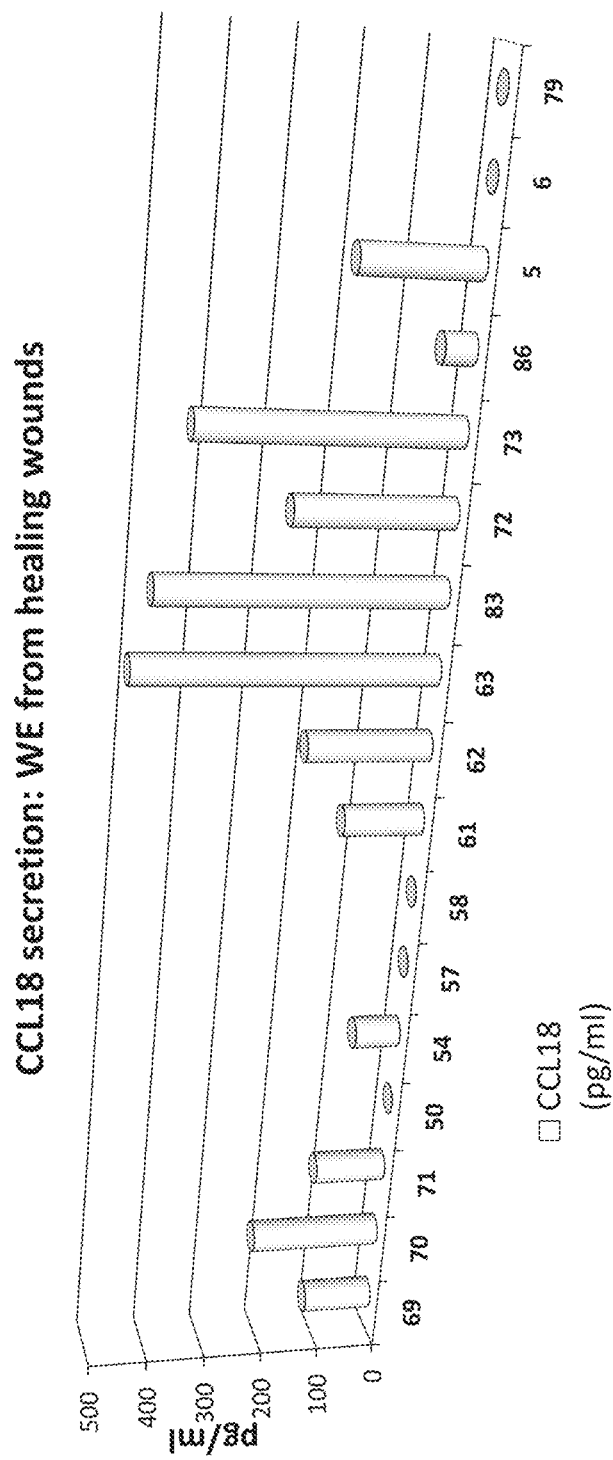

FIG. 37: Macrophage M2 chemokine secretion in fibroblast/macrophage coculture: CCL18. WE from healing wounds. n=18. WE tested at 1:25 dilution. Unstimulated cells, i.e. cocultured macrophages in the absence of WE, secreted 70 μg/ml.

Figure 38:
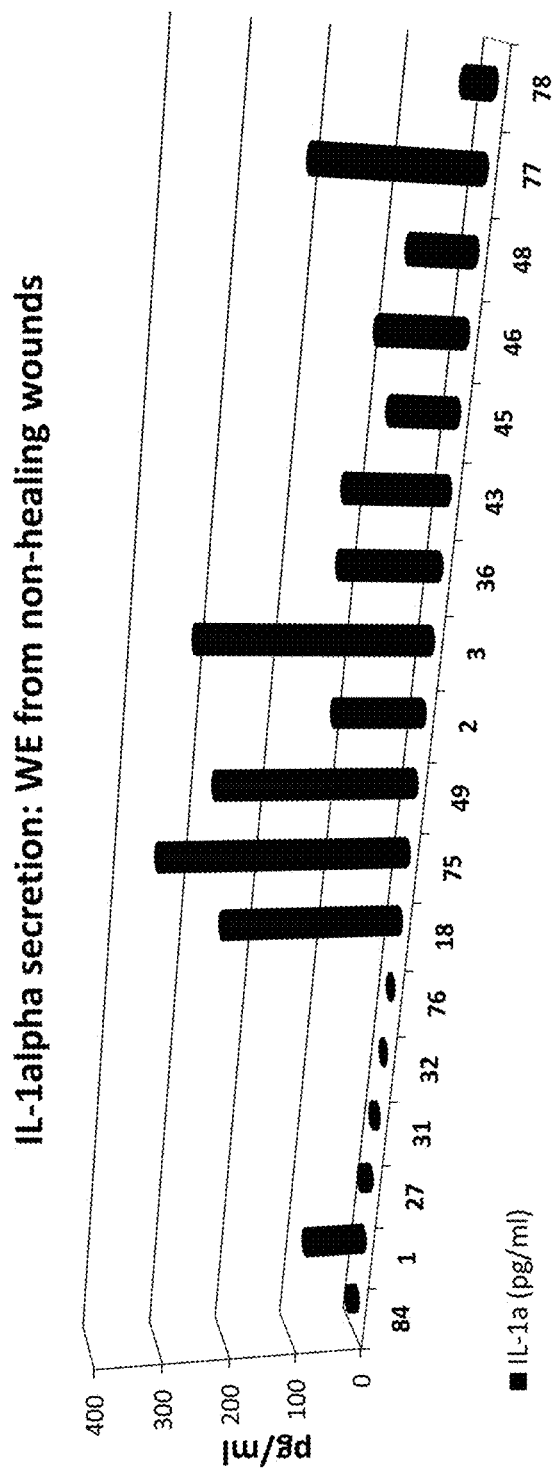

FIG. 38: Proinflammatory cytokine secretion in fibroblast/macrophage coculture: IL-1alpha. WE from non-healing wounds. n=18. WE tested at 1:25 dilution. Unstimulated cells, i.e. cocultured macrophages in the absence of WE, did not secrete any IL-1alpha. In general, IL-1alpha levels in cocultures stimulated with non-healing WE are higher than with healing WE.

Figure 39:
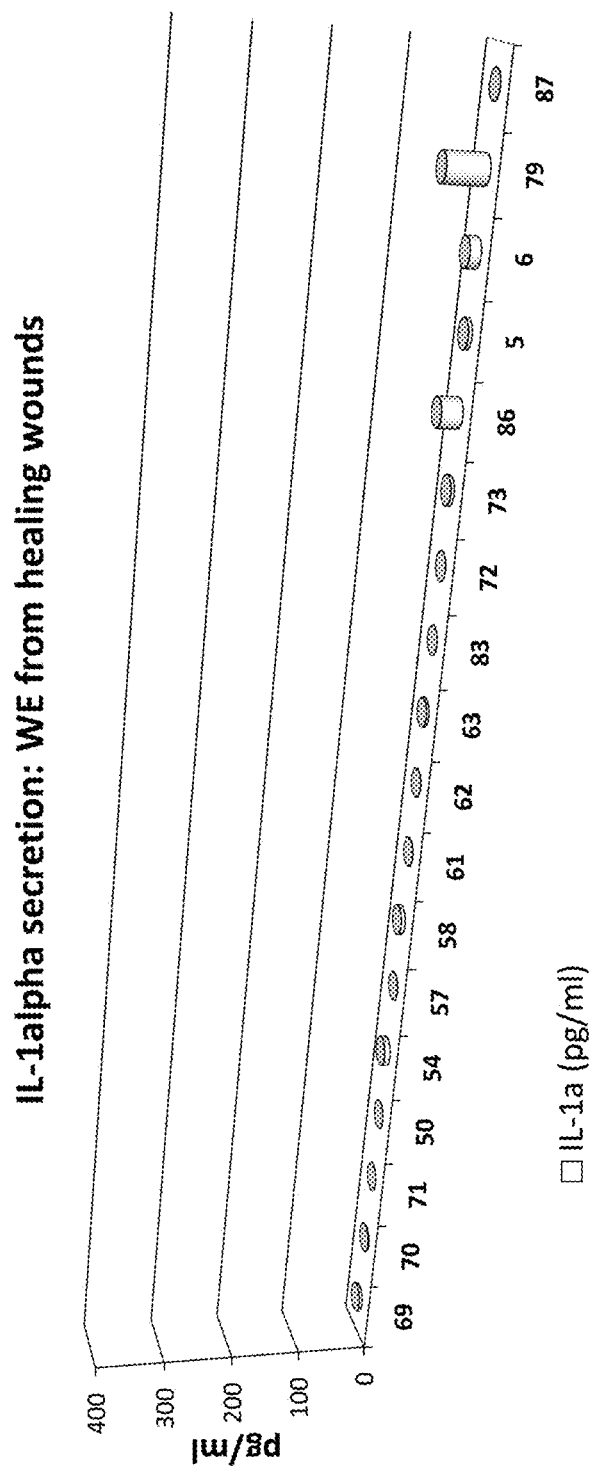

FIG. 39: Proinflammatory cytokine secretion in fibroblast/macrophage coculture: IL-1 alpha. WE from healing wounds. n=18. WE tested at 1:25 dilution. Unstimulated cells, i.e. cocultured macrophages in the absence of WE, did not secrete any IL-1alpha. In general, IL-1alpha levels in cocultures stimulated with healing WE are lower than with non-healing WE.

Figure 40:
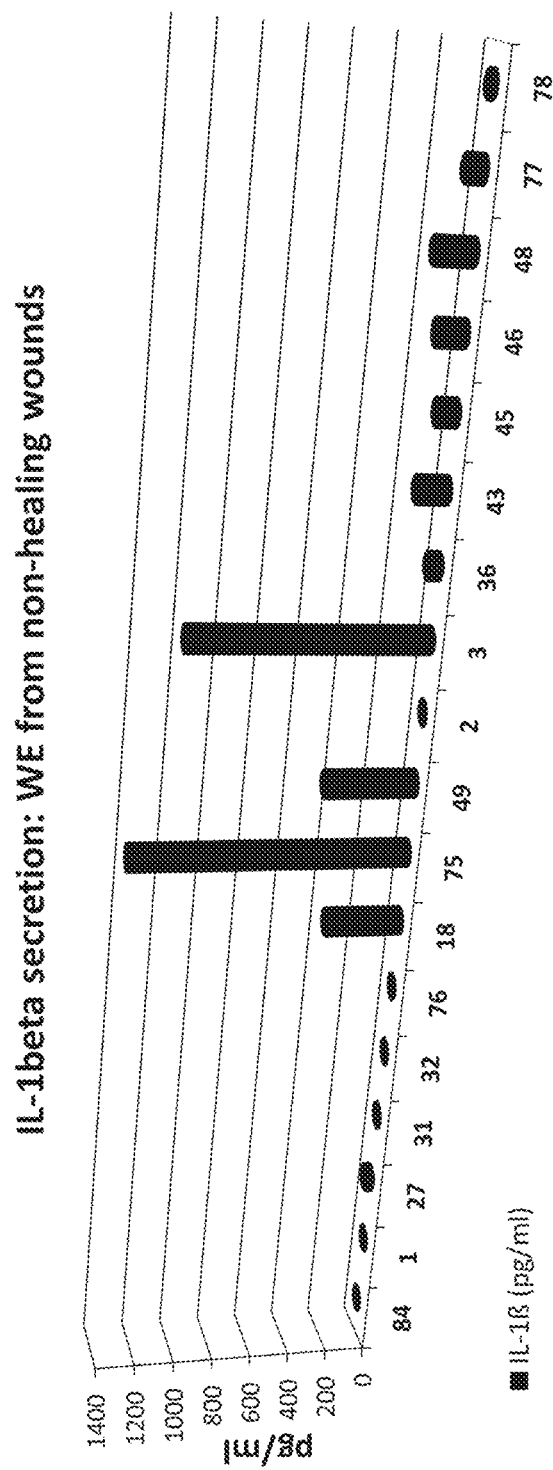

FIG. 40: Proinflammatory cytokine secretion in fibroblast/macrophage coculture: IL-1beta. WE from non-healing wounds. n=18. WE tested at 1:25 dilution. Unstimulated cells, i.e. cocultured macrophages in the absence of WE, did not secrete any IL-1beta. In general, IL-1beta levels in cocultures stimulated with non-healing WE are higher than with healing WE.

Figure 41:
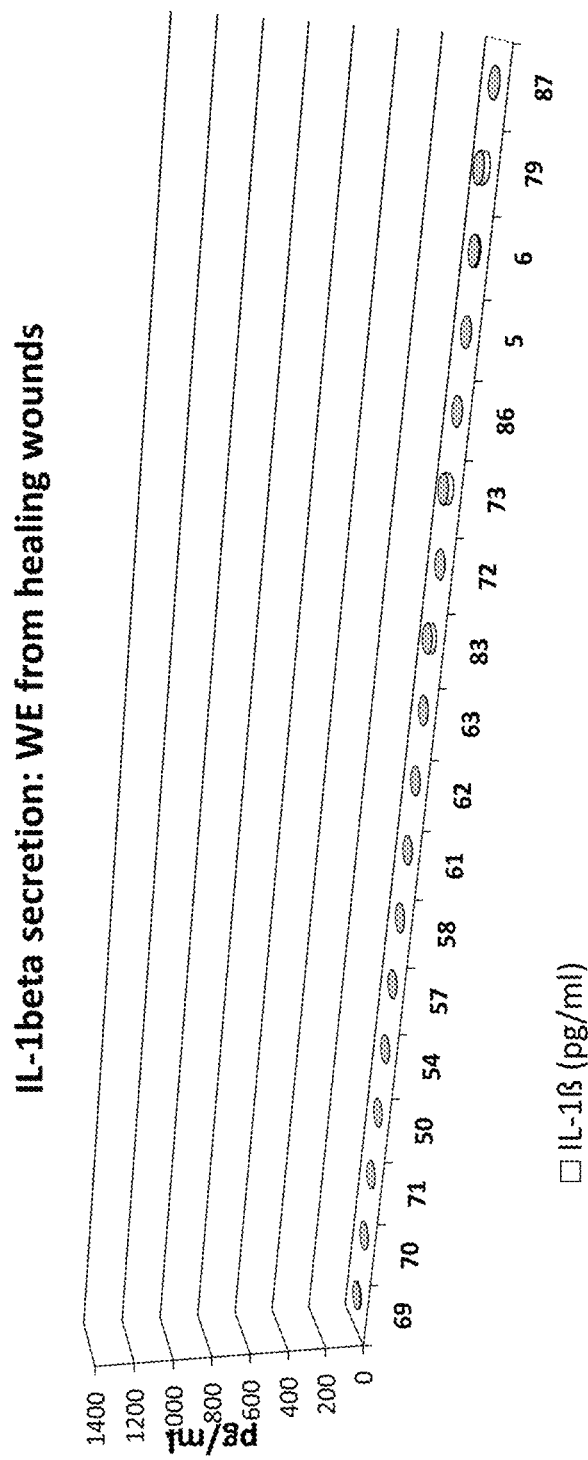

FIG. 41: Proinflammatory cytokine secretion in fibroblast/macrophage coculture: IL-1beta. WE from healing wounds. n=18. WE tested at 1:25 dilution. Unstimulated cells, i.e. cocultured macrophages in the absence of WE, did not secrete any IL-1 beta. In general, IL-1 beta levels in cocultures stimulated with healing WE are lower than with non-healing WE.

Figure 42:
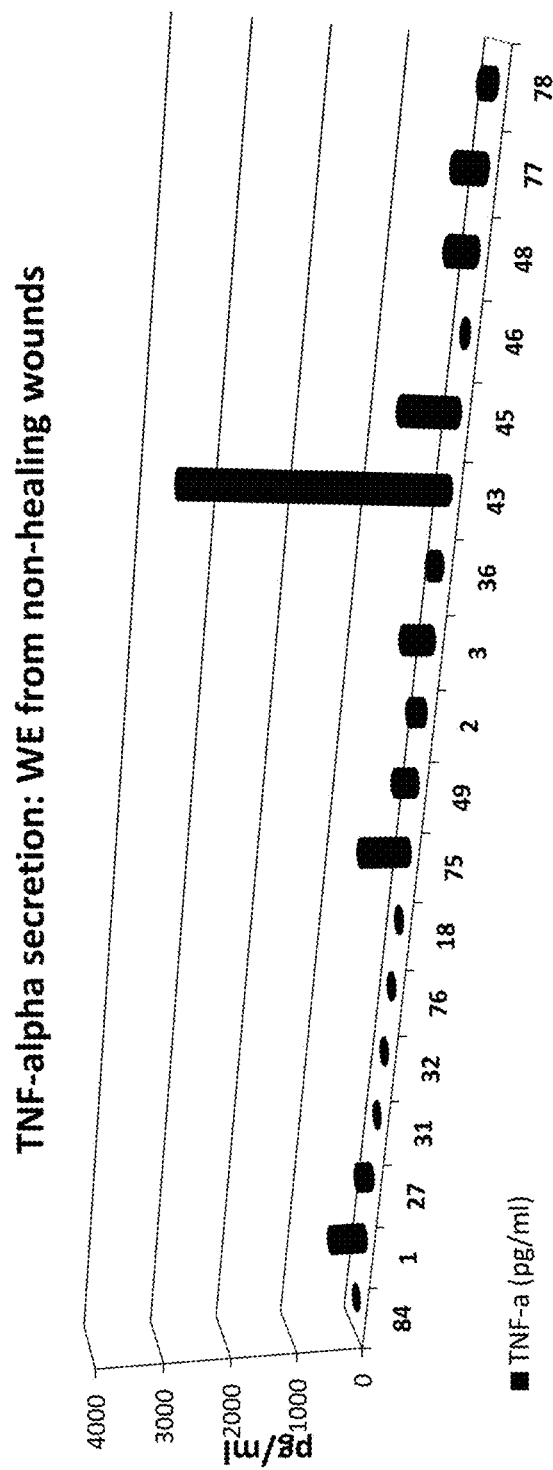

FIG. 42: Proinflammatory cytokine secretion in fibroblast/macrophage coculture: TNF-alpha. WE from non-healing wounds. n=18. WE tested at 1:25 dilution. Unstimulated cells, i.e. cocultured macrophages in the absence of WE, did not secrete any TNF-alpha. In general, TNF-alpha levels in cocultures stimulated with non-healing WE are higher than with healing WE.

Figure 43:
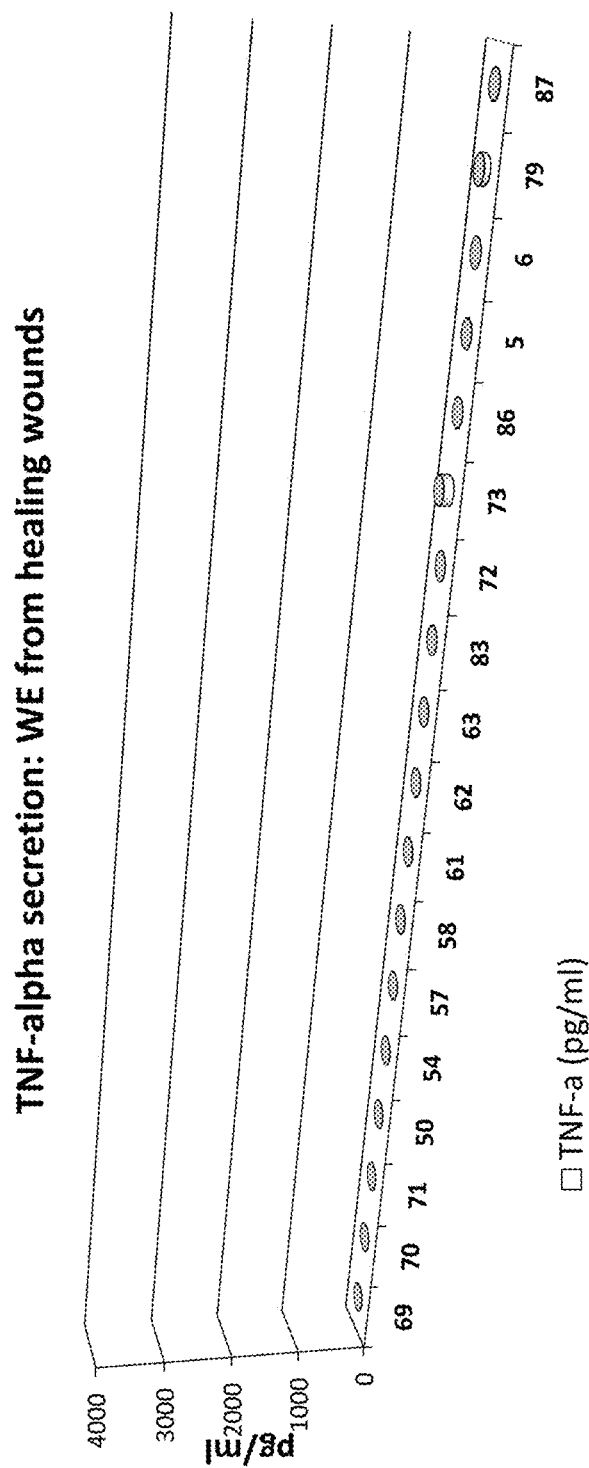

FIG. 43: Proinflammatory cytokine secretion in fibroblast/macrophage coculture: TNF-alpha. WE from healing wounds. n=18. WE tested at 1:25 dilution. Unstimulated cells, i.e. cocultured macrophages in the absence of WE, did not secrete any TNF-alpha. In general, TNF-alpha levels in cocultures stimulated with healing WE are lower than with non-healing WE.

FIG. 44: Relevance of the evaluation of the macrophage M1/M2 cell surface marker ratio in the fibroblast/macrophage coculture assay for wound healing. $1^{st}$ sample (day 1): non-healing ulcer. $2^{nd}$ sample (day 14): beginning granulation. $3^{rd}$ sample (day 17): improvement of healing. $4^{th}$ sample (day 21): healing. The first sample had higher ratios of CD197/CD209 and CD197/CD206 than the samples from the healing phase.

Figure 45:
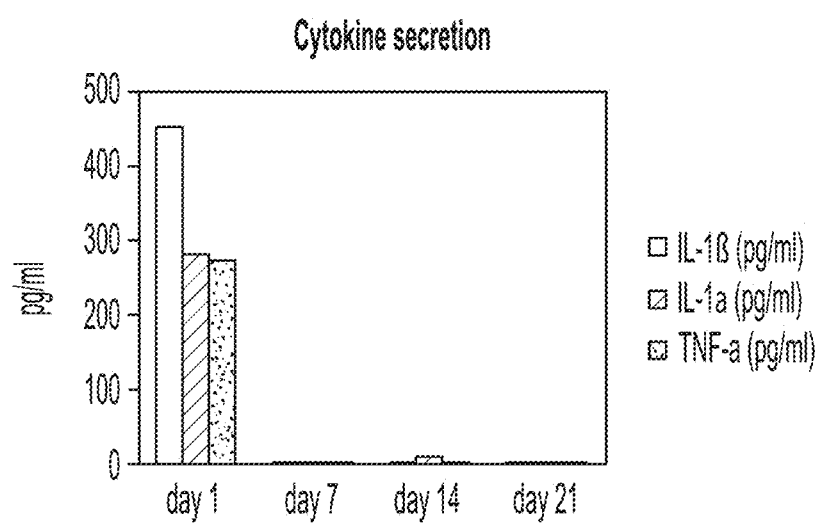

FIG. 45: Relevance of cytokine secretion in the fibroblast/macrophage coculture assay for wound healing. $1^{st}$ sample (day 1): non-healing ulcer. $2^{nd}$ sample (day 14): beginning granulation. $3^{rd}$ sample (day 17): improvement of healing. $4^{th}$ sample (day 21): healing. The first sample had higher levels of IL-1alpha, IL-beta and TNF-alpha than all the others. Decreased cytokine secretion reflects the situation of a healing wound.

EXAMPLES

1. Abbreviations

| Abbreviation | Description |
|---|---|
| DMSO | Dimethylsulfoxide |
| EC | Endothelial cells |
| FCS | Fetal calf serum |
| FDM | Fibroblast-derived matrices |
| HaCaT | Human keratinocyte cell line |
| HBSS | Hank's balanced salt solution |
| HDF | Human dermal fibroblasts |
| M-CSF | Macrophage colony stimulating factor |
| PBS | Phosphate buffered saline |
| PDGF-BB | Platelet-derived growth factor |
| RPMI | Roswell Park Memorial Institute medium |
| SRB | Sulforhodamine B |
| WE | Wound exudate |

2. Assay Systems Using Wound Exudate from Patients with Chronic Wounds to Mimic Wound Chronicity in Experimental Systems Wound exudate (wound fluid) is the extracellular fluid containing a molecular fingerprint of wound cells and can be referred to as a "liquid biopsy". Since removal of wound exudates (WE) can improve wound healing, we reasoned that factors contained within WE critically impede wound healing, e.g. through activation of innate immune cells.

As described below, we could show that wound exudates from chronic wounds are pro-inflammatory in vitro and delay wound healing in in vivo assays. Thus, we conclude that key factors responsible for delayed healing are contained in these exudates.

3. In Vitro Assays

Macrophages, keratinocytes and fibroblasts are perceived as pivotal cells in sustained wound inflammation and resulting wound chronicity. Using WE from chronic wounds as stimulus, we established new test systems in these cell types that are suitable for compound screening, monitoring the healing of a skin wound and/or for identifying a skin wound in an individual as being a non-healing skin wound or healing skin wound. The assays form the basis for our investigations aimed at the identification of inhibitors of WE-induced cell activation for therapy of non-healing chronic ulcers (FIG. 2) as well as for the methods for monitoring the healing of a skin wound and/or for identifying a skin wound in an individual as being a non-healing skin wound or healing skin wound.

Chronic wounds exhibit a pro-inflammatory, M1 macrophage phenotype with high production of pro-inflammatory cytokines, while healing wounds exhibit a M2 phenotype [Sindrilaru A et al (2013) Adv Wound Care 2:357-368]. We investigated the effect of wound exudates (WE) from chronic ulcers on in vitro differentiated macrophages. Based on their ability to mediate release of low or high levels of cytokines by these macrophages, they could be divided into two subsets. In addition, we were able to demonstrate that significantly higher levels of IL-1α, IL-1β and TNF-α were contained in the WE of the subset causing high level cytokine release by macrophages.

3.1. Cellular Assays 3.1.1. Primary Human Dermal Fibroblast (HDF) Proliferation Assay: Measuring the Proliferation of Primary Fibroblast Cells in the Presence of a Wound Exudate Sample Obtained from a Skin Wound of an Individual Primary human dermal fibroblasts (HDF) were purchased from CELLnTEC, Bern. They were routinely grown in Dulbecco's modified Eagle's medium (DMEM) containing 10% FCS, 2 mM glutamine, and 100 U/ml penicillin/100 µg/ml streptomycin. Media, antibiotics, and glutamine were bought from Lonza. The cells were used at passage 10. Cells were trypsinized and seeded at 5000 cells/well in 200 µl into the inner wells of 96-well plates. The outer wells were loaded with sterile water. The cells were allowed to adhere overnight and then incubated for 72 hours at 37° C. under the following conditions: graded compound concentrations or 20 ng/ml PDGF-BB (Tonbo Biosciences # TO-21-8501-U010) in the absence or presence of different dilutions of sterile-filtered WE in medium. For negative control samples, 200 µl medium was added instead of specific stimuli. Alternatively, the cells were seeded into 384-well plates at 2500 cells/well together with test compounds or growth factors and WE or medium in a total volume of 50 µl.

At the end of the 72-hour incubation period, the cells were fixed with 4% paraformaldehyde (Morphisto) for 15 minutes at room temperature and washed 3 times with PBS. A control plate was fixed after the overnight adherence of the cells (day 1) to determine the starting cell number.

Total cellular protein was determined as a measure of cell number by staining the fixed cells with sulforhodamine B (SRB, Sigma). A 0.4% SRB solution in 1% acetic acid was added to the wells for 30 minutes. The wells were then washed with 1% acetic acid until the wash solution remained colorless. After drying, the dye was eluted with 10 mM Tris.HCl, pH8.5, and absorbance was measured either at 550 or 492 nm for lower and higher cell densities, respectively. The average absorbance of the sample representing the day 1 starting cell number (for 96-well plates) was subtracted from the absorbance values of the WE-treated cells.

All experiments were carried out in triplicate for each sample and concentration, and means±standard deviation (SD) were used for the evaluation of the experiment. Results are expressed as percentage of control values for unstimulated cells.

The growth inhibition in primary human fibroblasts (HDF) induced by different dilutions of four selected WE is shown in FIG. 4.

For compound screening in 384-well plates, 50 nl compound solutions in DMSO were spotted by acoustic transfer to yield a final DMSO concentration of 0.1%, which does not affect cell growth (results not shown). For screening with WE, compound results were calculated as % proliferation of untreated and unstimulated control (=100%), and the cut-off for a positive hit was defined as % average proliferation$_{WE}$+ 3*standard deviation, as shown in FIG. 5.

3.1.2. Formation of Fibroblast-Derived Matrices (FDM): Measuring the Fibroblast-Derived Matrix Formation by Primary Fibroblast Cells in the Presence of a Wound Exudate Sample Obtained from a Skin Wound HDF cells were seeded at 5000 cells/well on day −3 into 96-well tissue culture plates (1250 cells/well for 384-well plates), which had been pre-coated for 1 hour at 37° C. with 100 µl of a 0.2% gelatin solution (Sigma). When the cells reached confluence (=day 0), a matrix promoting supplement (vitamin C: 2-phospho-L-ascorbic acid trisodium salt, 100 µg/ml; Sigma) was added together with test samples containing PDGF-BB, TGF-β1 or graded concentrations of compounds−/+WE as described for the HDF proliferation assay. After 4 days, medium was replaced by fresh vitamin C- and stimulus- as well as compound-containing medium, maintaining the conditions initiated on day 0. TGF-β1 and PDGF-BB were included as positive controls to promote FDM formation and cell growth, respectively. After a total incubation time of 8 days, FDM production was measured in fixed cultures via SRB staining and evaluated as described above.

3.1.3. Keratinocyte Proliferation Assay: Measuring the Proliferation of Keratinocyte Cells in the Presence of a Wound Exudate Sample Obtained from a Skin Wound The HaCaT keratinocyte cell line was routinely cultured in DMEM containing 10% FCS, 2 mM glutamine, and 100 U/ml penicillin/100 µg/ml streptomycin. The proliferation assay was carried out as described for HDF cells. Primary human keratinocytes were grown in KBM medium (Lonza CC-3104) containing 0.06 mM calcium and supplemented with growth factors (Lonza CC-4131) on plastic coated with rat tail collagen (40 µg/ml; Gibco) or gelatin (0.2%; Sigma). No antibiotics were used. The proliferation assay was carried out as described for HDF cells.

3.1.4. Primary Human Dermal Microvascular Endothelial Cell Proliferation Assay: Measuring the Proliferation of Endothelial Cells in the Presence of a Wound Exudate Sample Obtained from a Skin Wound The primary human endothelial cells HMVEC-d- (Lonza, CC-2543) were cultured in EGM-2-MV BulletKit medium (Lonza CC-3156 & CC-4147). The proliferation assay was carried out as described for HDF cells.

3.1.5. Primary Human Macrophage Stimulation Assay

Primary human macrophages were differentiated from monocytes, which had been isolated from peripheral blood mononuclear cells (PBMC). PBMC were isolated from buffy coats obtained from the Red Cross, Vienna, using Lymph® Prep (Technoclone). 30 ml of buffy concentrate was diluted 1:2 with PBS, gently underlayered with 15 ml Lymphoprep in a 50 ml falcon tube and centrifuged for 25 minutes at 1800 rpm at 21° C. The interphase was carefully transferred to a new falcon tube and filled up to 50 ml with ice cold PBS. After another centrifugation step (10 minutes, 1200 rpm, 4° C.), the cell pellet was washed 3 times with PBS, resuspended in RPMI medium containing 20% FCS and 10% DMSO and frozen in liquid nitrogen. Monocytes were generated from frozen aliquots using positive selection with the CD14 Beads-Kit (Miltenyi) on an autoMACS-Sorter (Miltenyi) according to the manufacturer's instructions.

For culture and differentiation into macrophages, monocytes were seeded at $4 \times 10^6$ monocytes/well in 6-well-plates (Nunc) and incubated with 20 ng/ml M-CSF (R&D Systems) in RPMI supplemented with 10% FCS, 2 mM glutamine, and 100 U/ml penicillin/100 µg/ml streptomycin in a total volume of 5 ml per well. After 2 days, 2 ml of the supernatant were removed and replaced by 2.5 ml/well of fresh medium containing 20 ng/ml M-CSF. On the third day, microscopic examination revealed differentiation into adherent, frequently elongated cells.

The macrophages were harvested with a rubber scraper, centrifuged at 1200 rpm for 5 minutes, resuspended in serum-free medium and seeded at $2 \times 10^5$ cells/well in 100 µl. After 1 hour at 37° C., 2-fold concentrated stimuli were added in a volume of 100 µl to give the indicated final concentrations. A combination of 100 ng/ml LPS (Sigma) and 50 ng/ml IFN-γ (PeproTech) served as positive control for the induction of cytokine secretion. Graded concentrations of test compounds were prepared in the absence or presence of a 1:100 dilution of sterile-filtered WE. For negative control samples, 100 µl medium was added instead of specific stimuli.

After 24 hours, 200 µl of the supernatants were transferred to U-well plates and frozen at −20° C. for future cytokine analysis (IL-1α, IL-1β, IL-6, TNF-α). The cytokine concentration of the input WE was subtracted from the supernatant levels in order to calculate WE-induced cytokine stimulation.

3.1.6. Human Monocyte-Dermal Fibroblast Co-Cultures as In Vitro Models that Reflect Macrophage Behavior in Human Skin:

Measuring (a) the amount(s) of one or more M1 marker(s) and one or more M2 marker(s) in the supernatant of macrophages incubated with a wound exudate sample obtained from a skin wound, wherein the macrophages are in co-culture with fibroblasts, and (b) measuring the amount(s) and/or frequency distribution(s) of one or more M1 cell surface marker(s) and one or more M2 cell surface marker(s) on macrophages incubated with a wound exudate sample obtained from a skin wound, wherein the macrophages are in co-culture with fibroblasts, (c) measuring the expression level(s) of one or more M1 marker mRNA(s) and one or more M2 marker mRNA(s) in macrophages incubated with a wound exudate sample obtained from a skin wound, wherein the macrophages are in co-culture with fibroblasts, and (d) the amount(s) of one or more cytokine markers selected from IL-1 alpha, IL-1 beta and TNF-alpha in the supernatant of macrophages incubated with a wound exudate sample obtained from a skin wound, wherein the macrophages are in co-culture with fibroblasts.

CD14+ monocytes, isolated from PBMC of healthy donors by magnetic bead separation were incubated either alone or in the presence of primary human dermal fibroblasts (CellNTec) or fibroblast-derived matrices (FDM). FDM had been generated from primary human dermal fibroblasts by a 3-week incubation with the growth supplements vitamin C or insulin and EGF (vitamin C: 2-phospho-L-ascorbic acid trisodium salt, 100 µg/ml; human EGF, 5 ng/ml; human insulin, 5 µg/ml). Alternatively, fibroblast monolayer cultures can be used as well. After 4 days to a week to allow for macrophage differentiation in the presence or absence of M-CSF (25 ng/ml), the cultures were stimulated overnight with IFN-g (50 ng/ml), LPS (100 ng/ml) and IL-4 (25 ng/ml) or combinations thereof as controls for M1 and M2 macrophage induction. In order to evaluate the effects of WE from non-healing and healing wounds, WE were added to the culture medium for overnight stimulation at dilutions raging from 1:25 to 1:100.

Supernatants were harvested and frozen for cytokine determination by ELISA, and cells were harvested and subjected to FACS analysis, gating on the monocyte population. Geometric means of mean fluorescence intensities (MFI) were used to quantify surface marker expression.

Specific mRNA levels are determined as ratios compared to a housekeeping gene; the values obtained are "expression relative to housekeeping gene".

There are 2 possibilities for evaluation: a) the % age of cells positive for a given marker within a population, which is the most commonly used readout in FACS analysis, or b) the quantity of cell surface expression (as surrogate for the number of labelled molecules on the cell surface per individual cell), as measured by the mean fluorescence intensity.

The following readouts were used:

FACS: CD38, CD64 and CD197 for M1 macrophages, CD200 receptor (CD200R), CD206 and CD209 for M2 macrophages, CD163 as a marker of macrophage differentiation. Ratios of M1/M2 cell surface marker expression were calculated.

ELISA: CXCL10 and IL-23p19 for M1 macrophages and CCL22 and CCL18 as M2 macrophage markers, IL-1alpha, IL-1beta and TNF-alpha as pro-inflammatory markers indicative of an M1 phenotype.

mRNA: CD38, CD64 CD38, CD64 and CD197 for M1 macrophages, CD200 receptor (CD200R), CD206 and CD209 for M2 macrophages, CD163 as a marker of macrophage differentiation.

3.2. Biochemical Assays 3.2.1. Protein Assay

Wound exudates were diluted in phosphate buffered saline (PBS) and subjected to a commercial protein assay, Pierce BCA Protein Assay Kit (Thermo Scientific #23225), using bovine serum albumin as a standard in the range of 20-2000 µg/ml. The assay was performed in 96-well ELISA microplates (Greiner #655101) and measured on a TECAN Infinite M200 Pro microtiter plate reader at 562 nm, using Magellan 7.2 software for evaluation.

3.2.2. Myeloperoxidase (MPO) Activity Assay

MPO activity in PBS-prediluted WE samples was determined by oxidation of 3,3',5,5'-Tetramethylbenzidine (TMB) in 96-well ELISA microplates. 10 µl of diluted WE samples were added to 40 µl of assay buffer (78 mM NaH2PO4.H2O, 1.67 mM Na2HPO4, 0.5% HTAB pH 5.40) and then incubated with 40 µl 1×TMB ELISA Substrate Solution (eBioscience #00-4201-56) until blue color developed (up to 30 minutes). MPO from human leukocytes (Sigma M6908-5UN) in assay buffer was used as standard at concentrations from 0.12 to 120 mU/ml. The reaction was stopped by the addition of 45 µl 2NH2SO4, and the samples were measured on a TECAN Infinite M200 Pro microtiter plate reader at 450 nm, using Magellan 7.2 software for evaluation.

3.2.3. Neutrophil Elastase Assay

Elastase activity in WE, pre-diluted 1:2 in PBS, was determined by measuring the fluorescence of the fluorogenic substrate MeOSuc-Ala-Ala-Pro-Val-AMC. 5 µl WE pre-dilutions were added to 20 µl assay buffer (50 mM Tris pH7.4, 600 mM NaCl, 0.05% CHAPS) in 384-well black polystyrene plates (Corning #3573). After addition of 25 µl of elastase substrate V (Merck-Millipore/Calbiochem Cat #324740) at a final concentration of 1.4 µM in assay buffer, the reaction was allowed to proceed for 1 hour. Serial dilutions of elastase from human leukocytes (Sigma E8140-1UN) with 10 nM as highest concentration were used as standards. The reaction was measured on a TECAN Infinite M200 Pro (excitation 380 nm, emission 460 nm) using Magellan 7.2 software for evaluation.

3.2.4. Matrix Metalloproteinase (MMP) Assay

The activity of all matrix metalloproteinases was determined in WE by measuring the fluorescence of the fluorogenic substrate MCA-Lys-Pro-Leu-Gly-Leu-DPA-Ala-Arg-NH2. WE were diluted in assay buffer (100 mM Tris pH=7.4, 100 mM NaCl, 10 mM $CaCl_2$, 10 µM $ZnCl_2$, 0.075% (v/v) Brij35) and 15 µl WE dilutions were transferred to the wells of a 384-well black polystyrene plate (Corning #3573). Active human MMP9 full length protein (Abcam # ab168863) in assay buffer was used as standard at concentrations from 0.31 to 20 nM. After addition of 15 µl of MMP substrate (Biosyntan #50347.1) at a final concentration of 5 µM in assay buffer, the reaction was allowed to proceed at 37° C. for 2 hours. Fluorescence was measured on a TECAN Infinite M200 Pro (excitation 323 nm, emission 382 nm) using Magellan 7.2 software for evaluation.

3.3. Cytokine Assays 3.3.1. Determination of IL-1α

IL-1α in WE and in macrophage supernatants was determined in F96 Maxisorp Nunc Immuno plates (Nunc, #439454) using the hIL1-alpha DuoSet ELISA Kit from R&D Systems (# DY200) according to the manufacturer's instructions. The enzyme reaction was detected with TMB Solution (eBioscience) and stopped by the addition of 50 µl/well 2NH2SO4. Absorbance was read on a Tecan Infinite M200 Pro at 450 nm.

3.3.2. Determination of IL-1a

IL-1β in WE and in macrophage supernatants was determined in F96 Maxisorp Nunc Immuno plates (Nunc, #439454) using the 11-beta ELISA ReadySet-Go Kit from eBioscience (#88-7261-88) according to the manufacturer's instructions. Enzyme reaction and measurement were carried out as described for IL-1α.

3.3.3. Determination of TNF-α

TNF-α in WE and in macrophage supernatants was determined in F96 Maxisorp Nunc Immuno plates (Nunc, #439454) using the TNF-alpha ELISA ReadySet-Go Kit from eBioscience (#88-7346-88) according to the manufacturer's instructions. Enzyme reaction and measurement were performed as described for IL-1α.

3.3.4. Determination of CCL18

CCL18 in WE and in macrophage supernatants was determined in F96 Maxisorp Nunc Immuno plates (Nunc, #439454) using the hCCL18/PARC DuoSet ELISA Kit from R&D Systems (# DY394) according to the manufacturer's instructions. Enzyme reaction and measurement were performed as described for IL-1α.

3.4 Analysis of Macrophage Surface Markers by Flow Cytometry

Cells were harvested and resuspended in FACS buffer (PBS containing 2% FCS). Unspecific antibody binding was prevented by incubation with human Trustain FCR blocking solution (Biolegend, #422302) on ice for 10 minutes. The following fluorochrome-conjugated antibodies from eBioscience (now ThermoFisher Scientific) were used to detect specific surface markers by staining on ice for 30 minutes: CD38-PerCPeFluor710 (#46-0388-42), CD197-APC (#17-1979-42), CD206-AF488 (#53-2069-42), CD209-PerCP Cy5.5 (#45-2099-42). Co-staining with CD45 eFluor (#506 69-0459-42) was used to distinguish macrophages from primary human fibroblasts when analyzed from co-cultures. After washing cells with FACS buffer, they were fixed with 1% paraformaldehyde in PBS and stored at 4° C. in the dark until data were acquired on a Gallios flow cytometer from Beckman Coulter and analyzed with the Kaluza analysis software 1.3.

4.1. Selection of Wound Exudates for Compound Screening in a Method of Screening of the Present Invention Four different wound exudates with different characteristics and very diverse etiologies were selected (to allow the identification of hits which were common to some or all of them). The patient characteristics are summarized in Table 1.

TABLE 1

Characteristics of the patients who provided the screening exudates

| | WE number | | | |
|---|---|---|---|---|
| | # 49 | # 27 | # 43 | # 78 |
| Wound | Foot ulcer | Ulcus cruris arteriosus | "Gamaschen-Ulcus", diabetic patient | Operation wound (after kidney transplantation), diabetic patient |

The different enzyme activities, inflammatory cytokine levels in these WE and cytokine induction in primary human macrophages are shown in FIG. 6.

4.2 Methods of Identifying a Skin Wound in an Individual as being a Non-Healing Skin Wound or Healing Skin Wound and Method for Monitoring the Healing of a Skin Wound in an Individual Using the above cellular assays and biochemical assays, it was surprisingly possible to establish a reliable method of identifying a skin wound in an individual as being a non-healing skin wound or healing skin wound as well as a method for monitoring the healing of a skin wound in an individual.

The evaluation of the assays revealed:
- Growth of primary human fibroblasts was inhibited by 45% of the exudates from non-healing ulcers, but only by 8% of the exudates from healing wounds (all 3 were surgical wounds),
- Most of the exudates that had proven active in the fibroblast proliferation assay inhibited the proliferation of HaCaT keratinocytes and the formation of fibroblast-derived matrices (FDM) as well.
- For the 33 exudates tested in microvascular endothelial cell proliferation, most activities were similar to the effects on fibroblasts,
- Some exudates both from healing and non-healing ulcers showed interesting FDM-enhancing activities.

In particular, the methods of the present invention surprisingly allowed the prediction of whether a defined skin wound in a defined individual exhibits improved or worsened wound healing in the future.

4.3 Methods of Screening of the Invention for Compounds Suitable for Modulating Skin Wound Healing It was surprisingly found that a method for screening for compounds suitable for modulating skin wound healing could be successfully established with the following steps:

Primary assay: fibroblast proliferation

In case a candidate compound if found to be active in the assay, one or more of the following 5 or 6 secondary assays 1) to 5) or 1) to 6) as described above in detail are performed:
1) FDM (3D fibroblast) assay, which measures both proliferation and extracellular matrix formation.
2) HaCaT proliferation
3) Fibroblast/macrophage co-cultures: expression of M1- vs. M2-macrophage surface markers
4) Fibroblast/macrophage co-cultures: M1- vs. M2-macrophage marker secretion
5) Fibroblast/macrophage co-cultures: expression of M1- vs. M2-macrophage marker mRNA
6) Fibroblast/macrophage co-cultures: cytokine marker secretion of IL-1alpha, IL-1beta and TNF-alpha The assays are performed in the presence of wound exudate from at least one individual. A compound is identified as being suitable for modulating skin wound healing in case if the compound is further active in at least one of the five or six secondary assays.

For compound screening in 384-well plates, 50 nl compound solutions in DMSO were spotted by acoustic transfer to yield a final DMSO concentration of 0.1%, which does not affect cell growth (results not shown). For screening with WE, compound results were calculated as % proliferation of untreated and unstimulated control (=100%), and the cut-off for a positive hit was defined as % average proliferation$_{WE}$+ 3*standard deviation, as shown in FIG. 5.

Therefore, the method for screening for compounds suitable for modulating skin wound healing comprises the following steps:

A) measuring the proliferation of primary fibroblast cells in the presence of (i)
 a wound exudate sample obtained from a skin wound of at least one individual, and (ii) at least one candidate compound, and B) performing one, two, three, four or five of the following method steps B1) to B5) or one, two, three, four, five or six of the following method steps B1) to B6) or one, two, three, four or five of the following method steps B1 to B4) and B6) in case the value obtained in A) is at least 10% above or at least 10% below a control value established in the absence of the at least one candidate compound:

B1) measuring the fibroblast-derived matrix formation by primary fibroblast cells in the presence of (i) a wound exudate sample obtained from a skin wound of at least one individual and (ii) said at least one candidate compound, B2) measuring the proliferation of HaCaT cells in the presence of (i) a wound exudate sample obtained from a skin wound of at least one individual and (ii) said at least one candidate compound, B3) measuring the amount(s) of one or more M1 marker(s) and one or more M2 marker(s) in the supernatant of macrophages incubated with (i) a wound exudate sample obtained from a skin wound of at least one individual and (ii) said at least one candidate compound, wherein the macrophages are in co-culture with fibroblasts, B4) measuring the amount(s) and/or frequency distribution(s) of one or more M1 cell surface marker(s) and one or more M2 cell surface marker(s) on macrophages incubated with (i) a wound exudate sample obtained from a skin wound of at least one individual and (ii) said at least one candidate compound, wherein the macrophages are in co-culture with fibroblasts, B5) measuring the expression level(s) of one or more M1 marker mRNA(s) and one or more M2 marker mRNA(s) in macrophages incubated with (i) a wound exudate sample obtained from a skin wound of at least one individual and (ii) said at least one candidate compound, wherein the macrophages are in co-culture with fibroblasts, B6) measuring the amount(s) of one or more cytokine markers in the supernatant of macrophages incubated with (i) a wound exudate sample obtained from a skin wound of at least one individual and (ii) said at least one candidate compound, wherein the macrophages are in co-culture with fibroblasts, and wherein the one or more cytokine markers are selected from IL-1alpha, IL-1 beta and TNF-alpha, wherein the compound is identified as being suitable for modulating skin wound healing, in case at least one value obtained in B1) to B5) or B1 to B6) or B1 to B4) and B6) is at least 10% above or at least 10% below a control value established in the absence of the candidate compound, preferably wherein the method steps pursuant to A) and B1) to B5) or A) and B1) to B6) or B1 to B4) and B6) are performed as described in the Examples and/or the remaining parts of present application.

The invention claimed is:
1. A method for screening for compounds suitable for improving skin wound healing of a non-healing skin wound, comprising the following steps:
   A) measuring the proliferation of primary human fibroblast cells from healthy individuals in the presence of
      (i) a wound exudate sample or wound biofilm sample obtained from a non-healing skin wound of at least one human individual, and (ii) at least one candidate compound,
    wherein (i) said wound exudate sample or said wound biofilm sample, and (ii) said at least one candidate compound are incubated with said primary human fibroblast cells and are added to said primary human fibroblast cells for incubation simultaneously, or sequentially,
        wherein in case of simultaneous administration, said wound exudate sample or wound biofilm sample is mixed with said at least one candidate compound, and
B) performing one, two, three, four or five of the following method steps B1) to B5) or one, two, three, four five or six of the following method steps B1) to B6) in case the value obtained in A) is at least 10% above a control value established in the absence of the at least one candidate compound:
    B1) measuring the fibroblast-derived matrix formation by primary human fibroblast cells from healthy individuals in the presence of (i) a wound exudate sample or wound biofilm sample obtained from a non-healing skin wound of the at least one human individual and (ii) said at least one candidate compound,
        wherein (i) said wound exudate sample or said wound biofilm sample, and (ii) said at least one candidate compound are incubated with said primary human fibroblast cells and are added to said primary human fibroblast cells for incubation simultaneously, or sequentially,
            wherein in case of simultaneous administration, said wound exudate sample or wound biofilm sample is mixed with said at least one candidate compound,
    B2) measuring the proliferation of keratinocyte cells, wherein said keratinocyte cells are selected from the group consisting of primary human keratinocyte cells from healthy individuals and cells of a human keratinocyte cell line, in the presence of (i) a wound exudate sample or wound biofilm sample obtained from a non-healing skin wound of the at least one human individual and (ii) said at least one candidate compound,
    B3) measuring the amount(s) of one or more M1 marker(s) and one or more M2 marker(s) in a supernatant of macrophages, which macrophages are generated from primary human monocytes from healthy individuals, incubated with (i) a wound exudate sample or wound biofilm sample obtained from a non-healing skin wound of the at least one human individual and (ii) said at least one candidate compound, wherein the macrophages are in co-culture with primary human fibroblasts from healthy individuals, wherein the one or more M1 markers are selected from CXCL10 or IL-23p19, and the one or more M2 markers are selected from CCL22 or CCL18,
    B4) measuring the amount(s) and/or frequency distribution(s) of one or more M1 cell surface marker(s) and one or more M2 cell surface marker(s) on macrophages, which macrophages are generated from primary human monocytes from healthy individuals, incubated with (i) a wound exudate sample or wound biofilm sample obtained from a non-healing skin wound of the at least one human individual and (ii) said at least one candidate compound, wherein the macrophages are in co-culture with primary human fibroblasts from healthy individuals, wherein the one or more M1 cell surface markers are selected from the group consisting of CD38, CD64 and CD197, and wherein the one or more M2 cell surface markers are selected from the group consisting of CD200 receptor, CD206 and CD209,
    B5) measuring the expression level(s) of one or more M1 marker mRNA(s) and one or more M2 marker mRNA(s) in macrophages, which macrophages are generated from primary human monocytes from healthy individuals, incubated with (i) a wound exudate sample or wound biofilm sample obtained from a non-healing skin wound of the at least one human individual and (ii) said at least one candidate compound, wherein the macrophages are in co-culture with primary human fibroblasts from healthy individuals, wherein the one or more M1 marker mRNA(s) are selected from the group consisting of CD38, CD64, CD197, CXCL10 and IL-23p19, and the one or more M2 marker mRNA(s) are selected from the group consisting of CD200 receptor (CD200R), CD206, CD209, CCL22 and CCL18,
    B6) measuring the amount(s) of one or more cytokine markers in a supernatant of macrophages, which macrophages are generated from primary human monocytes from healthy individuals, incubated with (i) a wound exudate sample or wound biofilm sample obtained from a non-healing skin wound of the at least one human individual and (ii) said at least one candidate compound, wherein the macrophages are in co-culture with primary human fibroblasts from healthy individuals, and wherein the one or more cytokine markers are selected from the group consisting of IL-1 alpha, IL-1beta and TNF-alpha,
    wherein said wound exudate sample or wound biofilm sample used in step A) and optionally one, two, three, four or five of said method steps B1) to B5) or one, two, three, four five or six of said method steps B1) to B6) inhibits the proliferation of said primary human fibroblast cells in the absence of said at least one candidate compound, and
    wherein the compound is identified as being suitable for improving skin wound healing of a non-healing skin wound, in case at least one value obtained in B1) and B2) is at least 10% above or at least one value obtained in B3) to B5) or B3) to B6) is at least 10% below a control value established in the absence of the candidate compound.

2. The method for screening for compounds of claim 1, wherein
    a) the at least one compound is selected from a small molecule, a hormone, sugar, protein, peptide, polymer, biological, an antibody or derivative thereof, or a conjugate thereof, a nucleic acid, or one or more cell(s), and/or
    b) the at least one compound is selected from the group consisting of an immunomodulatory agent, an antibiotic, an antiinfective, a growth factor, a cytokine, an antiproliferative agent and an agent stimulating proliferation, and/or
    c) the at least one compound is a single compound, or 2, 3, 4, 5, or more different compounds, wherein the 2, 3, 4, 5, or more different compounds may be present in a single composition or in 2 or more separate compositions, and/or d) the values are measured at least in triplicate and/or a statistical significance is established in B), and/or the compound is identified as being suitable for improving skin wound healing of a non-healing skin wound, in case at least one value obtained in B1) and B2) is at least 10% above or at least one value obtained in B3) to B5) or B3) to B6) is at least 10% below a control value established in the absence of the candidate compound with statistical significance.

3. The method for screening for compounds of claim 2, wherein the immunomodulatory agent is an immunosuppressive agent.

4. The method for screening for compounds of claim 2, wherein said statistical significance is p≤0.05, p≤0.001 or p≤0.001.

5. The method for screening for compounds of claim 2, wherein said biological is a protein, a peptide, an antibody or derivative thereof, or a conjugate thereof, a nucleic acid, or one or more cell(s).

6. The method for screening for compounds of claim 5, wherein said nucleic acid is a viral agent.

7. The method for screening for compounds of claim 5, wherein said one or more cell(s) are one or more genetically modified cell(s).

8. The method for screening for compounds of claim 1, wherein
   i) measuring the proliferation of primary fibroblast cells from healthy individuals in the presence of a wound exudate sample or wound biofilm sample obtained from a non-healing skin wound includes the following steps:
      (i) culturing primary human dermal fibroblast cells,
      (ii) incubating the fibroblast cells on a solid support, thereby allowing the fibroblast cells to adhere to the support,
      (iii) contacting the fibroblast cells with the wound exudate sample or wound biofilm sample, which is optionally diluted, wherein the contacting may be performed before or after adherence of the fibroblast cells occurs,
      (iv) determining the amount of the primary fibroblast cells, and/or
   ii) measuring the fibroblast-derived matrix formation by primary fibroblast cells in the presence of a wound exudate sample or wound biofilm sample obtained from a non-healing skin wound includes the following steps:
      (i) seeding primary human dermal fibroblast cells on a support,
      (ii) culturing the fibroblast cells on the support until confluence is reached,
      (iii) contacting the fibroblast cells with (i) a matrix promoting supplement, and (ii) the wound exudate sample or wound biofilm sample, which is optionally diluted, wherein (i) and (ii) may be contacted simultaneously or sequentially,
      (iv) determining the amount of the fibroblast-derived matrix, and/or
   iii) measuring the proliferation of keratinocyte cells, wherein said keratinocyte cells are selected from the group consisting of primary human keratinocyte cells from healthy individuals and cells of a human keratinocyte cell line, in the presence of a wound exudate sample or wound biofilm sample obtained from a non-healing skin wound includes the following steps:
      (i) culturing keratinocyte cells, wherein said keratinocyte cells are selected from the group consisting of primary human keratinocyte cells from healthy individuals and cells of a human keratinocyte cell line,
      (ii) incubating the keratinocyte cells on a solid support, thereby allowing the keratinocyte cells to adhere to the support,
      (iii) contacting the keratinocyte cells with the wound exudate sample or wound biofilm sample, which is optionally diluted, wherein the contacting may be performed before or after adherence of the keratinocyte cells occurs,
      (iv) determining the cell number of the keratinocyte cells,
      and/or
   iv) measuring the amount(s) of one or more M1 marker(s) and one or more M2 marker(s) in a supernatant of macrophages, which macrophages are generated from primary human monocytes from healthy individuals, incubated with a wound exudate sample or wound biofilm sample obtained from a non-healing skin wound includes the following steps:
      (i) co-culturing primary human monocyte cells from healthy individuals with (a) human dermal fibroblast cells from healthy individuals in 2D cell culture or (b) fibroblast-derived matrices,
      (ii) incubating the monocyte cells until macrophage differentiation is reached, thereby generating macrophages from primary human monocytes from healthy individuals,
      (iii) contacting the macrophage cells with a wound exudate sample or wound biofilm sample, which is optionally diluted,
      (iv) determining the amount of one or more M1 markers and one or more M2 markers in the supernatant, wherein the one or more M1 markers are selected from CXCL10 or IL-23p19, and the one or more M2 markers are selected from CCL22 or CCL18, and/or
   v) measuring the amount(s) and/or frequency distribution(s) of one or more M1 cell surface marker(s) and one or more M2 cell surface marker(s) on macrophages, which macrophages are generated from primary human monocytes from healthy individuals, incubated with a wound exudate sample or wound biofilm sample obtained from a non-healing skin wound includes the following steps:
      (i) co-culturing primary human monocyte cells from healthy individuals with (a) human dermal fibroblast cells from healthy individuals in 2D cell culture or (b) fibroblast-derived matrices,
      (ii) incubating the monocyte cells until macrophage differentiation is reached, thereby generating macrophages from primary human monocytes from healthy individuals,
      (iii) contacting the macrophage cells with a wound exudate sample or wound biofilm sample, which is optionally diluted,
      (iv) determining the amount(s) and/or frequency distribution(s) of one or more M1 marker(s) and one or more M2 marker(s) on the cell surface of the macrophages, wherein the one or more M1 cell surface markers are selected from the group consisting of CD38, CD64 and CD197, and the one or more M2 cell surface markers are selected from the group consisting of CD200 receptor (CD200R), CD206 and CD209, and/or
   vi) measuring the expression level(s) of one or more M1 marker mRNA(s) and one or more M2 marker mRNA(s) in macrophages, which macrophages are generated from primary human monocytes from healthy individuals, incubated with a wound exudate sample or wound biofilm sample obtained from a non-healing skin wound includes the following steps:

(i) co-culturing primary human monocyte cells from healthy individuals with (a) human dermal fibroblast cells from healthy individuals in 2D cell culture or (b) fibroblast-derived matrices, (ii) incubating the monocyte cells until macrophage differentiation is reached, thereby generating macrophages from primary human monocytes from healthy individuals, (iii) contacting the macrophage cells with a wound exudate sample or wound biofilm sample, which is optionally diluted, (iv) determining the expression level(s) of one or more M1 marker mRNA(s) and one or more M2 marker mRNA(s) in the macrophages, wherein the one or more M1 marker mRNA(s) are selected from the group consisting of CD38, CD64, CD197, CXCL10 and IL-23p19, and the one or more M2 marker mRNA(s) are selected from the group consisting of CD200 receptor (CD200R), CD206, CD209, CCL22 and CCL18, and/or vii) measuring the amount(s) of one or more cytokine markers selected from the group consisting of IL-1 alpha, IL-1beta and TNF-alpha in a supernatant of macrophages, which macrophages are generated from primary human monocytes from healthy individuals, incubated with a wound exudate sample or wound biofilm sample obtained from a non-healing skin wound includes the following steps:

(i) co-culturing primary human monocyte cells from healthy individuals with (a) human dermal fibroblast cells from healthy individuals in 2D cell culture or (b) fibroblast-derived matrices, (ii) incubating the monocyte cells until macrophage differentiation is reached, thereby generating macrophages from primary human monocytes from healthy individuals, (iii) contacting the macrophage cells with a wound exudate sample or wound biofilm sample, which is optionally diluted, (iv) determining the amount of one or more cytokine markers selected from the group consisting of IL-1alpha, IL-1beta and TNF-alpha in the supernatant.

* * * * *